(12) United States Patent
Bueno et al.

(10) Patent No.: US 6,410,528 B1
(45) Date of Patent: Jun. 25, 2002

(54) MORPHOLINO ETHERS

(75) Inventors: Jose M. Bueno; Jesus Chicharro Gonzalo; Jose-Miguel Coteron; Juan Carlos Cuevas; Jose M. Fiandor; Araceli Mallo, all of Madrid (ES)

(73) Assignee: Glaxo Wellcome S.A., Madrid (ES)

( * ) Notice: Subject to any disclaimer, the term of this patent is extended or adjusted under 35 U.S.C. 154(b) by 0 days.

(21) Appl. No.: 09/674,959

(22) PCT Filed: May 7, 1999

(86) PCT No.: PCT/EP99/03139

§ 371 (c)(1),
(2), (4) Date: Nov. 8, 2000

(87) PCT Pub. No.: WO99/58512

PCT Pub. Date: Nov. 18, 1999

(30) Foreign Application Priority Data

May 11, 1998 (EP) .............................. 98500117

(51) Int. Cl.$^7$ ...................... A61K 31/5375; A61P 33/00
(52) U.S. Cl. .................... 514/230.8; 544/154
(58) Field of Search ........................ 544/154; 514/230.8

(56) References Cited

FOREIGN PATENT DOCUMENTS

| EP | 0 711 783 A | 5/1996 |
| EP | 0 711 784 A | 5/1996 |
| EP | 0 712 859 A | 5/1996 |
| GB | 1 162 027 A | 8/1969 |
| WO | WO 97 42195 A | 11/1997 |
| WO | WO 98 11891 A | 3/1998 |
| WO | WO 98 15178 A | 4/1998 |
| WO | WO 99 09974 A | 3/1999 |
| WO | WO 99 09975 A | 3/1999 |

OTHER PUBLICATIONS

Patent Abstracts of Japan, vol. 11, No. 229, Jul. 25, 1987 & JP 62 040292 A, Feb. 21, 1987.

*Primary Examiner*—Robert W. Ramsuer
(74) *Attorney, Agent, or Firm*—Nixon & Vanderhye

(57) ABSTRACT

Compounds of formula (I)

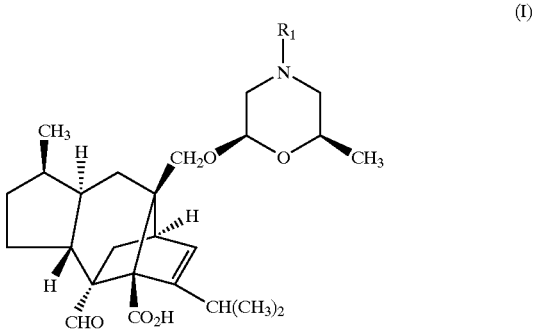

and pharmaceutically acceptable salts and or metabolically labile derivatives thereof, wherein $R^1$ represents $C_{1-6}$ straight or branched chain alkyl, $C_{1-6}$ straight or branched chain alkoxy, optionally substituted phenoxy, $C_{3-6}$ straight or branched chain alkenyloxy or $C_{1-4}$ straight or branched alkoxy substituted by an optionally substituted phenyl group. $C_{3-6}$ straight or branched chain alkenyl, optionally substituted phenyl, optionally substituted $C_{3-7}$ cycloalkyl, $C_{2-4}$ straight or branched chain alkyl substituted by ($C_{1-4,alkoxy}$, $C_{1-4}$ alkyl thio or halogen), $C_{1-4}$ straight or branched chain alkyl substituted by ($C_{1-4}$ alkoxycarbonyl, aryloxycarbonyl, cyano, optionally substituted $C_{3-7}$ cycloalkyl, optionally substituted 5 or 6 membered heteroaryl, or 1 or 2 optionally substituted phenyl groups), a process for their preparation and their use in medicine.

13 Claims, No Drawings

MORPHOLINO ETHERS

This invention relates to novel morpholino ethers having antifungal activity. More particularly it relates to novel sordaricin derivatives, to processes for their preparation, to pharmaceutical compositions containing them and to their use in medicine, more particularly in the prevention or treatment of diseases in animals, including humans, caused by fungal infection.

British Patent Specification No. 1,162,027 describes the preparation of an antibiotic, SL2266, by the cultivation of the strain NRRL 3196 of the fungus species *Sordaria araneosa*. SL 2266, later named sordarin, is reported to have fungistatic activity. The same research group also described in Helvetica Chimica Acta (1971), 51, 119–120 the degradation of sordarin to sordaricin. Published Japanese Patent Application No. J6 2040292A describes the preparation of an antibiotic, zofimarin, which is reported to have antifungal activity. Sordarin, sordaricin and zofimarin may be represented by formula (A) below

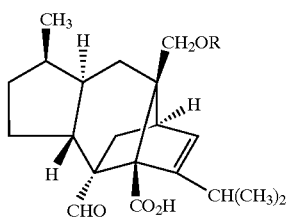

where
OR as

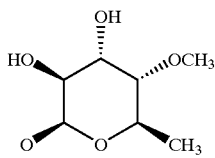

describes sordarin;
OR as OH describes sordaricin; and
OR as

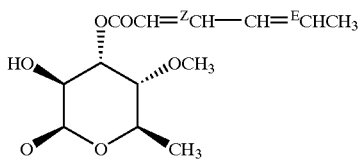

describes zofimarin.

Although sordarin and zofimarin exhibit antifungal activity, both compounds are only moderately active and have limited spectra of action when tested against a battery of fungal organisms.

WO96/14326 and WO96/14327 describe novel sordarin derivatives which exhibit useful antifungal activity. WO99/09974 and WO99/09975 describe 4-cyano-4-deformyl sordarin and sordaricin derivatives which exhibit antifungal activity.

We have now found a novel group of sordaricin derivatives which exhibit a useful spectrum of antifungal activity and which can be conveniently prepared from readily available starting material.

Thus according to a first aspect of the invention, we provide compounds of formula (I).

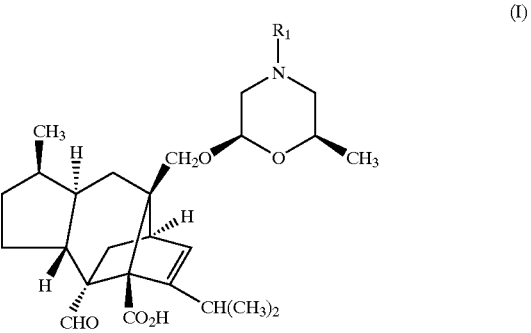

and physiologically acceptable salts and or metabolically labile derivatives thereof, wherein $R^1$ represents $C_{1-6}$ straight or branched chain alkyl, $C_{1-6}$ straight or branched chain alkoxy, optionally substituted phenoxy, $C_{3-6}$ straight or branched chain alkenyloxy (optionally substituted by 1 or 2 halogen atoms) or $C_{1-4}$ straight or branched alkoxy substituted by an optionally substituted phenyl group, $C_{3-8}$ straight or branched chain alkynyl, $C_{3-6}$ straight or branched chain alkenyl (optionally substituted by $C_{1-4}$alkoxy or 1 or 2 halogen atoms), optionally substituted phenyl, optionally substituted $C_{3-7}$ cycloalkyl, optionally substituted $C_{5-7}$ cycloalkenyl, $C_{2-4}$ straight or branched chain alkyl substituted by ($C_{1-4}$ alkoxy, $C_{1-4}$ alkyl thio or halogen), $C_{1-4}$ straight or branched chain alkyl substituted by ($C_{1-4}$ alkoxycarbonyl, arylalkyloxycarbonyl, aryloxycarbonyl, propadienyl, cyano, optionally substituted $C_{3-7}$ cycloalkyl, optionally substituted 5 or 6 membered heteroaryl, or 1 or 2 optionally substituted phenyl groups), or methyl substituted by $C_{1-6}$ alkanoyl or optionally substituted benzoyl; $R_2$ represents a group selected from hydrogen, $C_{1-6}$ straight or branched chain alkyl, $C_{3-6}$ straight or branched chain alkenyl, optionally substituted phenyl or $C_{1-4}$ alkyl substituted with a group selected from $C_{1-4}$alkoxy, hydroxy, acyloxy, alkoxycarbonyl or aryloxycarbonyl, and $R_3$ represents a group selected from formyl or cyano.

According to a second aspect of the present invention we provide compounds of formula (I) and physiologically acceptable salts and or metabolically labile derivatives thereof, wherein $R^1$ represents $C_{1-6}$ straight or branched chain alkyl, $C_{1-6}$ straight or branched chain alkoxy, optionally substituted phenoxy, $C_{3-6}$straight or branched chain alkenyloxy or $C_{1-4}$ straight or branched alkoxy substituted by an optionally substituted phenyl group, $C_{3-8}$ straight or branched chain alkynyl, $C_{3-6}$ straight or branched chain alkenyl (optionally substituted by $C_{1-4}$alkoxy or 1 or 2 halogen atoms), optionally substituted phenyl, optionally substituted $C_{3-7}$ cycloalkyl, optionally substituted $C_{5-7}$ cycloalkenyl, $C_{2-4}$ straight or branched chain alkyl substituted by ($C_{1-4}$ alkoxy, $C_{1-4}$ alkylthio or halogen), $C_{1-4}$ straight or branched chain alkyl substituted by ($C_{1-4}$ alkoxycarbonyl, arylalkyloxycarbonyl, aryloxycarbonyl, cyano, optionally substituted $C_{3-7}$ cycloalkyl, optionally substituted 5 or 6 membered heteroaryl, or 1 or 2 optionally substituted phenyl groups), or methyl substituted by $C_{1-6}$ alkanoyl or optionally substituted benzoyl; $R_2$ is methyl and $R_3$ is CHO.

Physiologically acceptable salts of the compounds of formula (I) include salts formed with physiologically acceptable acids or bases as well as internal salts.

Suitable physiologically acceptable salts of the compounds of formula (I) with bases include inorganic base salts such as alkali metal salts (for example sodium and potassium salts) and ammonium salts and organic base salts. Suitable organic base salts include amine salts such as trialkylamine (e.g. triethylamine), dialkylamine (e.g. dicyclohexylamine), optionally substituted benzylamine (e.g. phenylbenzylamine or p-bromobenzylamine), procaine, ethanolamine, diethanolamine, N-methylglucosamine and tri(hydroxymethyl)methylamine salts and amino acid salts (e.g. lysine and arginine salts).

Suitable physiologically acceptable acid addition salts includes those formed with inorganic acids such as hydrochloric acid, hydrobromic acid, phosphoric acid or sulphuric acid and organic acids such as acetic acid, propionic acid, succinic acid, lactic acid, tartaric acid, citric acid, maleic acid, benzoic acid or salicylic acid.

References hereinafter to a compound of formula (I) includes that compound and physiologically acceptable salts thereof.

Other salts which are not physiologically acceptable may be useful in the preparation of compounds of formula (I) and these form a further aspect of the invention.

Metabolically labile derivatives of compounds of formula (I) are compounds which are converted in the body into compounds of formula (I). Examples of such derivatives include conventional metabolically labile esters formed from the free carboxylic acid in the molecule. It is well known in the field of medicinal chemistry that there is a wide range of structurally distinct esters of carboxylic acid which are readily hydrolysed in the body to yield the parent carboxylic acid or a salt thereof and it is to be understood that the present invention encompasses all such esters.

It is to be understood that the present invention encompasses any individual isomers, including optical isomers, of compounds represented by formula (I) above as well as mixtures thereof, including wholly or partially racemic mixtures thereof.

When $R_1$ is $C_{1-6}$ straight or branched chain alkyl group examples of such groups include methyl, ethyl, propyl, isopropyl, butyl, isobutyl, secondary butyl or tertiary butyl, pentyl, isopentyl, 1-ethylpropyl, hexyl or isohexyl.

When $R_1$ is $C_{1-4}$ straight or branched alkoxy substituted by optionally substituted phenyl examples of such groups include phenylmethoxy, phenylethoxy or phenylpropoxy.

When $R_1$ is $C_{1-6}$ straight or branched alkoxy examples of such groups include methoxy, ethoxy, propoxy, isopropoxy, butoxy, isobutoxy, pentoxy or hexyloxy.

When $R_1$ is a $C_{3-6}$ alkenyl group examples of such groups include allyl, 2-methylallyl, 3-methylallyl or 3,3-dimethylallyl.

When $R_1$ is a $C_{3-6}$ alkenyl group substituted by $C_{1-4}$alkoxy this is conveniently $C_{3-6}$alkenyl substituted by methoxy e.g. 2-methoxyallyl or 2-methoxymethylallyl.

When $R_1$ is $C_{3-6}$ alkenyl substituted by one or two halogen atoms this is conveniently $C_{3-6}$alkenyl substituted by 1 or 2 halogen atoms selected from fluorine chlorine or bromine e.g. 2-fluoromethylallyl, 2-chloroallyl, 2-bromoallyl, 2-fluoroallyl, 3-fluoroallyl or 3,3-difluoroallyl.

When $R_1$ is $C_{3-6}$alkenyloxy optionally substituted by 1 or 2 halogen atoms this is conveniently $C_{3-6}$alkenyoxy optionally substituted by bromine or chlorine or fluorine e.g. allyloxy, 2-chloroallyloxy, 2-bromoallyloxy, 2-fluoroallyloxy.

The term aryl as a group or part of a group means optionally substituted phenyl.

The term optionally substituted phenyl as a group or part of a group e.g. phenoxy or phenylalkyl includes phenyl or phenyl substituted by 1 or 2 groups which may be the same or different and selected from $C_{1-4}$alkyl, halogen (fluorine, chlorine, bromine or iodine), hydroxy, $C_{1-4}$alkoxy, methylenedioxy or trifluoromethyl.

The term optionally substituted $C_{3-7}$ cycloalkyl as a group or part of a group is a cyclopropyl, cyclobutyl, cyclopentyl, cyclohexyl or cycloheptyl group which may be substituted by 1 or 2 methyl, methoxy, hydroxy or phenyl groups or may be fused to a phenyl ring to form a bicyclic ring system linked to the rest of the molecule via a carbon atom in with the cycloalkyl ring e.g. indanyl or tetrahydronaphthyl.

When $R_1$ is a $C_{2-4}$ alkyl group substituted by halogen examples of suitable groups include 2-chloroethyl, 2-fluoroethyl, trifluoroethyl.

The term straight or branched $C_{3-8}$alkynyl includes 2-propynyl, 1-methyl-2-propynyl and 3-methyl-2-propynyl or 1,1-dimethyl-2-propynyl.

When $R_1$ is $C_{5-7}$cycloalkenyl examples of such groups include cyclohexen-3-yl or cyclopenten-3-yl.

When $R_1$ is $C_{1-4}$ alkyl substituted by heteroaryl group, the term heteroaryl refers to a 5 or 6 membered heteroaryl group wherein the 5 membered group contains a single heteroatom selected from oxygen, sulphur or nitrogen and optionally contains 1 or 2 further nitrogen atoms, and the 6 membered group contains from 1 to 3 nitrogen atoms. Examples of such heteroaryl groups include furanyl, thienyl, pyrrolyl, oxazolyl, iso-oxazolyl, imidazolyl, pyrazolyl, thiazolyl, isothiazolyl, oxadiazolyl, thiadiazolyl, triazolyl, pyridyl, pyrimidiyl, pyridazinyl, pyrazinyl or triazinyl. The said heteroaryl groups may be substituted by one or two groups selected from $C_{1-4}$alkyl e.g. methyl, hydroxyalkyl e.g. hydroxymethyl,. acyloxyalkyl e.g. acetoxymethyl or halogen.

When $R_2$ is $C_{1-6}$alkyl examples of such groups include methyl, ethyl, propyl, butyl, t-butyl.

Examples of suitable $R_1$ groups include $C_{1-6}$alkyl (such as methyl, ethyl, propyl, isopropyl, n-butyl, 1-methylpropyl, t-butyl, 1-ethylpropyl, pentyl, 3-methylbutyl, 3,3-dimethylbutyl), $C_{1-4}$alkoxy e.g. methoxy, $C_{1-4}$alkoxy substituted by phenyl (e.g. phenylmethoxy), phenoxy, $C_{2-4}$alkyl substituted by $C_{1-4}$alkoxy (e.g. methoxyethyl, ethoxyethyl, ethoxypropyl, isopropoxypropyl), $C_{2-4}$alkyl substituted by $C_{1-2}$ alkylthio (e.g. ethylthioethyl), $C_{2-4}$ alkyl substituted by halogen (e.g. 2-chloroethyl, 2,2,2 trifluroethyl), $C_{1-4}$alkyl substituted by cyano (e.g. cyanomethyl or cyanoethyl), $C_{1-4}$ alkyl substituted by propadienyl (e.g. 2,3-butadienyl) optionally substituted $C_{3-6}$cycloalkyl e.g.[ (cyclopropyl optionally substituted by phenyl), cyclobutyl, cyclopentyl, cyclohexyl (optionally substituted by hydroxy or alkyl e.g. methyl), indanyl or tetrahydronaphthyl], phenyl, $C_{1-4}$ alkyl substituted by optionally substituted furanyl (e.g. furanylmethyl, hydroxymethylfuranylmethyl , acetoxymethylfuranylmethyl), pyridyl (e.g. pyridylmethyl or pyridylethyl), optionally substituted pyrrole e.g. (1-methylpyrrolemethyl) optionally substituted thiazolyl e.g. (thiazolylmethyl) optionally substituted imidazole e.g. N-hydroxymethylimidazolylmethyl $C_{1-4}$alkyl substituted by $C_{1-2}$alkoxycarbonyl (e.g. methoxycarbonylethyl, 1-methoxycarbonyl-2-methylpropyl), aralkyloxycarbonyl (e.g. benzyloxycarbonylmethyl) or aryloxycarbonyl (e.g. phenoxy carbonylmethyl), $C_{1-4}$alkyl substituted by optionally substituted $C_{3-6}$cycloalkyl (e.g. cyclopropylmethyl, cyclohexylmethyl, cyclohexylethyl, 1-cyclohexylethyl), $C_{3-6}$alkenyl (e.g. allyl, 2-methylallyl, 3-methylallyl, 3,3-dimethylallyl), $C_{3-6}$alkenyl substituted by alkoxy e.g. 2-methoxyallyl, 2-methoxymethylallyl, $C_{3-6}$alkenyl substituted by 1 or 2 halogen atoms selected from chlorine, bromine or fluorine e.g. (2-fluoromethylallyl, 2-chloroallyl, 2-bromoallyl, 2-fluoroallyl, 3-fluoroallyl, 3,3-difluoroallyl), $C_{3-6}$alkenyloxy optionally substituted by halogen (e.g. allyloxy, 2-chloroallyloxy), $C_{1-4}$alkyl substituted by 1 or 2 optionally substituted phenyl groups [wherein the optional substituent in the phenyl ring is selected from 1 or 2 halogen atoms, e.g. chlorine or fluorine, trifluromethyl, hydroxy, methoxy or methylenedioxy; (examples of such groups include optionally substituted benzyl e.g. benzyl, 4 methoxybenzyl, 4-trifluromethylbenzyl, difluorobenzyl such as 2,6-difluorobenzyl, 3,4-difluorobenzyl, 2,5 difluorobenzyl, or 2,4-difluorobenzyl, methylenedioxybenzyl, 1-phenyl ethyl, phenethyl (optionally substituted by 1 or 2 hydroxyl groups, methoxy, halogen e.g. fluorine or chlorine), phenylpropyl or diphenylmethyl)], $C_{3-8}$ alkynyl e.g. 2-propynyl, 1-methyl-2-propynyl, 3-methyl-2-propynyl, $C_{5-7}$cycloalkenyl e.g. 1-cyclohexen-3-yl, or methyl substituted by acetyl or benzoyl.

Examples of suitable $R_2$ groups include methyl, ethyl, t-butyl and phenyl.

Conveniently $R_1$ is a group selected from $C_{1-6}$alkyl e.g. methyl, ethyl, propyl, isopropyl, butyl, 1-methylpropyl, t-butyl, n-pentyl, 3-methylbutyl, $C_{1-4}$alkoxy e.g. methoxy, $C_{3-6}$ alkenyloxy (optionally substituted by halogen e.g. allyloxy, 2-chloroallyloxy), optionally substituted phenyl e.g. phenyl, $C_{3-6}$cycloalkyl e.g cyclopropyl, cyclobutyl, cyclopentyl, indanyl, tetrahydronaphthyl, $C_{2-4}$alkyl substituted by $C_{1-2}$alkoxy, e.g. methoxyethyl or ethoxypropyl, $C_{2-4}$alkyl substituted $C_{1-2}$alkylthio e.g. ethylthioethyl, $C_{1-4}$alkyl substituted by cyano e.g. cyanoethyl or cyanomethyl, $C_{1-4}$alkyl substituted by propadienyl e.g. 2,3-butadienyl, $C_{1-4}$alkyl substituted by alkoxycarbonyl (e.g. methoxycarbonylmethyl),$C_{1-4}$alkyl substituted by $C_{3-7}$cycloalkyl e.g. cyclopropylmethyl,$C_{1-4}$alkyl substituted by heteroaryl e.g. furylmethyl, pyridylmethyl, N-methylpyrrolylmethyl or thiazolylmethyl, $C_{1-4}$alkyl substituted by 1 or 2 optionally substituted phenyl groups e.g phenylmethyl, diphenylmethyl, difluorophenylmethyl (wherein the two fluorine atoms are in the 2,6, 2,4, 3,4 or 3,5 positions), trifluromethylphenylmethyl, methylenedioxyphenylmethyl, methoxyphenylmethyl, 1-phenylethyl or phenylethyl, $C_{3-6}$ alkenyl e.g allyl, 2-methylallyl, 3-methylallyl, 3,3-dimethylallyl, $C_{3-6}$alkynyl e.g. 2-propynyl, $C_{3-6}$alkenyl substituted by $C_{1-4}$alkoxy e.g. 2-methoxyallyl, 2-methoxymethylallyl, $C_{3-6}$alkenyl substituted 1 or 2 halogen atoms selected from chlorine, bromine or fluorine e.g. 2-chloroallyl, 2-bromoallyl, 2-fluoromethylallyl, 2-fluoroallyl, 3-fluoroallyl, 3,3-difluoroallyl, $C_{5-7}$cycloalkenyl e.g cyclohexen-3-yl or methyl substituted by acetyl or benzoyl.

Preferred $R_1$ groups include, methyl, ethyl, propyl, isopropyl, butyl, 1-methylpropyl, 3-methylbutyl, methoxy, cyclopropyl, allyl, 2-methylallyl, allyl substituted by halogen e.g. 2-chloroallyl, 2-fluoromethylallyl, 2-bromoallyl, 3,3-difluoroallyl, phenyl, ethylthioethyl, methoxyethyl, benzyl, furylmethyl, 2,6-difluorophenylmethyl, 3,4-difluorophenylmethyl, 3,5-difluorophenylmethyl, 3,4-methylenedioxyphenylmethyl, 4-methoxyphenylmethyl, 1-phenylethyl or propynyl, 2-3-butadienyl, allyloxy, 2-chloroallyloxy.

Preferred $R_2$ groups include methyl, ethyl, t-butyl or phenyl and more particularly methyl.

A preferred $R_3$ group is CHO.

A preferred group of compounds of formula (I) are those wherein $R_2$ is methyl and more particularly where $R_3$ is also CHO.

Preferred compounds of the invention include those wherein $R_1$ represents allyl, 2-methylallyl, 2-chloroallyl, 2-fluoromethylallyl, 2-bromoallyl, 3,3-difluoroallyl, 2-propynyl, cyclopropyl, 2,3-butadienyl or p-methoxy phenylmethyl.

A particularly preferred group of compounds of formula (I) include those wherein $R_1$ is allyl, 2-methyl allyl, 2-chloroallyl, 2-fluoromethylallyl, 2-bromoallyl, 3,3-difluoroalkyl, 2-propynyl, cyclopropyl, p-methoxyphenylmethyl or 2,3 butadienyl, $R_2$ is methyl and $R_3$ is CHO.

A particularly preferred compound of the invention is:
[1R-(1α,3aβ,4β,4aβ,7β,7aα,8aβ)]8a-[(2R,6R)-(4-(2-chloroallyl)-6-methyl-morpholin-2-yl)-oxymethyl]-4-formyl-4,4a,5,6,7,7a,8,8a-octahydro-7-methyl-3-(1-methylethyl)-1,4-methano-s-indacene-3a(1H)-carboxylic acid, and physiologically acceptable salts thereof e.g. alkali metal salts such as the sodium or potassium salts thereof.

Further particularly preferred compounds include:

[1R-(1α,3aβ,4β,4aβ,7β,7aα,8aβ)]8a-[(2R,6R)-(4-(2-methylallyl)-6-methyl-morpholin-2-yl)-oxymethyl]-4-formyl-4,4a,5,6,7,7a,8,8a-octahydro-7-methyl-3-(1-methylethyl)-1,4-methano-s-indacene-3a(1H)-carboxylic acid,

[1R-(1α,3aβ,4β,4aβ,7β,7aα,8aβ)]8a-[(2R,6R)-(4-(p-methoxybenzyl)-6-methyl-morpholin-2-yl)-oxymethyl]-4-formyl-4,4a,5,6,7,7a,8,8a-octahydro-7-methyl-3-(1-methylethyl)-1,4-methano-s-indacene-3a(1H)-carboxylic acid,

[1R-(1α,3aβ,4β,4aβ,7β,7aα,8aβ)]8a-[(2R,6R)-(4-(2,3-butadienyl)-6-methyl-morpholin-2-yl)-oxymethyl]-4-formyl-4,4a,5,6,7,7a,8,8a-octahydro-7-methyl-3-(1-methylethyl)-1,4-methano-s-indacene-3a(1H)-carboxylic acid, and physiologically acceptable salts thereof.

Yet further preferred compounds include:

[1R-(1α,3aβ,4β,4aβ,7β,7aβ,8aβ)]8a-[(2R,6R)-(4-cyclopropyl-6-methyl-morpholin-2-yl)-oxymethyl]-4-formyl-4,4a,5,6,7,7a,8,8a-octahydro-7-methyl-3-(1-methylethyl)-1,4-methano-s-indacene-3a(1H)-carboxylic acid,

[1R-(1α,3aβ,4β,4aβ,7β,7aα,8aβ)]8a-[(2R,6R)-(4-propynyl)-6-methyl-morpholin-2-yl)-oxymethyl]-4-formyl-4,4a,5,6,7,7a,8,8a-octahydro-7-methyl-3-(1-methylethyl)-1,4-methano-s-indacene-3a(1H)-carboxylic acid;

[1R-(1α,3aβ,4β,4aβ,7β,7aα,8aβ]8a-[(2R,6R)-(4-(2-bromoallyl)-6-methyl-morpholin-2-yl)-oxymethyl]-4-formyl-4,4a,5,6,7,7a,8,8a-octahydro-7-methyl-3-(1-methylethyl)-1,4-methano-s-indacene-3a(1 H)-carboxylic acid;

[1R-(1α,3aβ,4β,4aβ,7β,7aα,8aβ)]8a-[(2R,6R)-(4-allyl-6-methyl-morpholin-2-yl)-oxymethyl]-4-formyl-4,4a,5,6,7,7a,8,8a-octahydro-7-methyl-3-(1-methylethyl)-1,4-methano-s-indacene-3a(1H)-carboxylic acid;

[1R-(1α,3aβ,4β,4aβ,7β,7aα,8aβ)]8a-[(2R,6R)-(4-(3,3-difluoroallyl)-6-methyl-morpholin-2-yl)-oxymethyl]-4-formyl-4,4a, 5,6,7,7a,8,8a-octahydro-7-methyl-3-(1-methylethyl)-1,4-methano-s-indacene-3a(1H)-carboxylic acid;

[1R-(1α,3aβ,4β,4aβ,7β,7aα,8aβ)]8a-[(2R,6R)-(4-(2-fluoromethylallyl)-6-methyl-morpholin-2-yl)-oxymethyl]-4-formyl-4,4a,5,6,7,7a,8,8a-octahydro-7-methyl-3-(1-methylethyl)-1,4-methano-s-indacene-3a(1H)-carboxylic acid;

and physiologically acceptable salts thereof.

Preferred physiologically acceptable salts of compounds of the invention include alkali metal salts such as sodium and in particular potassium salts.

The compounds of formula (I) are useful in combating fungal and or protozoal infections in animals, including humans. For example, they may be used in the treatment of fungal infections including those caused by one or more organisms such as species of Candida (e.g. *Candida albicans, Candida glabrata, (Torulopsis glabrata), Candida tropicalis, Candida parapsilosis* and *Candida pseudotropicalis*), *Cryptococcus neoformans,* Aspergillus Spp (e.g. *Aspergillus flavus* and *Aspergillus fumigatus*), Coccidioides (e.g. *Coccidioides immitis*), Paracoccidioides (e.g. *Paracoccidioides brasiliensis*), Histoplasma (e.g. *Histoplasma capsulatum*) or Blastomyces (e.g. *Blastomyces dermatitidis*). They may also be used to treat other fungal infections caused by species of Trichophyton, Microsporum or Epidermophyton (e.g. *Trichophyton mentagrophytes, Trichophyton rubrum, Microsporum canis* or *Epidermophyton floccosum*), or in mucosal infections caused by *Candida albicans.*

Compounds of formula (I) may also be used to treat other infections caused by, other fungi such as Geotrichum (e.g. *Geotrichum clavatum*), Trichosporon (e.g. *Trichosporon beigelii*), Blastoschizomyces (e.g. *Blastoschizomyces capitatus*), Sporothrix (e.g. *Sporothrix schenckii*), Scedosporium (e.g. *Scedosporium apiosperum*), Cladosporium (e.g. *Cladosporium carrionii*) and *Pityrosporum ovale.*

The compounds of formula (I) may also be used to treat infections caused by protozoa such as Toxoplasma, Cryptosporidium, Leishmania, Tripanosoma, Giardia and Trichomonas.

The compounds of formula (I) may also be used to treat infections caused by *Pneumocystis carinii.*

The antifungal activity of the compounds of formula (I) may be determined using conventional in vitro and in vivo screens. Thus, the in vitro evaluation of the anti-fungal activity of compounds of the invention was performed on liquid or solid medium by the anti-fungal two-fold serial dilution technique of determining the minimum inhibitory concentration (MIC) of anti-fungal agent that inhibited development of growth after 24 to 48 hours of incubation at 37° C. In practice, a series of agar plates or broth microdilution panels containing two-fold dilutions of anti-fungal agent tested were inoculated with a standard culture of a clinically relevant pathogen, for example, *Candida albicans.* The agar plates or broth microdulution panels were then examined for the presence or absence of growth of the fungus and the appropriate MIC values were noted.

MFC values (defined as the lowest anti-fungal concentration that killed at least 99.9% of the initial inoculum in liquid medium) may also be determined by sub-culturing 0.01 and 0.1 µl of broth from the drug-free control well, the first well containing growth and each clear well on agar plates.

The fungicidal activity of the compounds of formula (I) may also be determined in conventional tests in animals e.g. rats and mice. For example the lethal systems candidiasis test in mice.

The compounds of formula (I) may also be useful in the control and or eradication of phytopathogenic fungi.

Compounds of the invention show particularly useful activity against one or more of the organisms selected from *Candida albicans, Candida glabrata, Candida tropicalis, Candida parapsilosis, Pneumocystis carinii Coccidioides immitis, Paracoccidioides brasiliensis, Histoplasma capsulatum* and *Blastomyces dermatitides.*

In view of their antifungal and or antiprotozoal activity, compounds of formula (I) recommend themselves for the treatment of a variety of fungal and or protozoal infections in human beings and animals. Such infections include superficial, cutaneous, subcutaneous and systemic mycotic infections such as respiratory tract infections, gastrointestinal tract infections, cardiovascular infections, urinary tract infections, CNS infections, candidiasis and chronic mucocandidiasis (e.g. thrush and vaginal candidiasis) and skin infections caused by fungi, cutaneous and mucocutaneous candidiasis, dermatophytoses including ringworm and tinea infections, athletes foot, paronychia, pityriasis versicolor, erythrasma, intertrigo, fungal nappy rash, candida vulvitis, candida balanitis and otitis externa. They may also be used as prophylactic agents to prevent systemic and topical fungal infections. Use as prophylactic agents may, for example, be appropriate as part of a selective gut decontamination regimen in the prevention of infection in immunocompromised patients (e.g. AIDS patients, patients receiving cancer therapy or transplant patients). Prevention of fungal overgrowth during antibiotic treatment may also be desirable in some disease syndromes or iatrogenic states. They may also be used in the prophylaxis and or treatment of infections caused by *Pneumocystis carinii.*

Thus in a further aspect the invention provides a method of the treatment of human or non human animal body to prevent or treat fungal and or protozoal diseases, which method comprises administering to solid body an effective amount of a compound of formula (I).

The invention also provides for the use of a compound of formula (I) in the manufacture of a medicament for the treatment or prevention of fungal and or protozoal infections.

While it is possible that, for use in therapy, compounds of the invention may be administered as the raw chemical, it is preferable to present the active ingredient as a pharmaceutical formulation. The invention thus further provides a pharmaceutical formulation comprising compounds of formula (I) and physiologically acceptable salts thereof together with one or more pharmaceutically acceptable carriers thereof and, optionally, other therapeutic and/or prophylactic ingredients. The carrier(s) must be 'acceptable' in the sense of being compatible with the other ingredients of the formulation and not deleterious to the recipient thereof.

The compositions of the invention include those in a form especially formulated for oral, buccal, parenteral, implant, rectal, topical, ophthalmic or genito-urinary administration or in a form suitable for administration by inhalation or insufflation.

Tablets and capsules for oral administration may contain conventional excipients such as binding agents, for example, syrup, acacia, gelatin, sorbitol, tragacanth, mucilage of starch or polyvinylpyrrolidone; fillers, for example, lactose, sugar, microcrystalline cellulose, maize-starch, calcium phosphate or sorbitol; lubricants, for example, magnesium stearate, stearic acid, talc, polyethylene glycol or silica; disintegrants, for example, potato starch or sodium starch glycollate or crosscarmellose sodium; wetting agents such as sodium lauryl sulphate and pH modifiers for example citric acid, malic acid, tartaric acid, sodium carbonate, sodium bicarbonate, triethanolamine or trometamol. The capsule may contain powders, tablets, pellets, granules, liquids, waxes, surfactants or any combination of the former, which may be coated according to the methods well known to the art. The content of the capsules can be made of: binding agents, fillers, lubricants, desintegrants, wetting agents and pH modifiers, as described above. The tablets which include chewable, dispersible or effervescent tablets may be coated according to methods well known in the art.

Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, for example, sorbitol syrup, methyl cellulose, glucose/sugar syrup, gelatin, hydroxyethylcellulose, carboxymethyl cellulose, aluminium stearate gel or hydrogenated edible fats; emulsifying agents, for example, lecithin, sorbitan mono-oleate or acacia; non-aqueous vehicles (which may include edible oils), for example, almond oil, fractionated coconut oil, oily esters, propylene glycol or ethyl alcohol; and preservatives, for example, methyl or propyl p-hydroxybenzoates or sorbic acid and flavouring agent.

For buccal administration the composition may take the form of tablets or lozenges formulated in conventional manner.

The composition according to the invention may be formulated for parenteral administration by injection or continuous infusion. Formulations for injection may be presented in unit dose form in ampoules, or in multi-dose containers with an added preservative. The compositions may take such forms as suspensions, solutions, or emulsions in oily or aqueous vehicles, and may contain formulatory agents such as suspending, stabilising and/or dispersing agents. Alternatively the active ingredient may be in powder form for constitution with a suitable vehicle, e.g. sterile, pyrogen-free water, before use.

For administration by inhalation the compositions according to the invention are conveniently delivered in the form of an aerosol spray presentation from pressurised packs with the use of a suitable propellant, e.g. dichlorodifluoromethane, trichlorofluoromethane, dichlorotetrafluoroethane, carbon dioxide or other suitable gas, or from a nebuliser. In the case of a pressurised aerosol the dosage unit may be determined by providing a valve to deliver a metered amount.

Alternatively, for administration by inhalation the compositions according to the invention may take the form of a dry powder composition, for example a powder mix of the compound and a suitable powder base such as lactose or starch or as a modified physical form of the drug substance alone. The powder composition may be presented in unit dosage form in, for example, capsules or cartridges of e.g. gelatin, or blister packs from which the powder may be administered with the aid of an inhaler or insufflator.

The compositions may take the form of a suppository, e.g. containing a conventional suppository base, or a pessary, e.g. containing a conventional pessary base.

The compositions may also be formulated for topical administration in the form of ointments, creams, gels, lotions, shampoos, powders (including spray powders), pessaries, tampons, sprays, dips, aerosols, drops (e.g. eye, ear or nose drops) or pour-ons. Ointments and creams may, for example, be formulated with an aqueous or oily base with the addition of suitable thickening and/or gelling agents. Ointments for administration to the eye may be manufactured in a sterile manner using sterilised components. Pour-ons may, for example, be formulated for veterinary use in oils containing organic solvents, optionally with formulatory agents, e.g. stabilising and solubilising agents. Pessaries and tampons for vaginal insertion may be formulated using conventional techniques and, where appropriate, may contain an effervescent vehicle. Such compositions may also contain other active ingredients such as corticosteroids, antibiotics or antiparasitics as appropriate.

Liquid preparations for intranasal delivery may take the form of solutions or suspensions and may contain conventional excipients such as tonicity adjusting agents, for example, sodium chloride, dextrose or mannitol; preservatives, for example benzalkonium chloride, thiomersal, phenylethyl alcohol; and other formulating agents such as suspending, buffering, stabilising, dispersing and or flavouring agents.

Transdermal administration may be affected by the design of a suitable system which promotes absorption of the active compound through the skin and would typically consist of a base formulation enclosed within an adhesive stick-on patch comprising backing films, membranes and release liners. Such systems may include absorption enhancers such as alcohols or work by promoting ionotophoresis.

The composition according to the invention may also be formulated as a depot preparation. Such long acting formulations may be administered by implantation (for example subcutaneously or intramuscularly) or by intramuscular injection. Thus, for example, a compound of the invention may be formulated with suitable polymeric or hydrophobic materials (for example as an emulsion in an acceptable oil) or ion exchange resins, or as sparingly soluble derivatives, for example, as a sparingly soluble salt.

When the compositions comprise dosage units, each unit will preferably contain 0.001 mg to 1000 mg, advantageously 0.01 mg to 400 mg, of active ingredient where a compound of the invention is to be administered orally. The daily dosage as employed for adult human treatment will preferably range from 0.001 mg to 5000 mg of active ingredient, most preferably from 0.01 mg to 2000 mg which may be administered in 1 to 4 daily doses, for example, depending on the route of administration and on the condition of the patient and the disease to be treated.

The compound may be administered by intravenous infusion using, for example, up to 50 mg/kg/day of the active ingredient. The duration of treatment will be dictated by the rate of response rather than by arbitrary numbers of days.

Compounds of the invention may also be used in combination with other therapeutic agents, and the invention thus provides, in a further aspect, a combination comprising a compound of the invention together with another therapeutically active agent.

Thus for example the compounds of the invention may be used in combination with one or more other antifungal agents, such as a polyenic derivative e.g. (Amphotericin B, Nystatin, a lipid formulation of Amphotericin B) an azole derivative e.g. (Fluconazole, Intraconazole, Ketoconazole, Miconazole, Clotrimazole, ZD-08070, UK-109496), 5-Fluorocytosine, a Pneumocandin or Echinocandin derivative (such as Cilofungin, LY-303366, L-733560), an allylamine derivative (e.g. Terbinafine, Butenafine or Naftifine), and/or one or more immunomodulating agents such as an interferon e.g. (IFN-γ), interleukine e.g. (IL-1, IL-2, IL-3 and IL-8) and colony stimulating factors, [(G)-CSF, (M)-CSF and (GM)-CSF] and defensines. Particularly advantageous compounds for use with compounds of the invention include Intraconazole, Flucytosine, Fluconazole, Terbinafine or Amphotericin B.

When the compounds of the invention are administered in combination with another antifungal agent the compounds of the invention and the other fungal agent can be administered at the recommended maximum clinical dosage or at lower doses.

The combinations referred to above may conveniently be presented for use in the form of a pharmaceutical formulation and thus pharmaceutical formulations comprising a combination as defined above together with a pharmaceutically acceptable carrier thereof comprise a further aspect of the invention. The individual components of such combinations may be administered either sequentially or simultaneously in separate or combined pharmaceutical formulations.

When a compound of the invention is used in combination with a second therapeutic agent against the same condition the dose of each compound may differ from that when the compound is used alone. Appropriate doses will be readily appreciated by those skilled in the art.

According to another aspect of the present invention, we provide a compound of formula (I) or a physiologically acceptable salt thereof or a pharmaceutical composition comprising a compound of formula (I) or a physiologically acceptable salt thereof as defined above for use in therapy, particularly for the treatment of fungal infections in animals (especially humans).

According to another aspect of the present invention, we provide the use of a compound of formula (I) or a physiologically acceptable salt thereof in the manufacture of a medicament for the treatment of fungal infections in a human or non-human animal patient.

According to a further aspect of the present invention, we provide a method of treatment of the human or non-human animal body to combat fungal diseases, which method comprises administering to said body an effective amount of a compound of formula (I) or a physiologically acceptable salt thereof.

It will be appreciated by those skilled in the art that references herein to treatment extend to prophylaxis as well as the treatment of established conditions or infections.

For use as against phytopathogenic fungi the compounds may be formulated in conventional manner.

The invention also provides processes for the preparation of compounds of formula 1.

Thus the invention provides process A for the preparation of compounds of formula (I) wherein $R_2$ is methyl and $R_3$ is CHO or a physiologically acceptable salt thereof which comprises reacting a compound of formula (II) wherein $R_4$ is hydrogen, a carboxyl protecting group or a cation and $R_3$ is the group CHO or a protected derivative thereof,

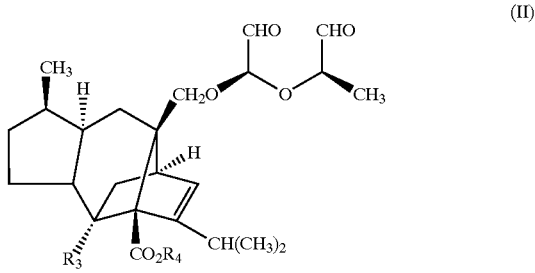

(II)

with the amine (III, wherein $R_1$ has the meanings defined above or is a protected derivative thereof), or an acid addition salt thereof, $R_1NH_2$ (III)

under reductive amination conditions followed by removal of any protecting groups $R_4$ and or $R_3$ and isolation of the compounds as the free acid or a salt thereof. In a preferred aspect of this process at least one of the R4 or $R_3$ is a protected group.

For use in this reaction suitable carboxyl protecting groups $R_4$ include arylmethyl such as optionally substituted benzyl or diphenylmethyl derivatives. Alternative substituted methyl esters that can be used as carboxyl protecting groups include trialkylsilylalkyloxymethyl e.g. trimethylsilylethyloxymethyl or allyl. When $R_4$ is a cation it is conveniently a cation of an alkali or alkaline earth metal such as sodium. When $R_3$ is a protected aldeyhyde group this is conveniently an acetal, for example an acetal of a $C_{1-4}$ alkanol e.g. methanol or ethanol or 1,2 or 1,3 diol such as ethylene glycol, 1,2-propanediol or 1,3-propanediol.

In one embodiment of this process the reductive amination reaction is conveniently carried out in an suitable solvent solution such as an acetonitrile and in the presence of a suitable reducing agent such as borohydride e.g. sodium borohydride, sodium cyanoborohydride or sodium triacetoxy borohydride When the amine (III) is used in the form of its free base then the reductive amination is conveniently carried out in the presence of an acid e.g. an organic acid such as acetic acid. If the amine (III) is used in the form of an acid addition salt thereof e.g. the hydrochloride salt then the reductive amination is conveniently carried out in the presence of a tertiary organic base such as a trialkylamine e.g. triethylamine.

In a further embodiment of this process the reductive aminationis carried out in a solvent such as acetonitrile in the presence of benzotriazole and a reducing agent such as sodium borohydride.

The carboxyl protecting group $R_4$ may be removed by conventional means. Thus when $R_4$ is an arylmethyl group it may be removed by hydrogenolysis using hydrogen and a suitable catalyst e.g. Palladium on charcoal in a suitable solvent e.g. ethyl acetate. Alternatively when $R_2$ is a diphenylmethyl group it may be removed by treatment with an acid such as trifluoroacetic acid.

The trimethylsilylethyloxymethyl ester may be cleaved by reaction with fluoride ions e.g. tetrabutylammonium fluoride in a suitable aprotic solvent such as an ether e.g. tetrahydrofuran.

When $R_3$ is a protected aldehyde group this may be converted into the corresponding aldehyde by conventional means. Thus if $R_3$ is an acetal group it may be converted into the aldehyde group by treatment with an acid e.g. organic acid such as trifluoroacetic acid or an aqueous mineral acid e.g. aqueous hydrochloric acid.

The compound of formula (I) may be conveniently isolated after removal of any protecting groups as the free acid which may exist in the form of an internal salt.

Salts of compounds of formula (I) with inorganic or organic bases may be prepared by treating a solution or suspension of the compound of formula (I) e.g. a suspension in a solvent such as methanol or tetrahydrofuran or a mixture of acetonitrile and tetrahydrofuran with an equivalent amount of the base (e.g potassium hydroxide or sodium hydroxide) optionally in a solvent e.g. water.

The salts may then be isolated by conventional means such as total or partial removal of the organic solvent followed by lyophilisation or crystallisation.

Acid addition salts of the compounds of formula (I) may be prepared by treating the compound with the appropriate inorganic or organic acid. Conveniently the salt formation is carried out by treating a suspension of the compound in dioxan with the appropriate acid followed by removal of the solvent.

The compounds of formula (I) may be prepared by oxidation of a compound of formula (IV) in which $R_4$ and $R_3$ have the meanings defined above:

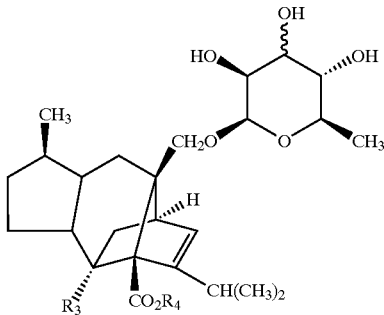

(IV)

The oxidation may be carried out using a suitable oxidising agent such as periodate e.g. an alkali metal periodate e.g. sodium periodate and conveniently in a solvent such as water or an aqueous alkanol such as aqueous methanol and conveniently in the presence of a base such as sodium bicarbonate. Alternatively the oxidation may be carried out using lead tetracetate.

It will be appreciated that compound (II) thus obtained may be in equilibrium with the cyclic compound (IIa):

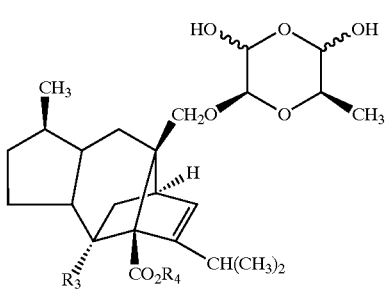

(IIa)

Compounds of formula (II) wherein $R_3$ is a protected aldehyde group and $R_4$ is hydrogen are conveniently prepared by conventional means from the corresponding compound of formula (II) wherein $R_4$ is hydrogen and $R_3$ is CHO. For example the acetal may prepared by reaction with the appropriate diol e.g. ethylene glycol in the presence of an acid catalyst such as p-toluene sulphonic acid and an orthoformate e.g. trimethyl orthoformate, in a solvent such as acetonitrile.

Compounds of formula (IV) wherein $R_4$ is a carboxyl protecting group and $R_3$ is CHO may be prepared from compounds wherein $R_4$ is hydrogen, using conventional procedures for esterifying a carboxyl group.

Thus a compound of formula (IV) wherein $R_4$ is diphenylmethyl may be prepared by treating the corresponding carboxylic acid with diphenyl-diazo-methane in a suitable solvent e.g. dichloromethane.

Compounds of formula (IV) wherein $R_3$ is a protected aldeyhde group may be prepared from the corresponding compound of formula (IV) wherein $R_3$ is CHO by conventional means. Thus a compound of formula (IV) wherein $R_3$ is a cyclic acetal may be prepared by treating the corresponding aldehyde with the diol in the presence of an acid catalyst such as p-toluene sulphonic acid and trimethyl orthoformate in the suitable solvent e.g. an alkanol such as methanol.

The compounds of formula (IV) wherein $R_4$ is hydrogen and $R_3$ is CHO are known compounds and may be prepared using the procedures described in WO97/42195 and WO96/14327.

In a further process B according to the invention compounds of formula (I) wherein $R_3$ is CHO and $R_2$ is methyl may be prepared by alkylation of a compound of formula (V),

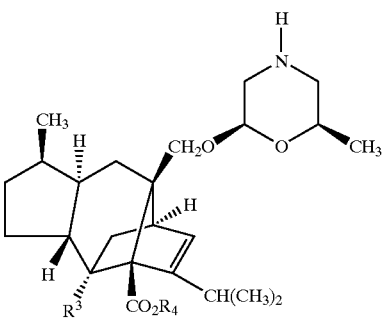

(V)

wherein $R_3$ is an aldehyde or a protected aldehyde group as defined above and $R_4$ is a carboxyl protecting group or hydrogen or a cation, followed by removal of any protecting groups.

In one embodiment of this process the alkylation may be carried out by reacting compound (V) with the alkylating agent (VI, $R_{1a}Y$, wherein $R_{1a}$ has the meaning defined above for $R_1$ and Y is a leaving group e.g. a halogen atom such as bromine or iodine, or a mesylate or p-toluenesulphonate group) or the alkylating agent $R_{1a}Y$ is a reagent capable of reacting with compound (V) to introduce the group $R_1$.

This reaction is conveniently carried out in the presence of an inorganic base e.g. an alkali metal carbonate or bicarbonate e.g. sodium carbonate or sodium bicarbonate and in a solvent e.g. a polar solvent such as alkanol e.g. ethanol and preferably with heating.

In a further embodiment of process B the compound of formula (V) may be alkylated by reaction with an appropriate aldeyhyde or ketone (VII $R_aR_bCO$) under reductive alkylation conditions. The reaction with the required aldehyde or ketone is carried out in the presence of a reducing agent, e.g. a borohydride such as sodium borohydride and in the presence of acetic acid or hydrogen and a metal catalyst e.g. palladium or charcol.

When the above reaction is carried out with a compound (VII) which is an aldehyde $R_b$ represents hydrogen and $R_a$ has the meanings such that the group $R_aCH_2$ has the required meaning of $R_1$.

When the reaction is carried out with a ketone of formula (VII) the groups $R_a$ and $R_b$ are linked together and with the carbon atom to which they are attached form the desired group $R_1$.

In a further embodiment of this process compounds of formula (I) wherin R1 is 2,3-butadienyl may be prepared by reacting a compound of formula (V) with paraformaldehyde and propargyltrimethyl-silane in the presence of an acid such as camphorsulphonic acid, in a solvent such as acetonitrile and with heating.

The compound of formula (V) may be prepared by reacting the corresponding compound of formula (II) wherein $R_4$ and $R_3$ have the meanings defined above with an ammonia source (eg ammonia or ammonium hydroxide) in a suitable solvent e.g. an ethanol such as methanol or ethanol or acetonitrile under reductive amination conditions. For example in the presence of hydrogen and a suitable catalyst such as palladium e.g. palladium or charcoal or with a borohydride such as sodium borohydride or with sodium borohydride in the presence of benzotriazole.

In a further process C according to the invention compounds of formula (I) wherein $R_3$ is CHO may be prepared by reacting a sordaricin derivative (VIII) wherein $R_4$ is a carboxyl protecting group as defined above and Z is a leaving group, (VIII)

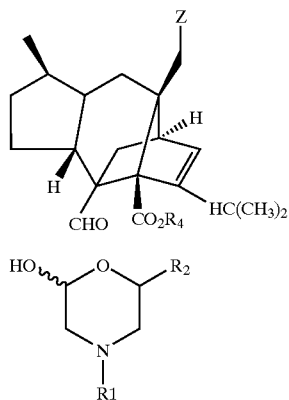

(IX)

with the morpholino alcohol (IX) wherein $R_1$ and $R_2$ have the meanings defined in formula 1 or are groups convertible thereto.

For the compounds of formula (VIII) the leaving group Z is conveniently a polyfluoro-$C_{1-4}$alkylsulphonyloxy group e.g. a trifluoromethyl-sulphonyloxy group. The reaction is carried out in the presence of a base such as an alkali metal base e.g. an alkali metal hydride such as sodium hydride, an alkali metal alkoxide such as potassium tert butoxide or an alkali metal carbonate such as cesium carbonate and optionally in the presence of a tetra-alkylammonium trifluoromethanesulphonate salt e.g. tetrabutyl-ammonium trifluoromethanesulphonate. Conveniently the reaction is carried out in a solvent selected from an ether e.g. 1,4-dioxan, a $C_{1-4}$ alkanol e.g. isopropanol or a halohydrocarbon e.g. dichloromethane and at a temperature within the range 0–100° e.g. 10–40°. Desirably the reaction is also carried out in the presence of an agent capable of absorbing water e.g. molecular sieves.

The compound (VIII) may be prepared from the protected sordaricin compound (X) wherein $R_4$ is a carboxyl protecing group by conventional procedures.

(X)

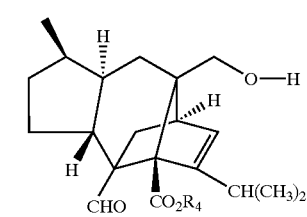

For example compounds of formula (IX) wherein Z is a polyfluoroalkylsulphonyloxy group may be prepared by reacting compound (X) with the corresponding polyfluoroalkyl sulphonyl halide, or polyfluoroalkyl sulphonic anhydride in the presence of a base e.g. an aromatic tertiary amine such as an optionally substituted pyridine e.g. pyridine or lutidine in a solvent such as a halohydrocarbon e.g. dichloromethane. The reaction is also desirably carried out in the presence of an inorganic base such as cesium carbonate.

The compounds of formula (X) are either known compounds or may be prepared by analogous methods described from preparing the known compounds for example by esterification of the compound of formula (X) wherein $R_4$ is hydrogen (sordaricin) using conventional methods to introduce the required carboxyl protecting group $R_4$.

The morpholino alcohol (IX) may be prepared by reaction of the amine derivative (XI) wherein $R_1$ has the meanings defined in formula (I).

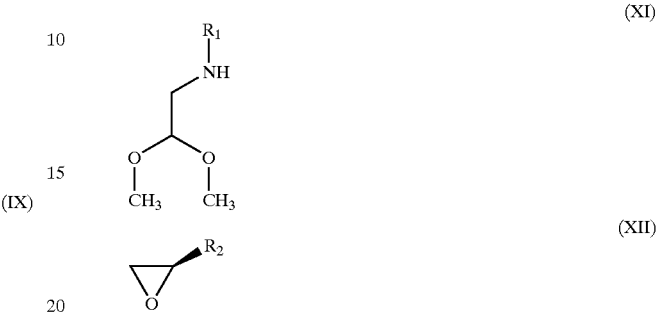

with the ethylene oxide derivative (XII) in a solvent such. as an alkanol e.g. ethanol followed by treatment with a mineral acid e.g. hydrochloric acid.

The compounds of formula (XI) and (XII) are either known compounds or may be prepared by analogous methods to those described for preparing the known compounds.

In the above processes B and C the carboxyl protecting group $R_4$ or the protected aldehyde group $R_3$ may be converted into the required acid and or aldehyde using the procedure described above with respect to process A.

Compounds of formula (I) or protected derivatives there of may be converted into compounds of formula (I).

Thus compounds of formula (I) wherein $R_3$ is CN may be prepared from the corresponding compound of formula (I) wherein $R_3$ is CHO by reaction with hydroxylamine in a solvent such as toluene and then treatment of the resultant oxime with acetic anhydride and with heating.

Compounds of formula (I) wherein $R_1$ is an optionally substituted allyloxy group may be prepared from the corresponding allyl derivative by reaction with a suitable oxidising agent e.g. a perbenzoic acid such as 3-chloroperbenzoic acid. The reaction is preferable carried out by treating the allyl compound with the perbenzoic acid in a solvent such as dichloromethane, removal of the solvent, and then heating the resultant mixture in the presence of a solvent such as acetonitrile or tetrahydrofuran or a mixture thereof.

The compounds of formula (II), (IIa), (V), (VIII) and (IX) are novel and represent further aspects of the invention.

The following examples, which a re non-limiting illustrate the invention;

The intermediates and examples have been characterised by NMR determined on a Varian Unity 300 $MH_z$ apparatus.

Intermediate 1

[1R-(1α,3aβ,4β,4aβ,7β,7aα,8aβ)]8a-[(6-deoxy-β-D-altropyranosyloxy)methyl]-4-(1,3-dioxolan-2yl)-4,
4a,5,6,7,7a,8,8a-octahydro-7-methyl-3-(1-methylethyl)-1,4-methano-s-indacene-3a(1H)-carboxylic acid, diphenylmethyl ester.

To a solution of [1R-(1α,3aβ,4β,4aβ,7β,7aα,8aβ)]8a-[(6-deoxy-β-D-altropyranosyloxy)methyl]-4-formyl-4,4a,5,6,7,7a,8,8a-octahydro-7-methyl-3-(1-methylethyl)-1,4-methano-s-indacene-3a(1H)-carboxylic acid (14 g) in 215 ml of a mixture dichloromethane:methanol v:v 20:1 was added dropwise 250 ml of 0.35 N solution of diphenyldiazomethane in dichloromethane. After 30 minutes of stirring 1N HCl (180 ml) was added carefully and the mixture vigorously stirred until the purple colour disappeared. The two phases were partitioned and the organic layer washed with saturated aqueous sodium bicarbonate solution (500 ml) and dried over sodium sulphate. Elimination of the solvent gave a brown foamy crude which was purified by flash chromatography (silica gel), eluting firstly with dichloromethane, then with 10% methanol in dichloromethane. The material thus obtained was dissolved in methanol (100 ml) and heated to 40° C. To the warm solution was added ethylene glycol (50 ml), trimethyl orthoformate (6.5 ml) and p-toluenesulphonic acid (209 mg). Once the reaction was concluded the mixture was cooled to room temperature and ethyl acetate (500 ml) was added onto them (TLC control Hexane:Acetone v:v 1:1).

Aqueous saturated sodium bicarbonate (50 ml) was added and the two phases partitioned. The organic layer was washed with water (500 ml) and brine (500 ml), then dried over sodium sulphate and concentrated to dryness. The foamy residue was dissolved in the minimal amount of diethyl ether and hexane was added dropwise until cloudy suspension was obtained, then they was cooled in the freezer overnight. The white solid thus obtained by precipitation was filtered off to obtain the desired product as white solid (85–90% overall yield from starting triol).

$^1$H-NMR (CDCl$_3$, ppm): 7.5–7.2 (m, 10H, Ph$_2$), 6.94 (s, 1H, CHPh$_2$), 5.83 (dd, 1H, H2, J=1.5 and 3.6 Hz), 5.07 (s, 1H, OCHO), 4.64 (d, 1H, H1', J=1.8 Hz), 4.05 (m, 2H, 8aCH$_2$+H2'), 3.90– 3.65 (m, 8H, H3',+H4'+H5'+8aCH$_2$+ OCH$_2$CH$_2$O), 2.64 (m, 1H, CH(CH$_3$)$_2$), 2.52 (t, 1H, H1, J=3.9 Hz), 2.35, 2.27, 2.02 (3d, 3OH, J=2.4, 3.6 and 5.7 Hz).

Intermediate 2

[1R-(1α,3aβ,4β,4aβ,7β,7aα,8aβ)]8a-[(6-deoxy-β-D-mannopyranosyloxy)methyl]-4-(1,3-dioxolan-2-yl)-4,4a,5,6,7,7a,8,8a-octahydro-7-methyl-3-(1-methylethyl)-1,4-methano-s-indacene-3a(1H) carboxylic acid, diphenylmethyl ester was prepared using the procedure of Intermediate 1 but starting from [1R-(1α,3aβ,4β,4aβ,7β,7aα,8aβ)]8a-[(6-deoxy-β-D-mannopyranosyloxy)methyl]-4-formyl-4,4a,5,6,7,7a,8,8a-octahydro-7-methyl-3-(1-methylethyl)-1,4-methano-s-indacene-3a(1H) carboxylic acid.

$^1$H-NMR (CDCl$_3$, ppm): 7.5–7.2 (m, 10H, Ph$_2$), 6.94 (s, 1H, CHPh$_2$), 5.82 (dd, 1H, H2, J=1.2 and 3.6 Hz), 5.08 (s, 1H, OCHO), 4.31 (d, 1H, H1', J=1.2 Hz), 4.07 (d, 1H, 8aCH$_2$, J=9.3 Hz), 3.94 (m, 1H, H3'), 3.9–3.75 (m, 4H, OCH$_2$CH$_2$O), 3.42 (m, 2H H2'+4'), 3.24 (m, 1H, H5'), 2.64 (m, 1H, CH(CH$_3$)$_2$), 2.54 (m, 2H, H1+OH), 2.36 (bs, 1H, OH), 2.33 (d, 1H, OH, J=2.4 Hz).

Intermediate 3

[1R-(1α,3aβ,4β4aβ7β,7aα,8aβ)]4-(1,3-dioxolan-2-yl)-8a-[((2R4)-4-methyl-3-oxa-pentanedial-2-yl)-oxymethyl]-4,4a,5,6,7,7a,8,8a-octahydro-7-methyl-3-(1-methylethyl)-1,4-methano-s-indacene-3a(1H)-carboxylic acid diphenylmethylester To a solution of intermediate 1 (23 g) in methanol (625 ml) w as added solid sodium bicarbonate (5.62 g). To this suspension at 35° C. was added dropwise with vigorous stirring a solution of sodium periodate (35.7 g) in water (300 ml) over a period of 2 h. Once the addition had been concluded, the suspension was stirred for 48 h at 35° in the dark. The white solid was filtered off, the filter cake washed with methanol (200 ml) and the combined filtrate and washing concentrated under vacuum to remove the methanol. Ethyl acetate (600 ml) was added and the two phases partitioned. The organic layer was washed twice with brine (2×100 ml), dried over sodium sulphate and then the solvent removed under reduced pressure. After drying under vacuum the title compound (22.3 g) was obtained as a white foam. This product was used in the reductive amination reactions described below without further purification.

Intermediate 3 may also be prepared using the above procedurre but using intermediate 2 as the starting material.

Intermediate 4—General Procedure

To a solution of the Intermediate 3 (200 mg) in dry acetonitrile (5 ml) were added sodium cyanoborohydride (39 mg), the corresponding primary amine* (2 equiv) and acetic acid (18 μl). The mixtures were stirred at room temperature until completion (2–3 hours). The suspensions thus obtained were then diluted with water (3 vol) and the milky suspensions extracted with ethyl acetate (1 vol). The organic layer was washed with brine (2×10 ml) and the aqueous layers back extracted with ethyl acetate (10 ml). The organic layers were dried over sodium sulphate and concentrated to dryness. The oily product thus obtained was dissolved in the minimal amount of dichloromethane and filtered through a short silica gel column using hexane:acetone v:v 15:1. Solvent elimination of the appropriate fractions yielded the desired crude amines as white foams which were used without further purification.

Using the above procedures the following compounds were prepared.

Intermediate 4a 1R-(1α,3aβ,4β,4aβ,7β,7aα,8aβ)8a-[(2R,6R)-(4-cyclopropyl-6-methyl-morpholin-2-yl)-oxymethyl]-4-(1,3-dioxolanyl-2-yl)-4,4a,5,6,7,7a,8,8a-octahydro-7-methyl-3-(1-methylethyl)-1,4-methano-s-indacene-3a(1H)-carboxylic acid, diphenylmethyl ester Intermediate 4b

[1R-(1α,3aβ,4β,4aβ,7β,7aα,8aβ)8a-[(2R,6R)-(4-ethyl-6-methyl-morpholin-2-yl)-oxymethyl]-4-(1,3-dioxolan-2-yl)-4,4a,5,6,7,7a,8,8a-octahydro-7-methyl-3-(1-methylethyl)-1,4-methano-s-indacene-3a(1H)-carboxylic acid, diphenylmethyl ester Intermediate 4c

[1R-(1α,3aβ,4β,4aβ,7β,7aα,8aβ)]8a-[(2R,6R)-(4-allyl-6-methyl-morpholin-2-yl)-oxymethyl]-4-(1,3-dioxolan-2-yl)-4,4a,5,6,7,7a,8,8a-octahydro-7-methyl-3-(1-methylethyl)-1,4-methano-s-indacene-3a(1H)-carboxylic acid, diphenylmethylester Intermediate 4d

[1R-(1α,3aβ,4β,4aβ,7β,7aα,8aβ)]8a-[(2R,6R)-4-(2-methoxyethyl)-6-methyl-morpholin-2-yl)-oxymethyl]-4-(1,3-dioxolan-2-yl)-4,4a,5,6,7,7a,8,8a-octahydro-7-methyl-3-(1-methylethyl)-1,4-methano-s-indacene-3a(1H)-carboxylic acid, diphenylmethyl ester

Intermediate 4e

[1R-(1α,3aβ,4β,4aβ,7β,7aα,8aβ)]8a-[[(2R,6R)-(4-(1,1-dimethylethyl)-6-methyl-morpholin-2-yl)]-oxymethyl]-4-(1,3-dioxolan-2-yl)-4,4a,5,6,7,7a,8,8a-octahydro-7-methyl-3-(1-methylethyl)-1,4-methano-s-indacene-3a(1H)-carboxylic acid, diphenylmethyl ester

Intermediate 4f

[1R-(1α,3aβ,4β,4aβ,7β,7aα,8aβ)]8a-[(2R,6R)-(4-propyl-6-methyl-morpholin-2-yl)-oxymethyl]-4-(1,3-dioxolan-2-yl)-4,4a,5,6,7,7a,8,8a-octahydro-7-methyl-3-(1-methylethyl)-1,4-methano-s-indacene-3a(1H)-carboxylic acid

Intermediate 4 g

[1R-(1α,3aβ,4β,4aβ,7β,7aα,8aβ)]8a-[(2R,6R)-(4,6-dimethyl-morpholin-2-yl)-oxymethyl]-4-(1,3-dioxolan-2-yl)-4,4a ,5,6,7,7a,8,8a-octahydro-7-methyl-3-(1-methylethyl)-1,4-methano-s-indacene-3a(1H)-carboxylic acid, diphenylmethyl ester For the preparation of this intermediate which involves methylamine, a slightly different experimental procedure was followed. The methylamine was released "in situ" from its hydrochloride salt (3 eq) and triethylamine (4 eq). Also no acetic acid was used in this particular reaction.

Intermediate 4h

[1R-(1α,3aβ,4β,4aβ,7β,7aα,8aβ)]8a-[(2R,6R)-(6-methyl-4-phenyl-morpholin-2-yl)-oxymethyl]-4-(1,3-dioxolan-2-yl)-4,4a,5,6,7,7a, 8,8a-octahydro-7-methyl-3-(1-methylethyl)-1,4-methano-s-indacene-3a(1H)-carboxylic acid, diphenylmethyl ester

Intermediate 4i

[1R-(1α,3aβ,4β,4aβ,7β,7aα,8aβ)]8a-[(2R,6R)-(4-benzyl-6-methylmorpholin-2-yl)-oxymethyl]-4-(1,3-dioxolan-2-yl)-4,4a,5,6,7,7a,8,8a-octahydro-7-methyl-3-(1-methylethyl)-1,4-methano-s-indacene-3a(1H)-carboxylic acid, diphenylmethylester

Intermediate 4j

[1R-(1α,3aβ,4β,4aβ,7β,7aα,8aβ)]8a-[(2R,6R)-(4-(2-ethylthioethyl)-6-methylmorpholin-2-yl)-oxymethyl]-4-(1,3-dioxolan-2-yl)-4,4a,5,6,7,7a,8,8a-octahydro-7-methyl-3-(1-methylethyl)-1,4-methano-s-indacene-3a(1H)-carboxylic acid, diphenylmethyl ester

Intermediate 5

[1R-(1α,3aβ,4β,4aβ,7β,7aα,8aβ)]4-formyl-8a-[((2R,4R)4-methyl-3-oxa-pentanedial-2-yl)oxymethyl]-4,4a,5,6,7,7a,8,8a-octahydro-7-methyl-3-(1-methylethyl)-1,4-methano-s-indacene-3a(1H)-carboxylic acid In a 4 l vessel were placed water (1100 ml), 1N NaOH (125.5 ml) and [1R-(1α,3aβ,4β,4aβ,7β,7aα,8aβ]-4-formyl-8a-[(6-deoxy-β-D-mannopyranosyloxy)methyl]-4,4a,5,6,7,7a,8,8a-octahydro-7-methyl-3-(1-methylethyl)-1,4-methano-s-indacene-3a(1H)-carboxylic acid (60 g). Once the material was almost dissolved, solid NaHCO$_3$ (31.6 g) was added at once and the mixture was stirred until a clear solution is obtained. To this solution was added at 25° C. a solution of NaIO$_4$ (67.2 g) in water (600 ml) over a period of 3 h. After stirring for 2 h at 25° C., the cloudy suspension was filtered-off and the new clear solution was poured into the vessel and 2N HCl (250 ml) was added dropwise until pH=1.61.

The solid precipitated was filtered-off, washed with water (1000 ml) and dried under vacuum overnight (40° C.). The title compound 52 g was obtained as a white powder. The filtrate was extracted with ethyl acetate (500 ml) and the organic layer washed with brine (100 ml), dried over Na$_2$SO$_4$ and concentrated to dryness. Removal of the solvent under vacuum gave an additional amount of the title compound 5 g as a yellowish foam.

The title compound was also prepared using the above procedure but using [1R-(1α,3aβ,4β,4aβ,7β,7aα,8aβ)]-4-formyl-8a[[(6-deoxy-β-D-altropyranosyloxy-methyl]-4,4a,5,6,7,7a,8,8a-octahydro-7-methyl-3-(1-methylethyl)-1,4methano-s-indacene-3α(1H)-carboxylic acid as starting material.

Intermediate 6

[1R-(1α,3aβ,4β,4aβ,7β,7aα,8aβ)]-4-(1,3-dioxolan-2-yl)-8a-[(2R,6R)-(6-Methyl-morpholin-2-yl)-oxymethyl]-4,4a,5,6,7,7a,8,8a-octahydro-7-methyl-3-(1-methylethyl)-1,4-methano-s-indacene-3a(1H)-carboxylic acid, ammonium salt To a solution of intermediate 3 (200 mg) in 20 mL of a solution of ammonia in methanol (0.1M), palladium (10%) on charcoal was added (10 mg) under nitrogen. The mixture was shaken in a Parr apparatus (50 p.s.i.) for 24 h. The reaction was filtered and the solvent evaporated to dryness. The residue was purified by flash column chromatography on silica gel eluting with dichloromethane:methanol 20:1 to give the title compound (131 mg) as a white solid.

$^1$H-NMR (CDCl$_3$, ppm): 5.95 (dd, 1H, H-2, J=1.2 and 3.3 Hz),4.62 (s, 1H, OCH$_2$O), 4.33 (dd, 1H, H-2', J=2.4 and 8.7 Hz), 4.09 (d, 1H, 8aCH$_a$, J=9.6 Hz), 4.13–4.05, 4.03–3.94 and 3.85–3.81 (3 m, 4H, OCH$_2$CH$_2$O), 3.69 (d, 1H, 8aCH$_b$, J=9.6 Hz), 3.62 (m, 1H, H-6'), 2.91 (dd, 1H, H$_a$-3', J=2.1 and 12.0 Hz), 2.74 (dd, 1H$_a$-5', J=2.1 and 12.3 Hz), 2.65 (t, 1H, H-1, J=3.9 Hz), 2.46 (dd, 1H, H$_b$-3', J=9.0 and 12.0 Hz), 2.40 (dd, 1H, H$_b$-5', J=10.2 and 12.3 Hz), 2.32 (m, 1H, CH(CH$_3$)$_2$).

Intermediate 7

1R-(1α,3aβ,4β,4aβ,7β,7aα,8aβ)]-4-(1,3-Dioxolan-2-yl)-8a-[(2R,6R)-(4-(2-bromoallyl)-6-methyl-morpholin-2-yl)-oxymethyl]-4,4a,5,6,7,7a, 8,8a-octahydro-7-methyl-3-(1-methylethyl)-1,4-methano-s-indacene-3a(1H)-carboxylic acid A mixture of Intermediate 6 (500 mg), 2-bromoallyl bromide (203 mg) and solid sodium bicarbonate (170 mg) in absolute ethanol (15 ml) was stirred at 60° C. for 5 hours. After cooling and removal of the solvent, the residue was purified by column chromatography using 1% methanol in dichloromethane as eluent to give the title compound (481 mg).

$^1$H-NMR (CDCl$_3$, ppm): 11.30 (br s, 1H, CO$_2$H), 5.97 (dd, 1H, H-2, J=1.5 and 3.6 Hz), 5.84 (m, 1H, CH$_2$=), 5.92 (m, 1H, CH$_2$=), 4.59 (s, 1H, OCHO), 4.44 (dd, 1H, H-2', J=2.4 and 8.7 Hz), 4.14 (d, 1H, 8a-CH$_2$, J=9.6 Hz), 4.12 to 3.80 (m, 4H, OCH$_2$CH$_2$O), 3.70 (m, 2H, H-6' and 8a-CH$_2$), 3.16 (s, 2H, allyl-CH$_2$—N), 2.82 (m, 1H, CH—N), 2.66(m, 1H, H-1),2.64 (m, 1H, CH—N)

Intermediate 8

[1R-(1α,3aβ,4β,4aβ,7β,7aα,8aβ)]-4-(1,3-Dioxolan-2-yl)-8a-[(2R,6R)-(4-(2-chloroallyl)-6-methyl-morpholin-2-yl)-oxymethyl]-4,4a,5,6,7,7a,8, 8a-octahydro-7-methyl-3-(1-methylethyl)-1,4-methano-s-indacene-3a(1H)-carboxylic acid A mixture of Intermediate 6 (1.6 g), 2-chloroallyl chloride (0.300 ml) and solid sodium bicarbonate (0.550 g) in absolute ethanol (100 ml) was stirred at reflux for 2 hours. After cooling, solid sodium iodide (0.040 g; 0.5 mmol) was added and the mixture was refluxed again for 20 hours. After cooling and evaporation, the residue was purified by column chromatography using 2% methanol in dichloromethane as eluent to give the title compound (0.880 g).

$^1$H-NMR (CDCl$_3$, ppm): 11.60 (br s, 1H, CO$_2$H), 5.97 (dd, 1H, H-2, J=1.5 and J=3.4 Hz), 5.38 (m, 1H, CH$_2$=), 5.35 (m, 1H, CH$_2$=), 4.59 (s, 1H, OCHO), 4.44 (dd, 1H, H-2', J=2.4 and J=8.6 Hz), 4.14 (d, 1H, 8a-CH$_2$, J=9.6 Hz), 4.12 to 3.80 (m, 4H, OCH$_2$CH$_2$O), 3.70 (m, 2H, H-6' and 8a-CH$_2$), 3.12 (s, 2H, allyl-CH$_2$—N, 2.83 (m, 1H, CH—N), 2.66 (m, 1H, H-1), 2.66 (m, 1H, CH—N), 2.30 (m, 1H, CH(CH$_3$)$_2$).

Intermediate 9

[1R-(1α,3aβ,4β,4aβ,7β,7aα,8aβ)]-4-(1,3-Dioxolan-2-yl)-8a-[(2R,6R)-(4-(3,3-difluoroallyl)-6-methyl-morpholin-2-yl)-oxymethyl]-4,4a,5,6,7,7a,8, 8octahydro-7-methyl-3-(1-methylethyl)-1,4-methano-s-indacene-3a(1H)-carboxylic acid A mixture of Intermediate 6 (500 mg), 3-bromo-3,3-difluoropropene (157 mg) and solid sodium bicarbonate (170 mg) in absolute ethanol (20 ml) is stirred at 70° C. for 24 hours. After cooling and removal of the solvent, residue was purified by column chromatography using 5% methanol in dichloromethane as eluent to. give the title compound (304 mg).

$^1$H-NMR (CDCl$_3$, ppm): 11.50 (br s, 1H, CO$_2$H), 5.96 (dd, 1H, H-2, J=1.2 and 3.3 Hz), 4.60 (s, 1H, OCHO), 4.38 (dd, 1H, H-2', J=2.4 and 8.4 Hz), 4.25 (dddd, 1H, CH=, J=25, 10.5, 8.1 and 2.4 Hz), 4.15 to 3.80 (m, 5H, 8a-CH$_2$ and OCH$_2$CH$_2$O), 3.70 (d, 1H, 8a-CH$_2$, J=9.6 Hz), 3.64 (m, 1H, H-6'), 3.02 (m, 2H, allyl-CH$_2$—-N), 2.80 (m, 1H, CH—N), 2.70 (m, 1H, H-1), 2.61 (m, 1H, CH—N)

Intermediate 10

N-Methyl-N-[(2R)-hydroxy-propyl]-2-amino-acetaldehyde, dimethyl acetal

N-Methylaminoacetaldehyde dimethyl acetal (1,41 ml) and R-(-)-propylene oxide (1 ml) were dissolved in dry ethanol (10 ml); the mixture was stirred at room temperature for 72 hours. The reaction mixture was concentrated to dryness and the residue was purified by column chromatography (dichloromethane/methanol v/v 7:1) to give the title compound (1,706 g).

$^1$H-NMR (CDCl$_3$, ppm): 4.46 (dd, 1H, CH—(OMe)$_2$, J=4.8 and 6.0 Hz); 3.82–3.70 (m, 1H, CH—OH); 3.5 (bs, 1H, OH); 3.36 (s, 6H, 2(CH$_3$—O)); 2.66 (dd, 1H, CH$_2$—CH—(OMe)$_2$, J=6.0 and 13.5 Hz); 2.53 (dd, 1H, CH$_2$—CH—(OMe)$_2$, J=6.3 and 13.5 Hz); 2.39 (dd, 1H, CH$_2$—CH—OH, J=3 and 12.6 Hz); 2.36 (s, 3H, CH$_3$—N); 2.27 (dd, 1H, CH$_2$—CH—OH, J=10.2 and 12.6 Hz); 1.11 (d, 3H, CH$_3$—CH, J=6.0 Hz).

Intermediate 11

6R4,6-dimethyl-2-hydroxy-morpholine

Intermediate 10 (1,7 g, 10,6 mmol) and 6N HCl (20 ml) were stirred in a flask submerged into an oil bath at 90° C. for 2 hours. The mixture was cooled down to room temperature and neutralized using solid NaOH (4,8 g); Ethanol (600 ml) was added and a white precipitate of sodium chloride was formed. The precipitate was filtered under vacuum and the filtrate was concentrated to dryness under vacuum with the help of toluene. The resulting syrup was purified by column chromatography (dichloromethane/methanol v/v from 10:1 to 1:1) to give the title compound (760 mg).

$^1$H-NMR (CDCl$_3$, ppm):(α:β≈1:2 mixture) 5.11 (bs, 1Hα, H2); 4.87 (dd, 1Hβ, H2, J=2.4 and 8.7 Hz); 4.23–4.16 (m, 1Hα, H6); 3.82–3.66 (m, 1Hβ, H6); 2.91 (dt, 1Hβ, H3eq, J=1.8 and 10.8 Hz); 2.79–2.73 (m, 2Hα, H3eq+H5eq); 2.63 (dt, 1Hβ, H5eq, J=1.8 and 11.1 Hz); 2.28 (s, 3Hβ, CH$_3$—N); 2.24 (s, 3Hα, CH$_3$—N); 2.18 (dd, 1Hα, H3ax, J=2.4 and 11.1 Hz); 1.83–1.68 (m, 2Hβ+1Hα, H3ax+H5ax+H5ax); 1.19 (d, 3Hβ, CH$_3$CH, J=6.3 Hz); 1.13 (d, 3Hα, CH$_3$CH, J=6.3 Hz).

Intermediate 12

[1R-(1α,3aβ,4β,4aβ,7β,7aα,8aβ)]8a-Trifluoromethanesulphonyloxymethyl-4-formyl-4,4a,5,6,7,7a,8,8a-octahydro-7-methyl-3-(1-methylethyl)-1,4-methano-s-indacene-3a(1H)-carboxylic acid, benzyl ester A mixture of benzyl sordaricin (423,5 mg), pyridine (118 ml), Cs$_2$CO$_3$ (catalytic) and 3 Å molecular sieves in dichloromethane (10 ml) under argon was cooled down to –20° C. and trifluoromethanesulphonic anhydride (231 ml) was slowly added. The mixture was stirred at –20° C. for 30 minutes. Hexane (30 ml) was added, the mixture was stirred for 15 minutes, filtered through Celite, washed with 1% H$_2$SO$_4$, water, dried over Na$_2$SO$_4$ and concentrated to dryness. The title compound is obtained as a syrup which is very unstable but it can be kept in hexane for a reasonable period of time (some hours or even days in the refrigerator). It is used without further purification.

$^1$H-NMR (CDCl$_3$, ppm): 9.71 (s, 1H, CHO); 7.4–7.3 (m, 5H, Ph); 6.11 (dd, 1H, H2, J=1.5 and 3.6 Hz); 5.3–5.1 (m, 2H, CH$_2$Ph); 4.78 (d, 1H, 8aCHa, J=9.6 Hz); 4.62 (d, 1H, 8aCHb, J=9.6 Hz); 2.76 (t, 1H, H1, J=4.5 Hz); 2.22 (m, 1H, CH—(CH$_3$)$_2$).

Intermediate 13

[1R-(1α,3aβ,4β,4aβ,7β,7aα,8aβ]8a-[(2R,6R)-(4,6-Dimethyl-morpholin-2-yl)-oxymethyl]-4-formyl-4,4a,5,6,7,7a,8,8a-octahydro-7-methyl-3-(1-methylethyl)-1,4-methano-s-indacene-3a(1H)-carboxylic acid, benzyl ester Intermediate 12 (crude of 1 mmol) dissolved in dichloromethane (8 ml) was added to a mixture containing Intermediate 11 (132 mg), Cs$_2$CO$_3$ (400 mg), tetrabutylammonium triftuoromethanesulphonate (40 mg) and 3 Å molecular sieves in CH$_2$Cl$_2$ (7 ml). The resulting mixture was stirred at room temperature for 20 hours following the reaction evolution by t.l.c. (hexane/acetone v/v 4:1); then, it was filtered through Celite and directly purified by column chromatography (hexane/acetone v/v 7:1). The title compound (174 mg) was obtained as a colourless syrup.

$^1$H-NMR (CDCl$_3$, ppm): 9.71 (s, 1H, CHO); 7.42–7.25 (m, 5H, Ph); 6.35 (dd, 1H, H2, J=1.5 and 3.6 Hz); 5.3–5.1 (m, 2H, CH$\underline{2}$Ph); 4.35 (dd, 1H, H2', J=2.1 and 9.0 Hz); 3.93 (d, 1H, 8aCHa, J=9.6 Hz); 3.7–3.6 (m, 1H, H6'); 3.67 (d, 1H, 8aCHb, J=9.6 Hz); 2.80–2.71 (m, 1H, H3'); 2.73 (t, 1H, H1, J=4.2 Hz); 2.6 (dt, 1H, H5', J=1.5 and 11.1 Hz); 2.26 (s, 3H, CH$_3$—N); 2.23 (m, 1H, C$\underline{H}$—(CH$_3$)$_2$).

Intermediate 14

[1R-(1α,3aβ,4β,4aβ,7β,7aα,8aβ)]8a-[(2R,6R)-6-methyl-morpholin-2-yl)-oxymethyl]-4-(1,3-dioxolan-2-yl)-4,4a,5,6,7,7a,8,8a-octahydro-7-methyl-3-(1-methylethyl)-1,4-methano-s-indacene-3a(1H)-carboxylic acid In a well dried (90° C., N$_2$, 60 min) 10 L jacketed vessel was placed dry acetonitrile (1.4 L). Intermediate 5 (90 g) was added portionwise followed by ethyleneglycole (108 ml), trimethylorthoformate (52.2 ml) and p-toluenesulfonic acid monohydrate (1.8 g). The temperature was set to 25° C. and, after 30 minutes of stirring, solid benzotriazole (48.42 g) and 25% aqueous ammonium hydroxide (1400 ml) were added concurrently over a period of 5 minutes. The mixture was stirred at 25° C. for 2 hours then cooled down to 5° C. Solid sodium borohydride (18 g) was added and the mixture stirred at 5° C. for 1 hour then allowed to warm to 25° C. and kept under these conditions overnight. The solvent was removed at 50° C. under nitrogen until a volume=1800 ml, then cooled down to 25° C.

2N Hydrochloric acid was added carefully until pH=8 and the resulting precipitate filtered with suction, washed with a mixture water/acetonitrile v/v 2:1 and dried at the vacuum oven (40° C.) for 24 hours to give the title compound (70 g) as a white powder.

$^1$H-NMR (δ, ppm, CDCl$_3$): 5.95 (dd, 1H, H2, J=1.5 and 3.6 Hz), 4.61 (s, 1H, OCHO), 4.32 (dd, 1H, H2', J=2.4 and 9 Hz), 4.15–3.92 and 3.86–3.80 (2m, 5H, 8aCH$_2$+OCH$_2$CH$_2$O), 3.69 (d, 1H, 8aCH$_2$, J=9.3 Hz), 3.60 (m, 1H, H6'), 2.90 (bd, 1H, H3', J=2.1 and 12 Hz), 2.73 (bd, 1H, H5', J=2.4 and 12.3 Hz), 2.52–2.26 (m, 3H, 2H5'+CH(CH$_3$)$_2$).

Intermediate 15

[1R-(1α,3aβ,4β,4aβ,7β,7aα,8aβ)]8a-[(2R,6R)-6-methyl-morpholin-2-yl)-oxymethyl]-4-formyl-4,4a,5,6,7,7a,8,8a-octahydro-7-methyl-3-(1-methylethyl)-1,4-methano-s-indacene-3a(1H)-carboxylic acid In a 4L jacketed reactor was placed tetrahydrofuran (600 ml). Intermediate 14 (48.5 g) was added portionwise at 25° C. and to the suspension obtained 1N HCl (300 ml) was added dropwise over a period of 10 minutes.

The solution was stirred at 25° C. until completion (TLC controls/dichloromethane/methanol v/v 10:1), then 1N NOH was added until all the material was dissolved (aprox. 500 ml).

The temperature was set to 55° C. and the tetrahydrofuran removed under nitrogen. Once a final volume=900 ml was obtained, the mixture was cooled down and acidified by slow addition of hydrochloric acid until pH=7.7.

The white precipitate was collected by filtration, washed with water, dried at the vacuum oven (40° C.) to afford the title compound (35 g) as a white powder.

$^1$H-NMR (δ, ppm, CDCl$_3$): 9.59 (s, 1H, CHO), 5.96 (bd, 1H, H2, J=2.4 Hz), 4.63 (bd, 1H, H2', J=9.3 Hz), 4.08 (bm, 1H, H6'), 3.88 and 3.79 (2bd, 2H, 8aCH$_2$, J=8.1 Hz), 2.94 and 2.83 (2bd, 2H, H3'+H5', J=10.5 Hz), 2.61 (bt, 1H, H1, J=3.6 Hz).

Intermediate 16

[1R-(1α,3aβ,4β,4aβ,7β,7aα,8aβ)]8a-[(2R,6R)-6-methyl4-(2-methyl-2-propenyl)-morpholin-2-yl)-oxymethyl]-4-(1,3-dioxolan-2-yl)-4,4a,5,6,7,7a,8,8a-octahydro-7-methyl-3-(1-methylethyl)-1,4-methano-s-indacene-3a(1H)-carboxylic acid In a 2 L jacketed reactor was placed commercial acetonitrile (232 ml) and Intermediate 14 (20 g) was added portionwise onto it. The jacket temperature was set to 25° C. and sodium hydroxide (4.2 g in 225 ml of water) was added dropwise over a period of 5 minutes. Once all the material was disolved a solution of 3-bromo-2-methylpropene (5.44 ml) in commercial acetonitrile (20 ml) was added over a period of 5 minutes.

After stirring for 2 hours, hexane (200 ml) was added and the two layers partitioned. The acetonitrile/water layer was washed twice (2×200 ml) with hexane and the hexane layer back extracted with 0.25 N sodium hydroxide (200 ml).

The combined aqueous layers were concentrated at 60° C. under nitrogen until a volume of 450 ml aprox., then cooled down to 25° C.

Slow addition of hydrochloric acid until pH=7.8 promoted the precipitation of a white solid which was collected by filtration, washed with water (1 L), and dried with suction overnight to give the title compound (18.1 g) as a white powder.

$^1$H-NMR (δ, ppm, CDCl$_3$): 7.26 (s, 1H, CHO), 5.95 (dd, 1H, H2', J=1.2 and 3.6 Hz), 4.86 (bs, 2H, =CH$_2$), 4.61 (s, 1H, OCHO), 4.40 (dd, 1H, H2', J=2.4 and 9 Hz), 4.15–3.9 and 3.83 (m, 5H, 8aCH$_2$+OCH$_2$CH$_2$O), 3.70–3.60 (m, 2H, 8aCH$_2$+H6'), 2.84 (bs, 2H, NCH$_2$), 2.77 (bd, 1H, H3', J=10.8 Hz), 2.65 (bt, 1H, H1, J=3.6 Hz), 2.58 (bd, 1H, H5', J=11.1 Hz), 2.33 (m, 1H, CH(CH$_3$)$_2$), 1.73 (bs, 3H, =C—CH$_3$).

Intermediate 17

[1R-(1α,3aβ,4β,4aβ,7β,7aα,8aβ)]8a-[(2R,6R)-4-(4-methoxy benzyl)-6-methyl-morpholin-2-yl)-oxymethyl]-4-(1,3-dioxolan-2-yl)-4,4a,5,6,7,7a,8,8a-octahydro-7-methyl-3-(1-methylethyl)-1,4-methano-s-indacene-3a(1H)-carboxylic acid In a well dried 1 L round botton flask was placed at 25° C. dry acetonitrile (300 ml). Intermediate 5 (20 g) was added portionwise followed by ethyleneglycole (24 ml), trimethylorthoformate (11.76 ml) and p-toluene sulphonic acid monohydrate (400 mg). The solution was stirred at 25° C. for 30 minutes then solid benzotriazole (10.8 g) was added onto it.

This solution was poured into a 500 ml dropping funnel and it was slowly added dropwise onto a well dried 2 L jacketed reactor containing p-methoxybenzylamine (56 ml) and sodium borohydride (1 g) in dry acetonitrile (200 ml). Three additional portions of sodium borohydride (3×1 g) were added carefully over the addition of the first solution.

Once the addition was concluded, the mixture was stirred at room temperature overnight, then heated up to 60° C. and concentrated under nitrogen to a total volume=350 ml. 1N Hydrochloric acid was added until pH=8.00 and the whitish precipitate collected by filtration and washed with a mixture acetonitrile/H$_2$O v/v 2:1 (1 L). Drying in the vacuum oven (40° C.) overnight gave the title compound (18 g) as a white powder.

$^1$H-NMR (δ, ppm, CDCl$_3$): 7.20 (m, 2H, 2ArH), 6.85 (m, 2H, 2ArH), 5.93 (dd, 1H, H2, J=0.9 and 3.3 Hz), 4.59 (s, 1H, OCHO), 4.41 (dd, 1H, H2', J=2.1 and 8.4 Hz), 4.13–3.93 and 3.86–3.81 (2m, 5H, OCH$_2$CH$_2$O+8aCH$_2$), 3.80 (s, 3H, OCH$_3$), 3.67 (m, 2H, 8aCH$_2$+H6'), 3.43 (bs, 2H, NCH$_2$), 2.80 (bd, 1H, H3', J=10.5 Hz), 2.62 (m, 2H, H1+H5'), 2.29 (m, 1H, CH(CH$_3$)$_2$).

Intermediate 18

N-Methyl-N-[(2)-hydroxy-butyl]-2-amino-acetaldehyde, dimethyl acetal

N-Methylaminoacetaldehyde dimethyl acetal (6,42 ml) and 1,2-epoxybutane (8,7 ml) were dissolved in dry ethanol (50 ml); the mixture was stirred at room temperature for 30 hours. The reaction mixture was concentrated to dryness and the residue was purified by column chromatography (dichloromethane/methanol v/v from 20:1 to 10:1) to give the title compound (9 g).

$^1$H-NMR (CDCl$_3$, ppm): 4.50 (dd, 1H, C$\underline{H}$—(OMe)$_2$, J=5.1 and 6.0 Hz); 3.60–3.40 (m, 1H, C$\underline{H}$—OH); 3.36 (s, 3H, (C$\underline{H}_3$—O); 3.35 (s, 3H, (C$\underline{H}_3$—O)); 2.65 (dd, 1H, C$\underline{H}_2$—CH—(OMe)$_2$, J=5.7 and 13.5 Hz); 2.50 (dd, 1H, C$\underline{H}_2$—CH—(OMe)$_2$, J=4.8 and 13.5 Hz); 2.40 (dd, 1H, C$\underline{H}_2$—CH—OH, J=3.0 and 12.3 Hz); 2.35 (s, 3H, C$\underline{H}_3$—N); 2.28 (dd, 1H, C$\underline{H}_2$—CH—OH, J=10.5 and 12.6 Hz); 1.54–1.30 (m, 2H, CH$_3$—C$\underline{H}_2$—CH—OH); 0.96 (t, 3H, C$\underline{H}_3$—CH$_2$, J=6.9 Hz).

Intermediate 19

4-methyl-6-ethyl-2-hydroxy-morpholine

Intermediate 18 (4,78 g) and 6N hydrochloric acid (41,6 ml) were stirred in a flask submerged into an oil bath at 90° C. for 6 hours. The mixture was cooled down to room temperature and neutralized using solid sodium hydroxide (10 g); Ethanol (500 ml) was added and a white precipitate of sodium chloride was formed. The precipitate was filtered under vacuum and the filtrate was concentrated to dryness under vacuum with the help of toluene. The resulting syrup was purified by column chromatography (dichloromethane/methanol v/v from 20:1 to 5:1) to give the title compound (2,9 g).

$^1$H-NMR (CDCl$_3$ ppm):(1:1 mixture)
5.11 (bs) and 4.86 (dd, J=2.4 and 8.4 Hz), H2.

Intermediate 20

[1R-(1α,3aβ,4β,4aβ,7β,7aα,8aβ)]8a-[(2R)-(4-methyl-6-ethyl-morpholin-2-yl)-oxymethyl]-4-formyl-4,4a,5,6,7,7a,8,8a-octahydro-7-methyl-3-(1-methylethyl)-1,4-methano-s-indacene-3a(1H)-carboxylic acid benzyl ester Intermediate 12 (crude of 1 mmol) dissolved in dichloromethane (15 ml) was added to a mixture containing Intermediate 19 (145 mg), cesium carbonate (400 mg), tetrabutylammonium trifluoromethanesulphonate (40 mg) and 3 Å molecular sieves in dichloromethane (5 ml). The resulting mixture was stirred at room temperature for 44 hours following the reaction evolution by t.l.c. (hexane/ethyl acetate v/v 5:1); then, it was filtered through Celite and directly purified by column chromatography (hexane/ethyl acetate v/v from 7:1 to 1:1). The title compound (165 mg) was obtained as a colourless syrup.

$^1$H-NMR (CDCl$_3$, ppm): 9.72 and 9.66 (s, 1H, CHO); 7.42–7.25 (m, 10H, Ph); 6.09 and 6.04 (dd, 1H, H2, J=1.3 and 3.3 Hz); 5.3–5.1 (m, 4H, C$\underline{H}_2$Ph); 4.39 and 4.35 (dd, 1H, H2', J=2.1 and 8.7 Hz); 4.16 and 3.89 (d, 1H, 8aCHa, J=9.6 Hz); 3.72 and 3.50 (d, 1H, 8aCHb, J=9.6 Hz); 3.46–3.34 (m, 2H, H6'); 2.84–2.58 (m, 6H, H3'+H1+H5'); 2.27 (s, 6H, C$\underline{H}_3$—N).

Intermediate 21

4-Methyl-6-tert-butyl-2-hydroxy-morpholine

N-Methylaminoacetaldehyde dimethyl acetal (3,4 ml) and 3,3-dimethyl-1,2-epoxybutane (4,04 ml) were dissolved in dry ethanol (30 ml); the mixture was stirred at room temperature for 40 hours and then 40 hours at 80° C. The reaction mixture was concentrated to dryness and the residue was mixed with 6N hydrochloric acid (50 ml) and the resulting mixture was stirred in a flask submerged into an oil bath at 80° C. for 8 hours. The mixture was cooled down to room temperature and neutralized using solid sodium hydroxide (12 g); Ethanol (500 ml) was added and a white precipitate of sodium chloride was formed. The precipitate was filtered under vacuum and the filtrate was concentrated to dryness under vacuum with the help of toluene. The resulting syrup was purified by column chromatography (dichloromethane/methanol v/v from 25:1 to 10:1) to give the title compound (3 g).

$^1$H-NMR (CDCl$_3$, ppm): (1:2 mixture) 5.12 (bs) and 4.83 (dd, J=2.4 and 8.4 Hz), H2.

Intermediate 22

[1R-(1α,3aβ,4β,4aβ,7β,7aα,8aβ)]8a-[(2R)-(4-methyl-6-tert-butyl-morpholin-2-yl)-oxymethyl]-4-formyl-4,4a,5,6,7, 7a,8, 8a-octahydro-7-methyl-3-(1-methylethyl)-1,4-methano-s-indacene-3a(1H)-carboxylic acid benzyl ester Intermediate 12 (crude of 1 mmol) dissolved in toluene (10 ml) was added to a mixture containing Intermediate 21 (173 mg), cesium carbonate (400 mg), tetrabutylammonium trifluoromethanesulphonate (40 mg) and 3 Å molecular sieves in toluene (5 ml). The resulting mixture was stirred at room temperature for 20 hours following the reaction evolution by t.l.c. (hexanelacetone V/V 4:1); then, dichloromethane (15 ml) was added and the reaction mixture was stirred at room temperature 96 hours; the reaction crude was filtered through Celite and directly purified by column chromatography (hexanelethyl acetate v/v from 5:1 to 1:1). The title compound (74 mg) was obtained as a colourless syrup.

$^1$H-NMR (CDCl$_3$, ppm): 9.72 and 9.67 (s, 1H, CHO); 7.42–7.25 (m, 10H, Ph); 6.09 and 6.04 (dd, 1H, H2, J=1.5 and 3.6 Hz); 5.3–5.1 (m, 4H, C$\underline{H}_2$Ph); 4.37 and 4.34 (dd, 1H, H2', J=2.4 and 8.4 Hz); 4.15 and 3.84 (d, 1H, 8aCHa, J=9.6 Hz); 3.77 and 3.48 (d, 1H, 8aCHb, J=9.6 Hz); 3.14 and 3.10 (t, 1H, H1, J=2.1 Hz); 2.80–2.58 (m, 4H, H3'+H5'); 2.27 (s, 6H, C$\underline{H}_3$—N).

Intermediate 23

N-Methyl-N-[(2)-hydroxy-2-phenyl-ethyl]-2-amino-acetaldehyde, dimethyl acetal

N-Methylaminoacetaldehyde dimethyl acetal (3,21 ml) and styrene oxide (3,57 ml) were dissolved in dry ethanol (30 ml); the mixture was stirred at room temperature for 72 hours. The reaction mixture was concentrated to dryness and the residue was purified by column chromatography (dichloromethane/methanol v/V from 1:0 to 10:1) to give the title compound (5,6 g).

$^1$H-NMR (CDCl$_3$, ppm): 7.40–7.15 (m, 5H, Ph); 4.68 (dd, 1H, CH—(OMe)$_2$, J=3.6 and 10.5 Hz); 4.51 (t, 1H, CH—OH, J=5.1 Hz); 3.40 (s, 3H, (CH$_3$—O); 3.38 (s, 3H, (CH$_3$—O)); 2.75 (dd, 1H, CH$_2$—CH—(OMe)$_2$, J=5.7 and 13.5 Hz); 2.70–2.40 (m, 3H, CH$_2$—CH—(OMe)$_2$ +CH$_2$—CH—OH); 2.45 (s, 3H, CH$_3$—N).

Intermediate 24

4-methyl-6-phenyl-2-hydroxy-morpholine

Intermediate 23 (5,40 g) and 6N hydrochloric acid (50 ml) were stirred in a flask submerged into an oil bath at 90° C. for 20 hours. The mixture was cooled down to room temperature and neutralized using solid sodium hydroxide (12 g); Ethanol (700 ml) was added and a white precipitate of sodium chloride was formed. The precipitate was filtered under vacuum and the filtrate was concentrated to dryness under vacuum with the help of toluene. The resulting syrup was purified by column chromatography (dichloromethane/methanol v/v from 30:1 to 10:1) to give the title compound (1,9 g).

$^1$H-NMR (CDCl$_3$, ppm): (1:4 mixture) 5.67 (m) and 5.17 (dd, J=2.4 and 10.5 Hz), H2.

Intermediate 25

[1R-(1α,3aβ,4β,4aβ,7β,7aα,8aβ)]8a-[(2R)-(4-methyl-6-phenyl-morpholin-2-yl)-oxymethyl]-4-formyl-4,4a,5,6,7,7a,8,8a-octahydro-7-methyl-3-(1-methylethyl)-1,4-methano-s-indacene-3a(1H)-carboxylic acid benzyl ester Intermediate 12 (crude of 1 mmol) dissolved in toluene (10 ml) was added to a mixture containing Intermediate 24 (193 mg), cesium carbonate (400 mg), tetrabutylammonium trifluoromethanesulphonate (40 mg) and 3 Å molecular sieves in toluene (5 ml). The resulting mixture was stirred at room temperature for 96 hours and 20 hours at 80° C. following the reaction evolution by t.l.c. (hexane/acetone v/v 4:1); then, the reaction crude was filtered through Celite and directly purified by column chromatography (hexane/ethyl acetate v/v from 2:1 to 1:1). The title compound (115 mg) was obtained as a colourless syrup.

$^1$H-NMR (CDCl$_3$, ppm): 9.72 and 9.68 (s, 1H, CHO); 7.40–7.20 (m, 20H, Ph); 6.09 and 6.06 (dd, 1H, H2, J=1.5 and 3.6 Hz); 5.25–5.05 (m, 4H, CH$_2$Ph); 4.80–4.50 (m, 4H, H6'+H2'); 4.20 and 3.97 (d, 1H, 8aCHa, J=9.6 Hz); 3.76 and 3.55 (d, 1H, 8aCHb, J=9.6 Hz); 3.00–2.70 (m, 6H, H3'+H1+H5'); 2.31 (s, 6H, CH$_3$—N).

Intermediate 26

1-O-(p-toluenesulfonyl)-2-methylene-1,3-propanediol

2-Methylene-1,3-propanediol (480 mg) and dibutyltinoxide (1,7 g) were dissolved in toluene (30 ml) and the resulting suspension was refluxed for 1 hour eliminating water with the help of a Dean-Stark apparatus. The flask was cooled down to room temperature and then, N-methyl-imidazol (797 ml) and tosyl chloride (1,56 g) were added. After 15 minutes stirring, the reaction crude was directly purified by column chromatography (hexane-ethyl acetate v/v from 7:1 to 1:1). The title compound (428 mg) was obtained as a white solid.

$^1$H-NMR (δ, CDCl$_3$): 7.80 (d, 2H, J=8.1 Hz, aromatic); 7.35 (d, 2H, J=8.1 Hz, aromatic); 5.30–5.19 (m, 2H, H—C=); 4.59 (s, 2H, CH$_2$—OTs); 4.13 (s, 2H, CH$_2$—OH); 2.45 (s, 3H, CH$_3$).

Intermediate 27

1-O-(p-toluenesulfonyl)-2-methylene-3-fluoro-propanol

Intermediate 26 (429 mg) was dissolved in dichloromethane and the resulting solution was cooled down to 0° C. DAST (343 μl) was added and the reaction mixture was stirred at room temperature for 1 hour following the reaction course by t.l.c. (hexaneethyl acetate v/v 3:1). Methanol was added and the crude was purified by column chromatography (hexane-ethyl acetate v/v from 10:1 to 5:1) to obtain the title compound (325 mg).

$^1$H-NMR (δ, CDCl$_3$): 7.80 (d, 2H, J=8.1 Hz, aromatic); 7.36 (d, 2H, J=8.1 Hz, aromatic); 5.36–5.30 (m, 2H, H—C=); 4.81 (d, 2H, J=46.8 Hz, CH$_2$—F); 4.58 (s, 2H, CH$_2$—OTs); 2.46 (s, 3H, CH$_3$).

Intermediate 28

[1R-(1α,3aβ,4β,4aβ,7β,7aβ,8aβ)]8a-[(2R,6R)-6-methyl-morpholin-2-yl]-oxymethyl]-4-formyl-4,4a,5,6,7,7a,8,8a-octahydro-7-methyl-3-(l1-methylethyl)-1,4-methano-s-indacene-3a(1H)-carboxylic acid, diphenylmethyl ester Intermediate 15 (1.38 g) was dissolved in dichloromethane (50 ml) and 0.346 M diphenyldiazomethane in dichloromethane (50 ml) was slowly added. The reaction mixture was stirred at room temperature for 16 hours. 1N hydrochloric acid (50 ml) was added to the reaction crude and, after 30 minutes stirring, the former purple solution became a yellow one. The organic layer was taken, dried over sodium sulphate and concentrated to dryness. The residue was purified by column chromatography (first, hexane-ethyl acetate v/v 1:1; then, dichloromethane-metanol v/v 10:1) and the title compound (1.48 g) was obtained.

$^1$H-NMR (δ, CDCl$_3$): 9.71 (s, 1H, CHO); 7.45–7.25 (m, 10H, aromatic); 6.06 (dd, 1H, J=1.5 and 3.6 Hz, H2); 4.68 (dd, 1H, J=2.1 and 9.3 Hz, H2'); 4.08 (d, 1H, J=9.0 Hz, 8aCH$_2$); 4.05–3.95 (m, 1H, H6'); 3.73 (d, 1H, J=9.0 Hz, 8aCH$_2$); 3.30–3.10 (m, 2H, H3'+H5'); 2.70 (t, 1H, J=3.9 Hz, H1).

Intermediate 29

[1R-(1α,3aβ,4β,4aβ,7β,7aβ,8aβ)]8a-[(2R,6R)-6-methyl-4-(2-fluoromethyl-2-propenyl)-morpholin-2-yl]-oxymethyl]-4-formyl-4,4a,5,6,7,7a,8,8a-octahydro-7-methyl-3-(1-methylethyl)-1,4-methano-s-indacene-3a (1H)-carboxylic acid, diphenylmethyl ester To a solution of Intermediate 28 (299 mg) in tetrahydrofuran (10 ml), 2N NaOH (1 mL) was added and the resulting solution was stirred at room temperature for 30 minutes. Intermediate 27 (244 mg) was added and the reaction mixture was stirred at 40° C. for 16 hours following the reaction course by t.l.c. (hexane-ethyl acetate v/v 3:1). The reaction crude was diluted with dichloromethane and brine was added. The organic layer was taken, dried over sodium sulphate and concentrated to dryness. Purification by column chromatography (hexane-ethyl acetate v/v 10:1) gave the title compound (244 mg).

$^1$H-NMR (δ, CDCl$_3$): 9.74 (s, 1H, CHO); 7.45–7.20 (m, 10H, aromatic); 6.06 (dd, 1H, J=1.5 and 3.6 Hz, H2); 5.25 (s, 1H, H—C=); 5.16 (s, 1H, H—C=); 4.86 (d, 2H, J=47.4 Hz, CH$_2$—F); 4.35 (dd, 1H, J=2.4 and 8.7 Hz, H2'); 4.07 (d, 1H, J=9.3 Hz, 8aCH$_2$); 3.71 (d, 1H, J=9.0 Hz, 8aCH$_2$); 3.68–3.60 (m, 1H, H6'); 2.98 (s, 2H, CH$_2$—N); 2.81–2.58 (m, 3H, H1+H3'+H5').

Intermediate 30

[1R-(1α,3aβ,4β,4aβ,7β,7aα,8aβ)]8a-[(2R,6R)-(4-allyl-6-methyl-morpholin-2-yl)-oxymethyl]-4-(hydroxyimino methyl)-4,4a,5,6,7,7a,8,8a-octahydro-7-methyl-3-(1-methylethyl)-1,4-methano-s-indacene-3a(1H)-carboxylic acid Hydroxylamine hydrochloride (103 mg) was added to a solution of Example 2 (233 mg) in dry toluene (5 ml) in the presence of triethylamine (0.25 ml). The reaction mixture was stirred 1 hour under reflux until a white precipitate appears. It was then concentrated and partitioned between 1N hydrochloric acid (15 ml) and dichloromethane (15 ml). The organic layer was washed with brine dried over anhydrous sodium sulfate and concentrated. The title compound (240 mg) was obtained as a white precipitate.

$^1$H-NMR (δ, ppm, CDCl$_3$): 13.25 (bs, 1H, COOH); 7.77 (s, 1H, HC=N), 6.14 (m, 1H, HC=C), 6.04 (dd, 1H, H-2, J=1.2 and 3.3 Hz), 5.59 and 5.52 (2d, 2H, H$_2$C=C, J=10.2 and 16.8 Hz respectively), 5.03 (m, 1H, H-2'), 4.33 (m, 1H, H-6'), 4.08 and 3.73 (2d, 2H, 8a-CH$_2$, J=9.0 Hz), 3.57 (m, 2H, CH$_2$N), 3.37 (d, 1H, 3'-Ha, J=11.4 Hz), 3.27 (d, 1H, 5'-Ha, J=11.4 Hz), 2.60 (t, 1H, CH(CH$_3$)$_2$, J=3.9 Hz).

Intermediate 31

[1R-(1α,3aβ,4β,4aβ,7β,7aα,8aβ)]8a-[(2R,6R)-6-methyl-4-(1-methylpyrrol-2-ylmethyl)morpholin-2-yl)-oxymethyl]-4-(1,3-dioxolan-2-yl)-4,4a, 5,6,7,7a, 8,8a-octahydro-7-methyl-3-(1-methylethyl)-1,4-methano-s-indacene-3a(1H)-carboxylic acid A mixture of Intermediate 14 (100 mg; 0.2 mmol) and N-methyl-2-pyrrolcarbaldehyde (39 mg; 0.36 mmol) in dry acetonitrile (5 ml) was stirred at room temperature for 45 minutes. Then, gl. acetic acid (50 μl) was added and the resulting solution was treated with sodium borohydride (11 mg; 0.29 mmol) and stirred at room temperature for 1.5 hours. Afterwards, the reaction mixture was partitioned into ethyl acetate (10 ml) and water (10 ml). The organic layer was separated, washed with brine (2×10 ml), dried (sodium sulfate) and evaporated. The residue was purified by preparative thin layer chromatography using 1:2 ethyl acetate/hexane to afford the title compound (24 mg).

$^1$H-NMR (δ, ppm, CDCl$_3$): 6.59 (m, 1H, pyrrolic H-5), 6.02 (m, 2H, pyrrolic H-3 and 4), 5.95 (dd, 1H, H-2, J=1.5 and 3.6 Hz), 4.59 (s, 1H, OCHO).

Intermediate 32

[1R-(1α, 3aβ,4β,4aβ,7β,7aα,8aβ)]8a-[(2R,6R)-6-methyl-4[(E)-2-buten-1yl]morpholin-2-yl)-oxymethyl]-4-(1,3-dioxolan-2-yl)-4,4a,5,6,7,7a,8,8a-octahydro-7-methyl-3-(1-methylethyl)-1,4-methano-s-indacene-3a(s 1H)-carboxylic acid A mixture of Intermediate 14 (200 mg; 0.4 mmol), (E)-1-bromo-2-butene (54 mg; 0.4 mmol) and solid sodium bicarbonate (67 mg; 0.8 mmol) in absolute ethanol (7 ml) was stirred at 70° C. for 4 hours. After cooling and removal of the solvent, the residue was purified by preparative thin layer chromatography using 5% methanol in dichloromethane as eluent to give the title compound (137 mg).

$^1$H-NMR (δ, ppm, CDCl$_3$): 5.96 (dd, 1H, H-2, J=1.2 and 3.3 Hz), 5.61 (m, 1H, butenyl), 5.47 (m, 1H, butenyl), 4.62 (s, 1H, OCH$_2$O), 4.41 (dd, 1H, H-2', J=2.4 and 8.4 Hz), 4.15 to 3.80 (m, 5H, 8a-CH$_2$and OCH$_2$CH$_2$O), 3.70 (AB system, 1H, 8a-CH$_2$), 3.64 (m, 1H, H-6'), 3.02 to 2.60 (m, 5H, allyl-CH$_2$—N+2×CH—N+H-1).

Intermediate 33

[1R-(1α,3aβ,4β,4aβ,7β,7aα,8aβ)]8a-[(2R,6R)-6-methyl-4-(4-bromobenzyl)morpholin-2-yl)-oxymethyl]-4-(1,3-dioxolan-2-yl)-4,4a,5,6,7,7a,8,8a-octahydro-7-methyl-3-(1-methylethyl)-1,4-methano-s-indacene-3a(1H)-carboxylic acid diphenylmethyl ester A mixture of Intermediate 3 (250 mg; 0.37 mmol), sodium cyanoborohydride (73 mg; 1.1 mmol), 4-bromobenzylamine hydrochloride (206 mg; 0.92 mmol) and triethylamine (100 mg; 0.99 mmol) in dry acetonitrile (12.5 ml ) was stirred at room temperature for 10 minutes. Glacial acetic acid (21 μl) was added and the resulting solution was stirred at room temperature for 1.5 hours. Afterwards, the reaction mixture was partitioned into ethyl acetate (10 ml) and water (10 ml). The organic layer was separated, washed with brine (2×10 ml), dried (sodium sulfate) and evaporated. The residue was purified by column chromatography using 1:2 ethyl acetate/hexane to afford the title compound (165 mg).

$^1$H-NMR (δ, ppm, CDCl$_3$): 7.43 (m, 5H, Ph), 7.33 (m, 7H, Ph+AB system 4-BrBn), 7.17 (AB system, 2H, 4-BrBn), 6.93 (s, 1H, Ph$_2$CH), 5.80 (dd, 1H, H-2, J=1.2 and 3.3 Hz), 5.06 (s, 1H, OCHO), 4.38 (dd, 1H, H-2', J=2.4 and 8.7 Hz), 4.04 (AB system, 1H, 8a-CH$_2$), 3.81 (m, 4 H, OCH$_2$CH$_2$O), 3.72 (AB system, 1H, 8a-CH$_2$), 3.65 (m, 1H, H-6'), 3.4 (AB system, 2H, BnCH$_2$N), 2.80 (m, 1H, CH—N).

Intermediate 34

[1R-(1α,3aβ,4β,4aβ,7β,7aα,8aβ)]8a-[(2R,6R)-6-methyl4-(2,2,2-trifluoroethyl)morpholin-2-yl)-oxymethyl]-4-(1,3-dioxolan-2-yl)-4,4a,5,6,7,7a,8,8a-octahydro-7-methyl-3-(1-methylethyl)-1,4-methano-s-indacene-3a(1H)-carboxylic acid diphenyl ester A mixture of Intermediate 3 (200 mg; 0.30 mmol), trifluoroethylamine (89 mg; 0.9 mmol) in dry acetonitrile (5 ml) was stirred at room temperature for 10 minutes. Then, gl. acetic acid (100 μl) and sodium borohydride (35 mg; 0.9 mmol) were added and the resulting solution was stirred at room temperature for 3 hours. Afterwards, the reaction mixture was partitioned into ethyl acetate (10 ml) and water (10 ml). The organic layer was separated, washed with brine (2×10 ml), dried (magnesium sulfate) and evaporated. The residue was purified by column chromatography using 1:3 ethyl acetate/hexane to afford the title compound (114 mg).

$^1$H-NMR (δ, ppm, CDCl$_3$): 7.44 (m, 4H, Ph), 7.33 (m, 6H, Ph), 6.93 (s, 1H, Ph$_2$CH), 5.83 (dd, 1H, H-2, J=1.2 and 3.3 Hz), 5.07 (s, 1H, OCHO), 4.38 (dd, 1H, H-2', J=2.4 and 8.7 Hz), 4.05 (AB system, 1H, 8a-CH$_2$), 3.81 (m, 4 H, OCH$_2$CH$_2$O), 3.75(AB system, 1H, 8a-CH$_2$), 3.6 (m, 1H, H-6'), 2.95 (q, 2H, CF$_3$CH$_2$N, J=9.6 Hz), 2.87 (m, 1H, CH—N), 2.71 (m, 1H, CH—N).

Intermediate 35

[1R-(1α,3aβ,4β,4aβ,7β,7aα,8aβ)]8a-[(2R,6R)-6-methyl-4-(cyclopropylmethyl )morpholin-2-yl)-oxymethyl]-4-(1,3-dioxolan-2-yl)-4,4a,5,6,7,7a,8,8a-octahydro-7-methyl-3-(1-methylethyl)-1,4-methano-s-indacene-3a(1H)-carboxylic acid diphenylmethyl ester A mixture of Intermediate 3 (200 mg; 0.30 mmol), cyclopropylmethylamine (64 mg; 0.9 mmol) in dry acetonitrile (6 ml) was stirred at room temperature for 10 minutes. Glacial acetic acid (103 µl) and sodium borohydride (35 mg; 0.9 mmol) were added and the resulting solution was stirred at room temperature for 2 hours. Afterwards, the reaction mixture was partitioned into ethyl acetate (10 ml) and water (10 ml). The organic layer was separated, washed with brine (2×10 ml), dried (magnesium sulfate) and evaporated. The residue was purified by column chromatography using 1:3 ethyl acetate lhexane to afford the title compound (46 mg).

$^1$H-NMR (δ, ppm, CDCl$_3$): 7.42 (m, 4H, Ph), 7.33 (m, 6H, Ph), 6.94 (s, 1H, Ph$_2$CH), 5.85 (dd, 1H, H-2, J=1.1 and 3.3 Hz), 5.07 (s, 1H, OCHO), 4.43 (dd, 1H, H-2', J=2.4 and 8.7 Hz), 4.07 (AB system, 1H, 8a-CH$_2$), 3.81 (m, 6 H, OCH$_2$CH$_2$O+8a-CH$_2$+H-6'), 2.95 (m, 1H, CHN), 2.81 (m, 1H, CH—N), 2.56 (m, 2H, (CH$_3$)$_2$CH+H-1).

Intermediate 36

[1R-(1α,3β,4β,4aβ,7β,7aα,8aβ)]8a-[(2R,6R)-6-methyl-4-(4-fluorobenzyl)morpholin-2-yl)-oxymethyl]-4-(1,3-dioxolan-2-yl)-4,4a,5,6,7,7a,8,8a-octahydro-7-methyl-3-(1-methylethyl)-1,4-methano-s-indacene-3a(1H)-carboxylic acid diphenylmethyl ester A mixture of Intermediate 3 (40 mg; 0.06 mmol), 4-fluorobenzylamine (24 mg; 0.15 mmol) in dry acetonitrile (1 ml) was stirred at room temperature for 10 minutes. Glacial acetic acid (5 µl) and sodium cyanoborohydride (12 mg; 0.18 mmol) were added and the resulting solution was stirred at room temperature for 2 hours. Afterwards, the reaction mixture was partitioned into ethyl acetate (10 ml) and water (10 ml). The organic layer was separated, washed with brine (2×10 ml), dried (magnesium sulfate) and evaporated. The residue was purified by column chromatography using 1:2 ethyl acetate /hexane to afford the title compound (10 mg).

$^1$H-NMR (δ, ppm, CDCl$_3$): 7.44 (m, 6H, Ph+AB system 4F—Bn), 7.33 (m, 6H, Ph), 7.00 (AB system, 2H, 4F—Bn), 6.93 (s, 1H, Ph$_2$CH), 5.83 (dd, 1H, H-2, J=1.2 and 3.3 Hz), 5.06 (s, 1H, OCHO), 4.38 (dd, 1H, H-2', J=2.4 and 8.7 Hz), 4.05 (AB system, 1H, 8a-CH$_2$), 3.81 (m, 4 H, OCH$_2$CH$_2$O), 3.73(AB system, 1H, 8a-CH$_2$), 3.65 (m, 1H, H-6'), 3.45 (br s, 2H, BnCH$_2$N), 2.80 (m, 1H, CH—N).

Intermediate 37

[1R-(1α,3β,4β,4aβ,7β,7aα,8aβ)]8a-[(2R,6R)-6-methyl-4-(cyclohexen-3-yl)morpholin-2-yl)-oxymethyl]-4-(1,3-dioxolan-2-yl)-4,4a,5,6,7,7a,8,8a-octahydro-7-methyl-3-(1-methylethyl)-1,4-methano-s-indacene-3a(1H)-carboxylic acid A mixture of Intermediate 14 (200 mg; 0.4 mmol), 3-bromocyclohexene (64 mg; 0.8 mmol) and solid sodium bicarbonate (67 mg; 0.8 mmol) in acetonitrile (6 ml) was stirred at reflux for 6 hours. After cooling and removal of the solvent, the residue was purified by column chromatography using 5% methanol in dichloromethane as eluent to give the title compound (48 mg).

$^1$H-NMR (δ, ppm, CDCl$_3$): 5.95 (dd, 1H, H-2, J=1.2 and 3.3 Hz), 5.81 (m, 1H, CH=CH), 5.60 (m, 1H, CH=CH), 4.61 (s, 1H, OCHO), 4.41 (m, 1H, H-2'), 4.15 to 3.5 (m, 7H, OCH$_2$CH$_2$O+2×ABsystem 8aCH$_2$+H-6'), 3.2 (br s, 1H, CH=CH—CH—N), 2.75 (m, 1H, CHN), 2.65 (m, 1H, H-1), 2.56 (m, 1H, CHN).

Intermediate 38

[1R-(1α,3β,4β,4aβ,7β,7aα,8aβ)]8a-[(2R,6R)-6-methyl-4-allyl-morpholin-2-yl)-oxymethyl]-4-(1,3-dioxolan-2-yl)-4,4a,5,6,7,7a,8,8a-octahydro-7-methyl-3-(1-methylethyl)-1,4-methano-s-indacene-3a(1H)-carboxylic acid diphenylmethyl ester A mixture of Intermediate 3 (250 mg; 0.37 mmol), sodium cyanoborohydride (73 mg; 1.1 mmol), allylamine (52 mg; 0.92 mmol) and triethylamine (0.14 ml; 0.99 mmol) in dry acetonitrile (12.5 ml) was stirred at room temperature for 10 minutes. Glacial acetic acid (21 µl) was added and the resulting solution was stirred at room temperature for 1.5 hours. Afterwards, the reaction mixture was partitioned into ethyl acetate (10 ml) and water (10 ml). The organic layer was separated, washed with brine (2×10 ml), dried (sodium sulfate) and evaporated. The residue was purified by column chromatography using 1:2 ethyl acetate/hexane to afford the title compound (165 mg).

$^1$H-NMR (δ, ppm, CDCl$_3$): 7.26 to 7.46 (m, 10 H, 2×Ph), 6.94 (s, 1H, Ph$_2$CH), 5.84 (m, 2H, H-2 and 1×allyl), 5.17 (m, 2H, allyl), 5.06 (s, 1H, OCHO), 4.39 (dd, 1H, H-2', J=2.1 and 8.7 Hz), 4.05 (AB system, 1H, 8a-CH2), 3.85 to 3.60 (m, 6H, OCH2CH2O+AB system+H-6'), 2.98 (m, 2H, allylic CH$_2$,), 2.84 (m, 1H, CHN), 2.67 (m, 1H, CHN).

Intermediate 39

[1R-(1α,3β,4β,4aβ,7β,7aα,8aβ)]8a-[(2R,6R)-6-methyl-morpholin-2-yl)-oxymethyl]-4-(1,3-dioxolan-2-yl)-4,4a,5,6,7,7a,8,8a-octahydro-7-methyl-3-(1-methylethyl)-1,4-methano-s-indacene-3a(1H)-carboxylic acid diphenylmethyl ester A solution of Intermediate 38 (1.5 g; 2.2 mmol) in v/v 10/1 ethanol/water (20 ml) is treated with Wilkinson's catalyst (0.140 g; 0.15 mmol) and diazabicyclo[2.2.2]octane (126 mg; 1.1 mmol) under argon for 30 minutes. The mixture is then heated under reflux for 4 hours. After this time, the reaction mixture is diluted with ethyl acetate, washed with water (1×20 ml) and dried (sodium sulfate) to give a residue which is purified by column chromatography (5% v/v methanol in dichloromethane) to afford the title compound (1.1 g)

$^1$H-NMR (δ, ppm, CDCl$_3$): 7.26 to 7.44 (m, 10 H, 2×Ph), 6.94 (s, 1H, Ph$_2$CH), 5.84 (dd, 1H, H-2, J=0–9 and 3.3 Hz), 5.07 (s, 1H, OCHO), 4.38 (dd, 1H, H-2', J=2.1 and 8.7 Hz), 4.05 (AB system, 1H, 8a-CH2), 3.85 to 3.60 (m, 6H, OCH2CH2O+AB system+H-6'), 2.97 (m, 1H, CHN), 2.82 (m, 1H, CHN).

Intermediate 40

[1R-(1α,3β,4β,4aβ,7β,7aα,8aβ)]8a-[(2R,6R)-6-methyl-4-(phenacylmorpholin-2-yl)-oxymethyl]-4-(1,3-dioxolan-2-yl)-4,4a,5,6,7,7a,8,8a-octahydro-7-methyl-3-(1-methylethyl)-1,4-methano-s-indacene-3a(1H)-carboxylic acid diphenylmethyl ester Phenacyl bromide (40 g; 0.20 mmol) and triethylamine (61 mg; 0.60 mmo) were added into a solution of Intermediate 39(105 mg; 0.17 mmol) in dichloromethane (5 ml). The reaction mixture was stirred at room temperature for 12 hours. After removal of the solvent, the residue was purified by preparative thin layer chromatography using 5% v/v methanol in dichloromethane to afford the title compound.

$^1$H-NMR (δ, ppm, CDCl$_3$): 7.97 (m, 2H, PhCO), 7.58 (m, 1H, PhCO), 7.48 (m, 2H, PhCO), 7.42 (m, 4H, Ph), 7.33 (m, 6H, Ph), 6.93 (s, 1H, Ph$_2$CH), 5.83 (dd, 1H, H-2, J=1.2 and 3.3 Hz), 5.07 (s, 1H, OCHO), 4.51 (dd, 1H, H-2', J=2.4 and 8.7 Hz), 4.07 (AB system, 1H, 8a-CH$_2$), 3.81 (m, 8H, OCH$_2$CH$_2$O+8a-CH$_2$+COCH$_2$N+H-6'), 2.95 (m, 1H, CHN), 2.81 (m, 1H, CH—N), 2.61 (m, 1H, (CH$_3$)$_2$CH), 2.52 (m, 1H, H-1).

EXAMPLE 1

Method A

The Intermediate 4 was dissolved in dichloromethane (5 ml) and treated with trifluoroacetic acid (10% vol) at room temperature. Once the reaction was concluded (1 hour aprox.) a solution of 10% aqueous sodium sulphate solution (5 ml) was added and the two phases partitioned. The organic layers were washed twice with 10% aqueous sodium sulphate (5 ml), then dried over sodium sulphate. Elimination of the solvent gave crudes which were purified by preparative Thin Layer Chromatography (silica gel), eluting with dichloromethane:methanol v:v 15:1.

Method B

A solution of the intermediate 4 (0.25 mmol) in ethyl acetate (7 ml) was purged with nitrogen for 5 minutes and Palladium 10% on charcoal (50–60% w:w) was added onto it. This suspension was shaken at room temperature under hydrogen (40 psi) for 5 hours. Filtration of the catalyst and removal of the solvent gave a crude which was dissolved in tetrahydrofuran (10 ml). To this solution were added methanol (5 ml) and 1N aqueous hydrochloric acid (5 ml). After stirring for 3 hours the solution was neutralized by adding 1 N aqueous sodium hydroxide and extracted with ethyl acetate (10 ml). The organic layer was washed twice with brine (1×10 ml) and the aqueous layer back extracted with ethyl acetate (5 ml). The combined organic layers were dried over sodium sulphate and the solvent removed to dryness to give a final crude.

EXAMPLE 1a

[1R-(1α,3aβ,4β,4aβ,7β,7aα,8aβ)]8a-[(2R,6R)-(4-cyclopropyl-6-methyl-morpholin-2-yl)-oxymethyl]-4-formyl-4,4a,5,6,7,7a,8,8a-octahydro-7-methyl-3-(1-methylethyl)-1,4-methano-s-indacene-3a(1H)-carboxylic acid (60 mg) was prepared from Intermediate 4a (150 mg) using method A above described.

$^1$H-NMR (CDCl$_3$, ppm): 9.82 (s, 1H, CHO), 6.05 (dd, 1H, H2, J=1.2 and 3.3 Hz), 4.41 (dd, 1H, H2', J=2.4 and 9 Hz), 4.12 (d, 1H, 8aCH$_2$, J=9.3 Hz), 3.64 (m, 1H, H6'), 3.54 (d, 1H, 8aCH$_2$, J=9.3 Hz), 3.01 (db, 1H, H3', J=10.5 Hz), 2.85 (bd, 1H, H5', J=10.8 Hz), 2.59 (t, 1H, H1, J=4.2 Hz), 2.29 (st, 1H, CH(CH$_3$)$_2$, J=6.9 Hz), 1.69 (m, 1H, NCH), 0.65–0.4 (m, 4H, CH$_2$CH$_2$).

EXAMPLE 1b

[1R-(1α,3aβ,4β,4aβ,7β,7aα,8aβ)]8a-[(2R,6R)-(4-ethyl-6-methyl-morpholin-2-yl)-oxymethyl]-4-formyl-4,4a,5,6,7,7a,8,8a-octahydro-7-methyl-3-(1-methylethyl)-1,4-methano-s-indacene-3a(1H)-carboxylic acid (48 mg) was prepared from Intermediate 4b (100 mg) using method A above described.

$^1$H-NMR (CDCl$_3$, ppm): 9.85 (s, 1H, CHO), 6.01 (dd, 1H, H2, J=1.2 and 3.3 Hz), 4.58 (dd, 1H, H2', J=2.1 and 9 Hz), 3.89 (m, 2H, H6'+8aCH$_2$), 3.80 (d, 1H, 8aCH$_2$, J=9.0 Hz), 2.98 (bd, 1H, H3', J=11.1 Hz), 2.90 (bd, 1H, H5', J=11.1 Hz), 2.65 (m, 3H, NCH$_2$+H1), 2.32 (m, 1H, CH(CH$_3$)$_2$); 2.19 (td, 1H, H4a, J=6.1 and 12.2 Hz).

EXAMPLE 1c

[1R-(1α,3aβ,4β,4aβ,7β,7aα,8aβ)]8a-[(2R,6R)-(4-allyl-6-methyl-morpholin-2-yl)-oxymethyl]-4-formyl-4,4a,5,6,7,7a,8,8a-octahydro-7-methyl-3-(1-methylethyl)-1,4-methano-s-indacene-3a(1H)-carboxylic acid (47 mg) was prepared from intermediate 4c (165 mg) using method A above described.

$^1$H-NMR (CDCl$_3$, ppm): 9.82 (s, 1H, CHO), 6.03 (dd, 1H, H2, J=0.9 and 3.3 Hz), 5.88 (m, 1H, CH=), 5.25 (m, 2H, =CH$_2$), 4.52 (dd, 1H, H2', J=2.1 and 8.7 Hz), 4.00 (d, 1H, 8aCH$_2$, J=9.3 Hz), 3.79 (m, 1H, H6'), 3.66 (d, 1H, 8aCH$_2$, J=9.3 Hz), 3.131 (m, 2H, NCH$_2$), 2.93 (bd, 1H, H3', J=10.5 Hz), 2.80 (bd, 1H, H5', J=11.1 Hz), 2.63 (t, 1H, H1, J=3.9 Hz).

EXAMPLE 1d

[1R-(1α,3aβ,4β,4aβ,7β,7aα,8aβ)]8a-[(2R,6R)-4-(2-methoxyethyl)-6-methyl-morpholin-2-yl)-oxymethyl]-4-formyl-4,4a,5,6,7,7a,8,8a-octahydro-7-methyl-3-(1-methylethyl)-1,4-methano-s-indacene-3a(1H)-carboxylic acid (90 mg) was prepared from Intermediate 4d (130 mg) using method A above described.

$^1$H-NMR (CDCl$_3$, ppm): 9.83 (s, 1H, CHO), 6.04 (dd, 1H, H2, J=1.5 and 3.6 Hz), 4.54 (dd, 1H, H2', J=2.1 and 9 Hz), 4.08 (d, 1H, 8aCH$_2$, J=9 Hz), 3.79 (m, 1H, H6'), 3.60 (m, 3H, CH$_2$O+8aCH$_2$), 3.33 (s, 3H, OCH$_3$), 2.98 (bd, 1H, H3', J=11.1 Hz), 2.82 (bd, 1H, H5', J=11.1 Hz), 2.71 (m, 2H, NCH$_2$), 2.61 (t, 1H, H1, J=3.9 Hz), 2.31 (m, 1H, CH(CH$_3$)$_2$).

EXAMPLE 1e

[1R-(1α,3aβ,4β,4aβ,7β,7aα,8aβ)]8a-[[(2R,6R)-(4-(1,1-dimethylethyl)-6-methyl-morpholin-2-yl)]-oxymethyl]-4-formyl-4,4a,5,6,7,7a,8,8a-octahydro-7-methyl-3-(1-methylethyl)-1,4-methano-s-indacene-3a(1H)-carboxylic acid (57 mg) was prepared from intermediate 4e (120 mg) using method A above described.

$^1$H-NMR (CDCl$_3$, ppm): 9.92 (s, 1H, CHO), 6.00 (dd, 1H, H2, J=1.2 and 3.3 Hz), 4.73 (dd, 1H, H2', J=2.1 and 9 Hz), 4.0 (m, 1H, H6'), 3.88 (bs, 2H, 8aCH$_2$), 3.03 (2bd, 2H, H3'+H5', J=12.3 Hz), 2.63 (m, 1H, H1), 2.33 (m, 1H, CH(CH$_3$)$_2$).

EXAMPLE 1f

[1R-(1α,3aβ,4β,4aβ,7β,7aα,8aβ)]8a-[(2R,6R)-(4-propyl-6-methyl-morpholin-2-yl)-oxymethyl]-4-formyl-4,4a,5,6,7,7a,8,8a-octahydro-7-methyl-3-(1-methylethyl)-1,4-methano-s-indacene-3a(1H)-carboxylic acid (71 mg) was prepared from Intermediate 4f (170 mg) using the method B above mentioned. The crude product obtained was purified by preparative Thin Layer Chromatography (Silica gel), eluting with mixtures of dichloromethane:methanol v:v 15:1.

$^1$H-NMR (CDCl$_3$, ppm): 9.84 (s, 1H, CHO), 6.01 (dd, 1H, H2, J=1.2 and 3.3 Hz), 4.56 (dd, H2', J=2.1 and 9 Hz), 3.90 (m, 2H, H6'+8aCH$_2$), 3.77 (d, 1H, 8aCH$_2$, J=9.3 Hz), 2.97 (bd, 1H, H3', J=10.8 Hz), 2.89 (bd, 1H, H5', J=11.1 Hz), 2.65 (t, 1H, H1, J=3.6 Hz), 2.52 (m, 2H, NCH$_2$), 2.31 (m, 1H, CH(CH$_3$)$_2$), 2.19 (td, 1H, H4a, J=6.1 and 12.2 Hz).

EXAMPLE 1g

[1R-(1α,3aβ,4β,4aβ,7β,7aα,8aβ)]8a-[(2R,6R)-(4,6-dimethyl-morpholin-2-yl)-oxymethyl]-4-formyl-4,4a,5,6,7,7a,8,8a-octahydro-7-methyl-3-(1-methylethyl)-1,4-methano-s-indacene-3a(1H)-carboxylic acid (170 mg) was obtained from intermediate 4g (330 mg) using the method B above. The crude product was a crystalline material which was triturated with hexane and the white solid thus obtained filtered off and washed three times with hexane.

$^1$H-NMR (CDCl$_3$, ppm): 9.83 (s, 1H, CHO), 6.00 (dd, 1H, H2, J=1.2 and 3.6 Hz), 4.53 (dd, 1H, H2', J=1.8 and 9 Hz), 3.85 (m, 2H, H6'+8aCH$_2$), 3.78 (d, 1H, 8aCH$_2$, J=9.0 Hz), 2.85 (2bd, 2H, H3'+H5', J=12 Hz), 2.67 (t, 1H, H1, J=3.6 Hz), 2.41 (s, 3H, NCH$_3$), 2.32 (m, 1H, CH(CH$_3$)$_2$).

EXAMPLE 1h

[1R-(1α,3aβ,4β,4aβ,7β,7aα,8aβ)]8a-[(2R,6R)-(6-methyl-4-phenyl-morpholin-2-yl)-oxymethyl]-4-formyl-4, 4a,5,6,7,7a,8,8a-octahydro-7-methyl-3-(1-methylethyl)-1,4-methano-s-indacene-3a(1H)-carboxylic acid (84 mg) was prepared from intermediate 4h using the method A above described, after extraction with dichloromethane:methanol v/v 10:1.

$^1$H-NMR (CDCl$_3$, ppm): 9.62 (s, 1H, CHO), 7.20 (dd, 2H, Ar, J=7.5 and 8.7 Hz), 6.93 (dd, 2H, Ar, J=0.9 and 8.7 Hz), 6.78 (t, 1H, Ar, J=7.2 Hz), 6.09 (dd, 1H, H2, J=1.2 and 3.3 Hz), 4.46 (dd, 1H, H2', J=2.4 and 8.4 Hz), 3.83 and 3.63 (2d, 2H, 8aCH$_2$, J=9.3 Hz), 3.73 (m, 1H, H6'), 3.56 and 3.52 (2bd, 2H, H3'+H5', J=10.5 Hz), 2.70 (t, 1H, H1, J=3.9 Hz).

EXAMPLE 1i

[1R-(1α,3aβ,4β,4aβ,7β,7aα,8aβ)]8a-[(2R,6R)-(4-benzyl-6-methylmorpholin-2-yl)-oxymethyl]-4-formyl-4,4a,5,6,7,7a,8,8a-octahydro-7-methyl-3-(1-methylethyl)-1,4-methano-s-indacene-3a(1H)-carboxylic acid (82 mg) was prepared from Intermediate 4i (155 mg) using the method A above, the desired compound being obtained after extraction of the appropriate fraction with dichloromethane:methanol v:v 10:1.

$^1$H-NMR (CDCl$_3$, ppm): 9.86 (s, 1H, CHO), 7.4–7.2 (m, 5H, Ph), 6.03 (dd, 1H, H-2, J=1.2 and 3.6 Hz), 4.49 (dd, 1H, H-2', J=2.1 and 8.7 Hz), 4.27 (d, 1H, 8a-CHa, J=9 Hz), 3.72 (m, 1H, H6'), 3.60 and 3.50 (2d, 2H, CH$_2$—Ph, J=12.6 Hz), 3.44 (d, 1H, 8a-CH$_b$, J=9.3 Hz), 2.85 (bd, 1H, Ha-3', J=10.8 Hz), 2.68 (bd, 1H, Ha-5', J=10.8 Hz), 2.50 (t, 1H, H-1, J=3.9 Hz), 2.30 (m, 1H, CHMe$_2$).

EXAMPLE 1j

[1R-(1α,3aβ,4β,4aβ,7β,7aα,8aβ)]8a-[(2R,6R)-(4-(2-ethylthioethyl)-6-methylmorpholin-2-yl)-oxymethyl]-4-formyl-4,4a,5,6,7,7a,8,8a-octahydro-7-methyl-3-(1-methylethyl)-1,4-methano-s-indacene-3a(1H)-carboxylic acid (95 mg) was obtained from Intermediate 4j (203 mg) using method A above the desired compound being obtained after extraction of the appropriate fraction with dichloromethane:methanol v:v 10:1.

$^1$H-NMR (CDCl$_3$, ppm): 9.83 (s, 1H, CHO), 6.05 (m, 1H, H-2), 4.49 (dd, 1H, H-2', J=2.4 and 9 Hz), 4.23 (bd, 1H, 8a-CHa, J=9 Hz), 3.72 (m, 1H, H-6'), 3.51 (d, 1H, 8a-CHb, J=9.3 Hz), 2.92 (bd, 1H, Ha-3', J=10.2 Hz), 2.73 (bd, 1H, Ha-5', J=11.1 Hz), 2.7–2.5 (m, 5H, H-1 and N—CH—CH$_2$—S), 2.56 (q, 2H, S—CH$_2$—Me, J=7.5 Hz), 2.3 (m, 1H, CHMe$_2$), 1.26 (t, 3H, S—CH$_2$—CH$_3$, J=7.5 Hz).

EXAMPLE 2

[1R-(1α,3aβ,4β,4aβ,7β, 7aα,8aβ)]8a-[(2R,6R)-(4-allyl-6-methyl-morpholin-2-yl)-oxymethyl]-4-formyl-4,4a,5,6,7,7a,8,8a-octahydro-7-methyl-3-(1-methylethyl)-1,4-methano-s-indacene-3a(1H)-carboxylic acid To a solution of Intermediate 5 (30 g) in dry acetonitrile (450 ml) were added consecutively ethylene glycol (36 ml), trimethylorthoformate (17.7 ml) and p-toluenesulphonic acid monohydrate (0.615 g). The reaction was stirred 20 minutes, then acetic acid (33 ml) was added at once. The solution thus obtained was added under nitrogen at 25° C., into a suspension of sodium borohydride (1.525 g) and allyl amine (48.6 ml) in dry acetonitrile (339 ml) over a period of 35 minutes. During this period of time, three additional portions of solid sodium borohydride (3×1.525 g, 3×0.625 equiv) were added at once at regular intervals.

The suspension thus obtained was stirred for 3 h at room temperature, then 1N NH$_4$Cl (1600 ml) was added dropwise over a period of 30 minutes. After stirring for 1 h, the white precipitate was collected by filtration, washed several times with water (1 L aprox). 21.6 g of the desired protected intermediate were obtained as a white powder. The filtrate was allowed to stand at room temperature for 24 h and an additional amount of 1.1 g of the desired compound were obtained. The white powder thus obtained was dissolved in tetrahydrofuran (250 ml) and 1N HCl (125 ml) was added over a period of 30 min. The solution was stirred at r.t. (3 h aprox.), then 1N NaOH (150 ml) was added over a period of 15 min. This solution was concentrated under vacuum to a half the volume (aprox.) in order to remove the THF and the resulting suspension diluted with a volume of water. The pH was adjusted to pH=11 aprox. with 1N NaOH in order to obtain a clear solution and 1N HCl was added carefully until pH=6.5. The white solid precipitated was collected by filtration, washed with water and dried to yield the title compound 20.7 g as a white powder.

EXAMPLE 3

[1R-(1α,3aβ,4β,4aβ,7β,7aα,8aβ)]8a-[(2R,6R)-(4-cyclopropyl-6-methyl-morpholin-2-yl)-oxymethyl]-4-formyl-4,4a,5,6,7,7a,8,8a-octahydro-7-methyl-3-(1-methylethyl)-1,4-methano-s-indacene-3a(1H)-carboxylic acid To a solution of intermediate 5 (30 g) in dry acetonitrile (450 ml) were added consecutively ethylene glycol (36 ml), trimethylorthoformate (17.7 ml) and p-toluenesulphonic acid monohydrate (0.615 g). The reaction was stirred for 20 minutes, then acetic acid (29.1 ml) was added at once. The solution thus obtained was added under nitrogen at 25° C., into a suspension of sodium borohydride (1.83 g), cyclopropylamine (45 ml, 10 equiv) and acetic acid (9.7 ml) in dry acetonitrile (339 ml) over a period of 35 minutes. During this period of time, three additional portions of solid sodium borohydride (3×1.83 g) were added at once at regular intervals. The suspension thus obtained was stirred at room temperature overnight (18–20 h aprox.), then 1N NH$_4$Cl (1600 ml) was added dropwise over a period of 30 minutes. After stirring for 1 h, the white precipitate was collected by filtration and washed several times with water (1 L aprox). 27.7 g of the desired protected intermediate were obtained as a white powder.

The white powder thus obtained was suspended in THF (350 ml) and 1N HCl (175 ml) was added over a period of 30 min. The solution was stirred at r.t. 3 h, then 1N NaOH (250 ml) was added over a period of 15 min. This solution was concentrated under vacuum in order to remove the tetrahydrofuran (275 ml) and the resulting basic aqueous solution (400 ml) was filtered. 1N HCl was added until pH=6.5 and the solid precipitated was collected by filtration and washed with water (aprox. 1 L). The solid thus obtained was triturated with a minimal amount of methanol and filtered. The methanol-washings of the filter cake were repeated until a colourless filtrate is obtained and this gave the title compound. (20–21 g) as a white powder.

EXAMPLE 4

[1R-(1α,3aβ,4β,4aβ,7β,7aα,8aβ)]8a-[(2R,6R)-(4-cyclopropyl-6-methyl-morpholin-2-yl)-oxymethyl]-4-formyl-4,4a,5,6,7,7a,8,8a-octahydro-7-methyl-3-(1-methylethyl)-1,4-methano-s-indacene-3a(1H)-carboxylic acid, potassium salt To a heated (80° C., oil bath temperature) suspension of Example 3 (470 mg) in 110 mL of a mixture 10:1 of acetonitrile:tetrahydrofuran was added 5 mL of an aqueous potassium hydroxide solution (0.199N). The mixture was stirred until all the solid was dissolved and then 100 mL of solvent was removed by distillation (105° C. oil bath temperature). The solution was allowed to reach room temperature and cooled at 5° C. for 24 hours. The crystalline solid formed was collected by filtration, washed with acetonitrile (6 mL) and dried under vacuum to yield the title compound (400 mg) as a white crystalline solid.

$^1$H-NMR (DMSO-$d_6$, ppm): 9.77 (s, 1H, CHO), 5.77 (dd, 1H, H-2, J=1.2 and 3.6 Hz), 4.13 (dd, 1H, H-2', J=2.1 and 8.7 Hz), 3.92 (d, 1H, 8aCH$_a$, J=9.6 Hz), 3.52 (d, 1H, 8aCH$_b$, J=9.6 Hz), 3.5–3.38 (m, 1H, H-6'), 2.78–2.64 (m, 2H, H$_a$-3' and H$_a$-5'), 2.48–2.35 (m, 2H, H-1 and CHMe$_2$), 0.42–0.22 (m, 4H, CH2—CH2(cyclopropyl)).

$^{13}$C-NMR (DMSO$_6$, ppm) 206.6 (CHO), 172.8 (CO$_2$K), 151.8 (C3), 127.3 (C2), 99.0 (C2'), 37.6 (CH-cyclopropyl), 5.5 and 5.4 (CH2—CH2(cyclopropyl)).

EXAMPLE 5

[1R-(1α,3aβ,4β,4aβ,7β,7aα,8aβ)]8a-[(2R,6R)-(4-allyl-6-methyl-morpholin-2-yl)-oxymethyl]-4-formyl-4,4a,5,6,7,7a,8,8a-octahydro-7-methyl-3-(1-methylethyl)-1,4-methano-s-indacene-3a(1H)-carboxylic acid, potassium salt To a heated (80° C., oil bath temperature) suspension of Example 2 (470 mg) in 110 mL of a mixture 10:1 of acetonitrile:tetrahydrofuran was added 5 mL of an aqueous potassium hydroxide solution (0.1 99N). The mixture was stirred until all the solid was dissolved and then 100 mL of solvent was removed by distillation (105° C. oil bath temperature). The solution was allowed to reach room temperature and cooled at 5° C. for 24 hours. The crystalline solid formed was collected by filtration, washed with acetonitrile (6 mL) and dried under vacuum to yield the title compound (385 mg) as a white crystalline solid.

$^1$H-NMR (DMSO-$d_6$, ppm): 9.75 (s, 1H, CHO), 5.86–5.68 (m, 2H, H-2 and CH=), 5.2–5.08 (m, 2H, =CH$_2$), 4.21 (dd, 1H, H-2', J=2.4 and 8.7 Hz), 3.93 (d, 1H, 8aCH$_a$, J=9.6 Hz), 3.6–3.46 (m, 2H, 8aCH$_b$ and H-6'), 2.90 (d, 2H, CH$_2$—CH=CH$_2$, J=6.6 Hz), 2.68 and 2.60 (2bd, 2H, H$_a$-3' and H$_a$-5', J=10.5 and 10.5 Hz), 2.46–2.32 (m, 2H, H-1 and CHMe$_2$).

$^{13}$C-NMR (DMSO-$d_6$, ppm) 206.6 (CHO), 172.9 (CO$_2$K), 151.8 (C3), 135.1 (CH=), 127.4 (C2), 117.8 (=CH2), 99.2 (C2').

EXAMPLE 6

[1R-(1α,3aβ,4β,4aβ,7β,7aα,8aβ)]8a-[(2R,6R)-(4-(2-propynyl)-6-methyl-morpholin-2-yl)-oxymethyl]-4-formyl-4,4a,5,6,7,7a,8,8a-octahydro-7-methyl-3-(1-methylethyl)-1,4-methano-s-indacene-3a(1H)-carboxylic acid To a solution of intermediate 5 (2.00 g) in acetonitrile (30 ml), ethylene glycol (2.4 m), methyl orthoformate (1.17 ml) and p-toluensulfonic acid monohydrate (0.041 g) were added. The solution was stirred at room temperature for 15 minutes and, then, acetic acid (2.18 ml) was added. This reaction mixture was added into a mixture of sodium borohydride (0.406 g) and propargylamine (2.89 ml) in acetonitrile (2 ml). After 1.5 hours, 1N aqueous ammonium chloride solution (200 ml) was added and the mixture was extracted with ethyl acetate (2×200 ml), washed with brine (1×250 ml) and dried (MgSO4). After filtration and evaporation of the solvent, the residue was dissolved into tetrahydrofuran (25 ml) and 1N hydrochloric acid (10 ml) was added. After 3.5 hours, 1N aqueous sodium hydroxide (12 ml) was added and the solvent was evaporated. The residue was purified by column chromatography using 5% v/v methanol in dichloromethan to give the title compound (1.67 g).

$^1$H-NMR (CDCl$_3$, ppm): 9.81 (s, 1H, CHO), 6.06 (dd, 1H, H-2, J=1.5 and 3.6 Hz), 4.49 (dd, 1H, H-2', J=2.4 and 8.7 Hz), 4.30 (d, 1H, 8a-CH$_a$, J=9.3 Hz), 3.70 (m, 1H, H-6'), 3.47 (d, 1H, 8a-CH$_b$, J=9.3 Hz), 3.33 (m, 2H, Propargyl-CH$_2$—N), 2.85 (m, 1H, CH$_2$—N), 2.64 (m, 1H, CH$_2$—N), 2.54 (m, 1H, H-1)

EXAMPLE 7

[1R-(1α,3aβ,4β,4aβ,7β,7aα,8aβ)]8a-[(2R,6R)-(4-(2-bromoallyl)-6-methyl-morpholin-2-yl)-oxymethyl]-4-formyl-4,4a,5,6,7,7a,8,8a-octahydro-7-methyl-3-(1-methylethyl)-1,4-methano-s-indacene-3a(1H)-carboxylic acid A solution of Intermediate 7 (480 mg) in tetrahydrofuran (18 ml) was treated with a 50% v/v solution of 1N hydrochloric acid in tetrahydrofuran (27 ml). After 1.5 hours the mixture was diluted with ethyl acetate (30 ml) and washed with brine (2×30 ml). Evaporation of the solvent gave the title compound (428 mg)

$^1$H-NMR (CDCl$_3$, ppm): 9.84 (s, 1H, CHO), 6.06 (dd, 1H, H-2, J=1.2 and 3.3 Hz), 5.84 (br s, 1H, CH$_2$=), 5.60 (br s, 1H, CH$_2$=), 4.51 (br d, 1H, H-2'), 4.40 (d, 1H, 8a-CH$_2$, J=9.3 Hz), 3.72 (br s, H6'), 3.40 (d, 1H, 8a-CH$_2$, J=9.3 Hz), 3.17 (br s, 2H, allyl-CH$_2$—N), 2.88 (m, 1H, CH—N), 2.66 (m, 1H, CH—N), 2.50 (m, 1H, H-1)

EXAMPLE 8

[1R-(1α,3aβ,4β,4aβ,7β,7aα,8aβ)]8a-[(2R6R)-(4-(2-chloroallyl)-6-methyl-morpholin-2-yl)-oxymethyl]-4-formyl-4,4a,5,6,7,7a,8,8a-octahydro-7-methyl-3-(1-methylethyl)-1,4-methano-s-indacene-3a(1H)-carboxylic acid Method A A solution of Intermediate 8 (0.880 g) in a 50% v/v mixture of 1N hydrochloric acid and tetrahydrofuran (144 ml) was stirred at room temperature for 20 hours. The reaction mixture was diluted with ethyl acetate and washed with water. The organic layer was washed with brine, dried (magnesium sulfate) and evaporated. The obtained residue was purified by column chromatography using 5% methanol in dichloromethane as eluent to give the title compound (0.540 g).

$^1$H-NMR (CDCl$_3$, ppm): 9.84 (s, 1H, CHO), 6.05 (dd, 1H, H-2, J=1.5 and J=3.4 Hz), 5.38 (m, 1H, CH$_2$=), 5.35 (m, 1H, CH$_2$=), 4.51 (dd, 1H, H-2', J=2.4 and J=8.6 Hz), 4.41 (d, 1H, 8a-CH$_2$, J=9.6 Hz), 3.71 (m, 1H, H-6'), 3.39 (d, 1H, 8a-CH$_2$, J=9.6 Hz), 3.13 (s, 2H, allyl-CH$_2$—N), 2.90 (m, 1H, CH—N), 2.67 (m, 1H, CH—N), 2.50 (m, 1H, H-1), 2.31 (m, 1H, CH(CH$_3$)$_2$).

$^{13}$C-NMR (CDCl$_3$, ppm) 206.5 (CHO), 174.9 (CO$_2$H), 148.8 (C-3), 137.9 (HClC=), 130.1 (C-2), 115.1 (=CH$_2$), 99.0 (C-2'), 74.3, 65.1, 58.9 (C-3a, C-4, C-8a), 73.8 (8a-CH$_2$), 69.7 (C-6'), 62.9, 57.8, 55.6 (333 CH$_2$—N), 46.8, 41.1, 41.0, 30.9, 27.4 (5×CH), 31.8, 29.4, 28.8, 26.2 (4 CH$_2$), 22.5, 20.9, 18.2, 17.2 (4×CH$_3$).

Method B

In a 1 L jacketed reactor was placed commercial acetonitrile (170 ml). Intermediate 15 (14.7 g) was added portionwise at 25° C. and sodium hydroxide (3.4 g in 170 ml of H₂O) was added dropwise via dropping funnel oven a period of 5 minutes. Once all the material was dissolved, lithium bromide (2.9 g) was added at once and the mixture stirred for 15 minutes, then heated up to 65° C. A solution of 2.3-dichloro-propene in commercial acetonitrile (45 ml) was added in three portions over a period of 6 hours and the heating continued for additional 9 hours, then allowed to cool to 25° C. and kept under these conditions overnight.

Hexane (150 ml) was added and the two phases partitioned. The aqueous layer was washed twice with hexane (2×150 ml) and the organic layer back extracted with 150 ml of 0.25 N sodium hydroxide.

The combined aqueous layers were concentrated under $N_2$ (55° C.) in order to remove the acetonitrile. To the aqueous suspension thus obtained were added water (150 ml) and 1N hydrochloric acid until pH=7.5. The precipitate was collected by filtration washed with a mixture acetonitrile/water v/v 1:2, and dried at the vacuum oven (40° C.) to yield the title compound (13.2 g) as a whitish powder.

$^1$H-NMR (δ, ppm, CDCl₃): 9.83 (s, 1H, CHO), 6.05 (dd, 1H, H2, J=1.2 and 3.3 Hz), 5.37 (dd, 2H, =CH₂, J=0.9 and 8.1 Hz), 4.51 (dd, 1H, H2', J=2.1 and 8.7 Hz), 4.38 (d, 1H, 8aCH₂, J=9.3 Hz), 3.71 (m, 1H, H6'), 3.41 (d, 1H, 8aCH₂, J=9.3 Hz), 3.13 (bs, 2H, NCH₂), 2.89 (bd, 1H, H3', J=10.5 Hz), 2.67 (bd, 1H, H5', J=11.1 Hz), 2.51 (t, 1H, H1, J=3.9 Hz), 2.31 (m, 1H, CH(CH₃)₂).

EXAMPLE 9

[1R-(1α,3aβ,4β,4aβ,7β,7aα,8aβ)]8a-[(2R,6R)-(4-(2-chloroallyl)-6-methyl-morpholin-2-yl)-oxymethyl]-4-formyl-4,4a,5,6,7,7a,8,8a-octahydro-7-methyl-3-(1-methylethyl)-1,4-methano-s-indacene-3a(1H)-carboxylic acid, potassium salt Method A To a heated (80° C., oil bath temperature) suspension of Example 8 (257 mg) in 55 mL of a mixture 10:1 of acetonitrile:tetrahydrofuran was added 2.55 mL of an aqueous potassium hydroxide solution (0.199N). The mixture was stirred until all the solid was dissolved and then 50 mL of solvent was removed by distillation (105° C. oil bath temperature). The solution was allowed to reach room temperature and cooled at 5° C. for 24 hours. The crystalline solid formed was collected by filtration, washed with acetonitrile (3 mL) and dried under vacuum to yield the title compound (200 mg) as a white crystalline solid.

$^1$H-NMR (DMSO-d₆, ppm): 9.75 (s, 1H, CHO), 5.8–5.74 (m, 1H, H-2), 5.50 (d, 1H, =CHa, J=1.2), 5.36 (d, 1H, =CHb), J=1.2 Hz), 4.23 (dd, 1H, H-2', J=2.1 and 8.4 Hz), 3.94 (d, 1H, 8aCH$_a$, J=9.6 Hz), 3.62–3.48 (m, 2H, 8aCH$_b$ and H-6'), 3.11 (s, 2H, CH₂—CCl=CH₂), 2.69 and 2.61 (2bd, 2H, H$_a$-3' and H$_a$-5', J=10.2 and 10.5 Hz), 2.46–2.34 (m, 2H, H-1 and CHMe₂).

$^{13}$C-NMR (DMSO-d₆, ppm) 206.6 (CHO), 172.7 (CO₂K), 151.8 (C3), 138.1 (CCl=), 127.3 (C2), 115.7 (=CH2), 99.1 (C2').

Method B

To a solution of Example 8 (20.42 g) in tetrahydrofuran (400 ml) 1.005 N aqueous potassium hydroxide solution (40.15 ml) was added dropwise and the mixture stirred at 25° C. (jacket temperature) for 0.5 hours. The reaction was heated (85° C. jacket temperature) and acetonitrile (1.5 L) was added dropwise while solvent was removed by distillation. Once the acetonitrile was added (4 hours) more solvent was removed by distillation (95° C. jacket temperature) until a final reaction volume of 550 ml. The solution was cooled to 5° C. and kept at this temperature for 20 hours. The crystalline solid formed was collected by filtration under nitrogen atmosphere, washed with acetonitrile (50 ml) and dried under vacuum oven (40° C.) to yield the title compound (18.25 g) as a white crystalline solid.

EXAMPLE 10

[1R-(1α,3aβ,4β,4aβ,7β,7aα,8aβ)]8a-[(2R,6R)-(4-(3,3-difluoroallyl)-6-methyl-morpholin-2-yl)-oxymethyl]-4-formyl-4,4a,5,6,7,7a,8,8a-octahydro-7-methyl-3-(1-methylethyl)-1,4-methano-s-indacene-3a(1H)-carboxylic acid A solution of Intermediate 9 (300 mg; 0.54 mmol) in tetrahydrofuran (16 ml) was treated with 50% v/v solution of 1N hydrochloric acid in tetrahydrofuran (24 ml) and stirred for 3 hours. The mixture was diluted with ethyl acetate (30 ml) and washed with brine (2×30 ml). Evaporation of the solvent gave the title compound (291 mg).

$^1$H-NMR (CDCl₃, ppm): 13.45 (br s, 1H, CO₂H), 9.70 (s, 1H, CHO), 6.09 (dd, 1H, H-2, J=1.2 and 3.3 Hz), 5.00 to 3.00 (m, 8H, 8a-CH₂, H-2', 6', allyl-CH₂—N, 2×CH—N)

EXAMPLE 11

[1R-(1α,3aβ,4β,4aβ,7β,7aα,8aβ)18a-[(2R,6R)-(4,6-dimethyl-morpholin-2-yl)-oxymethyl]-4-formyl-4,4a,5,6,7,7a,8,8a-octahydro-7-methyl-3-(1-methylethyl)-1,4-methano-s-indacene-3a(1H)-carboxylic acid Intermediate 13 (150 mg) was dissolved in ethyl acetate (15 ml) and 5% Pd(C) (≈30 mg) was added. The reaction bottle was connected to a PARR hydrogenation apparatus with a H₂ pressure of 35 P.S.I. and shaken for 2 hours following the reaction evolution by t.l.c. (hexane/acetone v/v 2:1). The reaction crude was filtered through Celite in order to eliminate the catalyst; then, the solvent was evaporated under vacuum and the residue was purified by column. chromatography (hexane/acetone v/v from 4:1 to 2:1) to give the title compound (102 mg).

$^1$H-NMR (CDCl₃, ppm): 9.83 (s, 1H, CHO); 6.00 (dd, 1H, H2, J=1.2 and 3.6 Hz); 4.53 (dd, 1H, H2', J=1.8 and 9.0 Hz); 3.85 (m, 2H, H6'+8a CHa); 3.78 (d, 1H, 8aCHb, J=9.0 Hz); 2.85 (2bd, 2H, H3'+H5', J=12.0 Hz); 2.67 (t, 1H, H1, J=3.6 Hz); 2.41 (s, 3H, CH3—N); 2.32 (m, 1H, C$\underline{H}$(CH₃)₂).

EXAMPLE 12

[1R-(1α,3aβ,4β,4aβ,7β,7aα,8aβ)]8a-[(2R,6R)-6-methyl-4-(2-methyl-2-propenyl)-morpholin-2-yl)-oxymethyl]-4-formyl-4,4a,5,6,7,7a,8,8a-octahydro-7-methyl-3-(1-methylethyl)-1,4-methano-s-indacene-3a(1H)-carboxylic acid Intermediate 16 (18 g) was dissolved in commercial tetrahydrofuran (300 ml) and 1N hydrochloric acid (150 ml) was added dropwise at 25° C. over a period of 5 minutes. Once the reaction was completed (TLC controls/dichloromethane/methanol v/v 20:1) 1N sodium hydroxide (200 ml) was added dropwise over 5 minutes.

Removal of tetrahydrofuran at 50° C. under nitrogen gave a mixture to which was added water (50 ml) and commercial acetonitrile (50 ml). Slow addition of hydrochloric acid until pH=7–7.5 promoted the precipitation of a white solid which was washed with water, dried by suction for 6 hours then at the vacuum oven (40° C.) overnight to give the title compound (15 g) as a white powder.

$^1$H-NMR (δ, ppm, CDCl₃): 9.85 (s, 1H, CHO), 6.05 (dd, 1H, H2, J=1.2 and 3.6 Hz), 4.89 (bs, 2H, =CH₂), 4.49 (dd, 1H, H2', J=2.4 and 8.7 Hz), 4.34 (d, 8aCH$_2$, J=9.6 Hz), 3.69 (m, 1H, H6'), 3.44 (d, 1H, 8aCH$_2$, J=9.6 Hz), 2.89 (bd, NCH$_2$, J=2.1 Hz), 2.85 (bd, 1H, H3', J=11.1 Hz), 2.63 (bd, 1H, H5', J=11.1 Hz), 2.51 (t, 1H, H1, J=3.9 Hz), 2.31(sp, 1H, CH(CH$_3$)$_2$, J=6.9 Hz), 1.73 (s, 3H, =C—CH$_3$).

EXAMPLE 13

[1R-(1α,3aβ,4β,4aβ,7β,7aα,8aβ)]8a-[(2R,6R)-6-methyl-4-(2-methyl-2-propenyl)-morpholin-2-yl)-oxymethyl]-4-formyl-4,4a,5,6,7,7a,8,8a-octahydro-7-methyl-3-(1-methylethyl)-1,4-methano-s-indacene-3a(1H)-carboxylic acid potassium salt In a 500 ml round bottom three necked flash was placed a solution of Example 12 (8.4 g) in commercial tetrahydrofuran (100 ml). To this solution was added dropwise 1.005N potassium hydroxyde in water (17.23 ml). The solution was heated up to 90° C. (jacket temperature) until tetrahydrofuran started to distil. At that moment, the dropwise addition of commercial acetonitrile, started and continued until the vapours temperature was 78° C. The hot solution was cooled down to ambient temperature, then introduced in the fridge overnight.

Filtration under nitrogen, washing with acetonitrile (50 ml) and drying at the vacuum oven (40° C.) gave the title compound (8.1 g) as a white powder.

$^1$H-NMR (δ, DMSO-d$_6$): 9.74 (s, 1H, CHO), 5.77 (dd, 1H, H1, J=0.9 and 3.3 Hz), 4.83 (bs, 2H, =CH$_2$), 4.21 (dd, 1H, H2', J=2.1 and 8.7 Hz), 3.93 (d, 1H, 8aCH$_2$, J=9.6 Hz), 3.53 (m, 2H, 8aCH$_2$+H6'), 2.77 (bs, 1H, NCH$_2$), 2.62 (bd, 1H, H3', J=10.2 Hz), 2.54 (bd, 1H, H5', J=10.5 Hz), 2.40 (m, 2H, H1+CH(CH$_3$)$_2$).

$^{13}$C-NMR (δ, DMSO-d$_6$): 206.5 (CHO), 173.0 (CO$_2$), 151.7 (C3), 142.1(=$\underline{C}$CH$_3$), 127.4 (C2), 113.1 (=$\underline{C}$H$_2$), 99.3 (C2'), 68.9 (C6'), 58.5 and 56.9 (C3', 5'), 56.6 (N$\underline{C}$H$_2$), 20.5 ($\underline{C}$H$_3$C=).

EXAMPLE 14

[1R-(1α,3aβ,4β,4aβ,7β,7aα,8aβ)]8a-[(2R,6R)-4-(2,3-butadienyl)-6-methyl-morpholin-2-yl)-oxymethyl]-4-formyl-4,4a,5,6,7,7a,8,8a-octahydro-7-methyl-3-(1-methylethyl)-1,4-methano-s-indacene-3a(1H)-carboxylic acid To a solution of Intermediate 15 (0.22 g) in dry acetonitrile (30 ml) were added camphorsulphonic acid (0.12 g) and paraformaldehyde (75 mg). To this mixture was added propargyltrimethylsilane (68.1 mg), then it was heated up to 70° C. in an oil bath.

After two hours of heating the reaction was cooled down to ambient temperature filtered and concentrated to dryness. The residue was dissolved in tetrahydrofuran (5 ml) and 1N sodium hydroxide was added onto it (5 ml). 1N Hydrochloric acid was added dropwise until pH=6.2 and the precipitate filtered of and dried at the vacuum oven (40° C.) overnight to give the title compound (0.21 g) as a whitish powder.

$^1$H-NMR (δ, ppm, CDCl$_3$): 9.82 (s, 1H, CHO), 6.03 (bd, 1H, H2, J=2.7 Hz), 5.20 (qp, 1H, =CH=, J=7.2 Hz) 4.77 (m, 2H, =CH$_2$), 4.50 (dd, 1H, H2', J=1.8 and 8.7 Hz), 4.05 (d, 1H, 8aCH$_2$, J=9.3 Hz), 3.77 (m, 1H, H6'), 3.65 (d, 1H, 8aCH$_2$, J=9 Hz), 3.14 (m, 2H, NCH$_2$), 2.94 (bd, 1H, H3', J=10.5 Hz), 2.80 (bd, 1H, H5', J=10.8 Hz), 2.62 (t, 1H, H1, J=3.9 Hz), 2.31 (m, 1H, CH(CH$_3$)$_2$).

EXAMPLE 15

[1R-(1α,3aβ,4β,4aβ,7β,7aα,8aβ)]8a-[(2R,6R)-6-methyl-4-(2,3-butadienyl)-6-methyl-morpholin-2-yl)-oxymethyl]-4-formyl-4,4a,5,6,7,7a,8,8a-octahydro-7-methyl-3-(1-methylethyl)-1,4-methano-s-indacene-3a(1H)-carboxylic acid potassium salt To a solution of Example 14 (185 mg) in methanol (10 ml) was added dropwise 0.2 N potassium hydroxide (1.87 ml), the solvents were removed to dryness under vacuum and the residue dissolved in water (5 ml) and freeze dried. 198 mg of the title compound were obtained.

$^1$H-NMR (δ, ppm, DMSO-d$_6$): 9.08 (s, 1H, CHO), 6.07 (bd, 1H, H2, J=2.4 Hz), 5.13 (qp, 1H, =CH=, J=6.9 Hz) 4.73 (m, 2H, =CH$_2$), 4.40 (dd, 1H, H2', J=2.1 and 8.7 Hz), 4.01 (d, 1H, 8aCH$_2$, J=9.3 Hz), 3.67 (m, 2H, 8aCH$_2$+H6'), 3.04 (m, 2H, NCH$_2$), 2.87 (bd, 1H, H3', J=10.5 Hz), 2.74 (t, 1H, H1, J=3.9 Hz), 2.68 (bd, 1H, H5', J=10.5 Hz), 2.46 (m, 1H, CH(CH$_3$)$_2$).

EXAMPLE 16

[1R-(1α,3aβ,4β,4aβ,7β,7aα,8β)]8a-[(2R,6R)4-(4-methoxybenzyl)-6-methyl-morpholin-2-yl)-oxymethyl]-4-formyl-4,4a,5,6,7,7a,8,8a-octahydro-7-methyl-3-(1-methylethyl)-1,4-methano-s-indacene-3a(1H)-carboxylic acid Intermediate 17 (18 g) was dissolved in commercial THF (350 ml) and 1N hydrochloric acid (150 ml) was added dropwise onto it. The solution was stirred at room temperature until completion and 1N sodium hydroxy (250 ml) was added onto it.

The solution was concentrated at 50° C. under nitrogen until 400 ml and the resulting solution diluted with acetonitrile (40 ml), filtered and acidified until pH=7.5 by slow addition of 1N hydrochloric acid.

The white solid thus obtained was collected by filtration, washed with a mixture acetonitrile/water v/v 1:2 and dried under vacuum to afford the title compound (15.5 g) as a white powder.

$^1$H-NMR (δ, ppm, CDCl$_3$): 9.88 (s, 1H, CHO), 7.24 (m, 2H, 2ArH), 6.85 (m, 2H, 2ArH), 6.01 (dd, 1H, H2, J=1.5 and 3.6 Hz), 4.48 (dd, 1H, H2', J=1.5 and 8.7 Hz), 4.11 (d, 1H, 8aCH$_2$, J=9.3 Hz), 3.80 (s, 3H, OCH$_3$), 3.75 (m, 1H, H6'), 3.63 (d, 1H, PhCH$_2$, J=12.9 Hz), 3.53 (d, 1H, 8aCH$_2$, J=9.3 Hz), 3.47 (d, 1H, PhCH$_2$, J=12.9 Hz), 2.82 (bd 1H, H3', J=10.5 Hz), 2.72 (bd, 1H, H5', J=11.1 Hz), 2.53 (t, 1H, H1, J=4.2 Hz), 2.31 (m, 1H, CH(CH$_3$)$_2$).

EXAMPLE 17

[1R-(1α,3aβ,4β, 4aβ,7β,7aα,8aβ)]8a-[(2R,6R)-4-(4-methoxybenzyl)-6-methyl-morpholin-2-yl)-oxymethyl]-4-formyl-4,4a,5,6,7,7a,8,8a-octahydro-7-methyl-3-(1-methylethyl)-1,4-methano-s-indacene-3a(1H)-carboxylic acid potassium salt In a 250 ml round bottton three necked flask was placed a solution of Example 16 (3.85 g) in commercial tetrahydrofuran (50 ml). To this solution was added dropwise 1.005 N potassium hydroxyde in water (6.94 ml).

The solution was heated until tetrahydrofuran started to distil. At that moment the dropwise addition of commercial acetonitrile started, and continued until the vapours temperature was 78° C. (final volume=65 ml), then cooled down to ambient temperature.

The suspension was introduced in the fridge and kept overnight, then filtered-off, the solid washed with acetonitrile (50 ml) and dried at the vacuum oven (40° C.) overnight to give the title compound (3.87 g) as a white powder.

$^1$H-NMR (δ, ppm, DMSO-d$_6$): 9.74 (s, 1H, CHO), 7.17 (m, 2H, 2ArH), 6.86 (m, 2H, 2ArH), 5.74 (bd, 1H, H2, J=2.4 Hz), 4.20 (dd, 1H, H2', J=1.8 and 8.4 Hz), 3.93 (d, 1H, 8aCH$_2$, J=9.3 Hz), 3.72 (s, 3H, OCH$_3$), 3.50 (m, 2H, H6'+8aCH$_2$), 2.61 (bd, 1H, H3', J=10.2 Hz), 2.55 (bd, 1H, H5', J=10.5 Hz), 2.38 and 2.33 (2m, 2H, CH(CH$_3$)$_2$+H1).

$^{13}$C-NMR (δ, ppm, DMSO-d$_6$): 206.6 (CHO), 172.8 (CO$_2$$^-$), 158.3 (CH$_3$OAr), 151.8 (C3), 130.2 (C(Ar)H), 129.3 (C(Ar)CH$_2$N), 127.3 (C2), 113.5 (C(Ar)H), 99.2 (C2'), 68.8 (C6'), 58.3 and 56.9 (C3',5'), 56.2 (CH$_2$N), 54.9 (CH$_3$O).

EXAMPLE 18

1R-(1α,3aβ,4β,4aβ,7β,7aα,8aβ)]8a-[(2R,6R)-6-methyl-4-methoxy-morpholin-2-yl)-oxymethyl]-4-formyl-4,4a,5,6,7,7a,8,8a-octahydro-7-methyl-3-(1-methylethyl)-1,4-methano-s-indacene-3a(1H)-carboxylic acid To a solution of Intermediate 3 (0.25 g) in dry methanol (5 ml) were added solid methylhydroxylamine hydrochloride (77.5 mg) and triethylamine (209 ml) at once. The mixture was stirred at room temperature for 2 hours, then concentrated to dryness.

The residue was dissolved again in dry methanol (5 ml) and sodium cyanoborohydride (48 mg) and acetic acid (60 ml) were added consecutively. After 2 hours stirring an additional amount of 60 ml of acetic acid was added and the mixture stirred at ambient temperature overnight. Water (10 ml) and ethyl acetate (10 ml) were added and the two phases partitioned the organic layer was washed with brine (2×50 ml) and dried over sodium sulphate.

Elimination of the solvent gave a crude which was purified by filtration through a short pad of silica gel, which was eluted with hexane/acetone v/v 20:1.

0.154 g of a foam were obtained after elimination of the solvent of the appropriate fractions.

This material was dissolved in dichloromethane (6 ml) and 99% trifluoroacetic acid (0.6 ml) was added onto it.

Once the reaction was concluded (TLC controls, dichloromethane/methano v/v 20:1), 10% aqueous sodium sulphate were added (10 ml) and the phases partitioned. The organic was washed with 10% sodium sulphate, dried over solid sodium sulphate and the solvent removed to dryness.

The crude thus obtained was purified by preparative thin layer chromatography, eluting with a mixture dichloromethane/methanol v/v 10:1 to give the title compound (0.08 g) of GW474531X as a foam.

$^1$H-NMR (δ, ppm, CDCl$_3$, 50° C.): 9.80 (s, 1H, CHO), 6.06 (dd, 1H, H2, J=1.2 and 3.3 Hz), 4.49 (bs, 1H, H2'), 4.22 (d, 1H, 8aCH$_2$, J=9.3 Hz), 3.7 (m, 1H, H6'), 3.5 (d, 1H, 8aCH$_2$, J=9.6 Hz), 3.50 (s, 3H, OCH$_3$), 3.33 (bd, 1H, H3', J=10.8 Hz), 3.13 (bd, 1H, H5', J=10.8 Hz).

EXAMPLE 19

[1R-(1α,3aβ,4β,4aβ,7β,7aα,8aβ)]8a-[(2R,6R)-4-(2-chloroallyloxy)-6-methylmorpholin-2-yloxymethyl]-4-formyl-4,4a,5,6,7,7a,8,8a-octahydro-7-methyl-3-(1-methylethyl)-1,4-methano-s-indacene-3a(1H)-carboxylic acid To a solution of Example 8 (202 mg) in dichloromethane (20 ml) at −10° C. 108 mg of 70% 3-chloroperoxybenzoic acid were added and the mixture was stirred at −10° C. for 1 hour. The solvent was removed under vacuum and the residue dissolved in acetonitrile (30 ml) and refluxed for 4 hours. The reaction was cooled, evaporated to dryness and partitioned between ethyl acetate (100 ml) and 10% aqueous sodium hydrogen carbonate solution (50 ml). The organic layer was washed with 10% aqueous sodium hydrogen carbonate solution (50 ml), water and brine, then dried and evaporated. The residue was chromatographed (silica gel, dichloromethane/methanol 100:1) to yield, after evaporation and crystallization from pentane, the title compound (120 mg).

$^1$H-NMR (δ, ppm, CDCl$_3$): 9.8 (s, 1H, CHO), 6.06 (dd, 1H, H-2, J=1.5 and 3.6 Hz), 5.44–5.36 (m, 2H, N—O—C—C(Cl)=CH$_2$), 4.4 (bs, 1H, H-2'), 4.354.2 (m, 3H, 8aCHa and N—O—CH$_2$—C(Cl)=C), 3.6 (bs, 1H, H-6'), 3.47 (bd, 1H, 8aCHb, J=9.3 Hz), 3.37 and 3.15 (2bs, 2H, Ha-3' and Ha-5'), 2.57 (m, 1H, H-1).

EXAMPLE 20

[1R-(1α,3aβ,4β,4aβ,7β,7aα,8aβ)]8a-[(2R,6R)-4-allyloxy-6-methylmorpholin-2-yloxymethyl]-4-formyl-4,4a,5,6,7,7a,8,8a-octahydro-7-methyl-3-(1-methylethyl)-1,4-methano-s-indacene-3a(1H)-carboxylic acid To a solution of Example 2 (552 mg) in dichloromethane (40 ml) at −10° C. 317 mg of 70% 3-chloroperoxybenzoic acid were added and the mixture was stirred at −10° C. for 1 hour. The solvent was removed under vacuum and the residue dissolved in a 1:1 mixture of acetonitrile:tetrahydrofuran (100 ml) and refluxed for 5 days. The reaction was cooled, evaporated to dryness and partitioned between ethyl acetate (150 ml) and 10% aqueous sodium hydrogen carbonate solution (50 ml). The organic layer was washed with 10% aqueous sodium hydrogen carbonate solution (50 ml), water and brine, then dried and evaporated. The residue was chromatographed (silica gel, dichloromethane:methanol 100:1) to yield, after evaporation and crystallization from pentane, the title compound (260 mg).

$^1$H-NMR (δ, ppm, CDCl$_3$): 9.8 (s, 1H, CHO), 6.06 (dd, 1H, H-2, J=1.5 and 3.6 Hz), 6–5.8 (m, 1H, N—O—C—C H=C), 5.3–5.15 (m, 2H, N—O—C—C=CH$_2$), 4.4 (bs, 1H, H-2'), 4.27 (bd, 1H, 8aCHa, J=9 Hz), 4.18 (d, 2H, N—O—CH$_2$—C=C, J=6 Hz), 3.6 (bs, 1H, H-6'), 3.47 (bd, 1H, 8aCHb, J=9.3 Hz), 3.34 and 3.11 (2bs, 2H, Ha-3' and Ha-5'), 2.57 (bt, 1H, H-1, J=3.9 Hz).

EXAMPLE 21

[1R-(1α,3aβ,4β,4aβ,7β,7aα,8aβ)]8a-[(2R)-(4-methyl-6-ethyl-morpholin-2-yl)-oxymethyl]-4-formyl-4,4a,5,6,7,7a,8,8a-octahydro-7-methyl-3-(1-methylethyl)-1,4-methano-s-indacene-3a(1H)-carboxylic acid Intermediate 20 (150 mg) was dissolved in ethyl acetate (35 ml) and 10% Pd(C) (≈70 mg) was added. The reaction bottle was connected to a PARR: hydrogenation apparatus with a hydrogen pressure of 35 P.S.I. and shaken for 4 hours following the reaction evolution by t.l.c. (hexane/acetone v/v 2:1). The reaction crude was filtered through Celite in order to eliminate the catalyst; then, the solvent was evaporated under vacuum and the residue was purified by, column chromatography (dichloromethane/methanol v/v 20:1) to give the title compound (102 mg).

$^1$H-NMR (DMSO, ppm): 9.61 and 9.59 (s, 1H, CHO); 6.05 (m, 2H, H2); 4.39 and 4.29 (dd, 1H, H2', J=2.1 and 8.7 Hz); 4.04 and 3.74 (d, 1H, 8aCHa, J=9.3 Hz); 3.64 and 3.36 (d, 1H, 8aCHb, J=9.3 Hz); 3.40–3.25 (m, 2H, H6'); 2.85–2.50 (m, 6H, H3'+H5'+H1); 2.11 (s, 6H, CH$_3$—N).

EXAMPLE 22

[1R-(1α,3aβ,4β,4aβ,7β,7aα,8aβ)]8a-[(2R)-(4-methyl-6-tert-butyl-morpholin-2-yl)-oxymethyl]-4-formyl-4,4a,5,6,7,7a,8,8a-octahydro-7-methyl-3-(1-methylethyl)-1,4-methano-s-indacene-3a(1H)-carboxylic acid sodium salt Intermediate 22 (68 mg) was dissolved in ethyl acetate (10 ml) and 10% Pd(C) (≈30 mg) was added. The reaction bottle was connected to a PARR hydrogenation apparatus with a hydrogen pressure of 35 P.S.I. and shaken for 2 hours following the reaction evolution by t.l.c. (hexanelacetone v/v 2:1). The reaction crude was filtered through Celite in order to eliminate the catalyst; then, the solvent was evaporated under vacuum and the residue was purified by column chromatography (first, hexane/ethyl acetate 3:1; then, dichloromethane/methanol v/v 10:1) to give a compound (48 mg) which was converted into the title compound (48 mg) by treatment with 0.0955N sodium hydroxide (1.026 ml) and lyophilization.

$^1$H-NMR (DMSO, ppm): 9.76 and 9.73 (s, 1H, CHO); 5.81 (m, 2H, H2); 4.27 and 4.23 (dd, 1H, H2', J=2.1 and 8.7 Hz); 4.05 and 3.87 (d, 1H, 8aCHa, J=9.6 Hz); 3.71 and 3.58 (d, 1H, 8aCHb, J=9.6 Hz); 3.06 and 3.03 (t, 1H, H1, J=2.1 Hz); 2.70–2.35 (m, 4H, H3'+H5'); 2.13 (s, 6H, C$\underline{H}_3$—N).

EXAMPLE 23

[1R-(1α,3β,4β,4aβ,7β,7aα,8aβ)]8a-[(2R)-(4-methyl-6-phenyl-morpholin-2-yl)-oxymethyl]-4-formyl-4,4a,5,6,7,7a,8,8a-octahydro-7-methyl-3-(1-methylethyl)-1,4-methano-s-indacene-3a(1H)-carboxylic acid sodium salt Intermediate 25 (100 mg) was dissolved in ethyl acetate (10 ml) and 10% Pd(C). (≈30 mg) was added. The reaction bottle was connected to a PARR hydrogenation apparatus with a hydrogen pressure of 35 P.S.I. and shaken for 2 hours following the reaction evolution by t.l.c. (hexane/acetone v/v 2:1). The reaction crude was filtered through Celite in order to eliminate the catalyst; then, the solvent was evaporated under vacuum and the residue was purified by column chromatography (hexane/ethyl acetate v/v from 1:1 to 1:3) to give a compound (57 mg) which was converted into the title compound (55 mg) by treatment with 0.0955N sodium hydroxide (0.973 ml) and lyophilization.

$^1$H-NMR (DMSO, ppm): 9.79 and 9.77 (s, 1H, CHO); 7.70–7.10 (m, 10H, Ph) 5.85–5.80 (m, 2H, H2); 4.51 and 4.44 (dd, 1H, H2', J=2.1 and 8.7 Hz); 4.06 and 4.01 (d, 1H, 8aCHa, J=9.6 Hz); 3.65 and 3.62 (d, 1H, 8aCHb, J=9.6 Hz); 3.50–3.25 (m, 6H, H3'+H1+H5'); 2.18 (s, 6H, C$\underline{H}_3$—N).

EXAMPLE 24

[1R-(1α,3β,4β,4aβ,7β,7aβ,8aβ)]8a-[(2R,6R)-6-methyl-4-(2-fluoromethyl-2-propenyl)-morpholin-2-yl]-oxymethyl]-4-formyl-4,4a,5,6,7,7a,8,8a-octahydro-7-methyl-3-(1-methylethyl)-1,4-methano-s-indacene-3a(1H)-carboxylic acid, potassium salt Intermediate 29 (234 mg) was dissolved in dichloromethane (20 ml) and trifluoroacetic acid (0.5 ml) was added. The reaction mixture was stirred at room temperature for 30 minutes following the reaction course by t.l.c. (hexane-ethyl acetate v/v 3:1). The reaction crude was diluted using dichloromethane and extracted with 10% sodium sulphate; the organic layer was taken, dried over sodium sulphate and evaporated to dryness. The residue was purified by column chromatography (first, hexane-ethyl acetate v/v 3:1; then, dichloromethane-methanol v/v 10:1) and the compound obtained (123 mg) was treated with 0.203 N KOH (1.04 ml) and lyophilized to give the title compound (122 mg).

$^1$H-NMR (δ, DMSO): 9.75 (s, 1H, CHO); 5.76 (dd, 1H, J=1.2 and 3.6 Hz, H2); 5.20 (s, 1H, $\underline{H}$—C=); 5.15 (s, 1H, $\underline{H}$—C=); 4.85 (d, 2H, J=47.4 Hz, CH$_2$—F); 4.21 (dd, 1H, J=2.4 and 8.7 Hz, H2'); 3.94 (d, 1H, J=9.3 Hz, 8aCH$_2$); 3.80–3.70 (m, 2H, 8aCH$_2$+H6'); 2.91 (s, 2H, CH$_2$—N).

EXAMPLE 25

[1R-(1α,3β,4β,4aβ,7β,7aα,8aβ)]8a-[(2R,6R)-(4-allyl-6-methyl-morpholin-2-yl)-oxymethyl]-4-cyano4,4a,5,6,7,7a,8,8a-octahydro-7-methyl-3-(1-methylethyl)-1,4-methano-s-indacene-3a(1H)-carboxylic acid Acetic anhydride (12 ml) was added to Intermediate 30 (0.18 g) and the mixture was stirred at 90° C. for 4 hours. Crude reaction mixture was concentrated under vacuum and coevaporated with toluene. The residue thus obtained was chromatographed on silica using 2% methanol in dichloromethane to afford the title compound (0.14 g).

$^1$H-NMR (δ, ppm, CDCl$_3$): 6.12 (dd, 1H, H-2, J=1.2 and 3.3 Hz), 5.95 (m, 1H, HC=C), 5.3 (m, 2H, H$_2$C=C), 4.55 (dd, 1H, H-2', J=2.1 and 9.0 Hz), 3.9 (m, 1H, H-6'), 3.84 and 3.75 (2d, 2H, 8a-CH$_2$, J=9.0 Hz), 3.21 (m, 2H, CH$_2$—N), 3.00 (d, 1H, 3'-Ha, J=10.5 Hz), 2.90 (1H, 5'-Ha, J=10.5 Hz), 2.71 (m, 2H, C$\underline{H}$(CH$_3$)$_2$ and H-1).

$^{13}$C-NMR (δ, ppm, CDCl$_3$): 173.5 (COOH), 149.7 (C-3), 131.5 and 130.9 (C-2 and H$\underline{C}$=C), 123.2 (CN), 121.5 (H$_2$$\underline{C}$=C), 98.6 (C-2'), 68.5 (C-6'), 60.2, 56.7 and 54.5 (3 CH$_2$N).

EXAMPLE 26

[1R-(1α,3β,4β,4aβ,7β,7aα,8aβ)]8a-[(2R,6R)-(4-allyl-6-methyl-morpholin-2-yl)-oxymethyl]-4-cyano-4,4a,5,6,7,7a,8,8a-octahydro-7-methyl-3-(1-methylethyl)-1,4-methano-s-indacene-3a(1H)-carboxylic acid, potassium salt To a solution of Example 25 (82 mg) in methanol, 0.199 N aqueous potassium hydroxide (0.88 ml) was added dropwise. The solvent was removed under reduced pressure and the residue was dissolved in water (10 ml) and lyophilized to give the title compound (85 mg).

$^1$H-NMR (δ, ppm, DMSO-d$_6$): 5.90 (dd, 1H, H-2, J=0.9 and 3.0 Hz), 5.77 (m, 1H, HC=C), 5.16 and 5.11 (2dd, 2H, H$_2$C=C, J=2.1 and 17.4 Hz and J=2.1 and 9.9 Hz), 4.21 (dd, 1H, H-2', J=2.1 and 8.4 Hz), 3.89 and 3.51 (2d, 2H, 8a-CH$_2$, J=9.6 Hz), 3.52 (m, 1H, H-6'), 2.89 (d, 2H, CH$_2$N, J=6.3 Hz), 2.66 (m, 2H, 3'-Ha and C$\underline{H}$(CH$_3$)$_2$), 2.60 (d, 1H, 5'Ha, J=9.9 Hz), 2.40 (t, 1H, H-1, J=3.6 Hz).

EXAMPLE 27

[1R-(1α,3β,4β,4aβ,7β,7aα,8aβ)]8a-[(2R,6R)-6-methyl-4-(1-methylpyrrol-2-ylmethyl)morpholin-2-yl)-oxymethyl]-4-formyl-4,4a,5,6,7,7a,8,8a-octahydro-7-methyl-3-(1-methylethyl)-1,4-methano-s-indacene-3a(1H)-carboxylic acid hydrochloride A solution of Intermediate 31 (14 mg; 0.02 mmol) in tetrahydrofuran (2 ml) was treated with a 50% v/v solution of 1N hydrochloric acid in tetrahydrofuran (3 ml). After stirring at room temperature for 5 hours the mixture was diluted with ethyl acetate (3 ml) and washed with brine (2×3 ml). Evaporation of the solvent gave the title compound (10 mg).

$^1$H-NMR (δ ppm, CDCl$_3$): 9.67 (s, 1H, CHO), 6.72 (m, 1H, pyrrolic H-5), 6.04 (m, 3H, H-2 and pyrrolic H-3 and 4), 4.46 (br d, 1H, H-2'), 3.94 (AB system, 1H, 8a-CH$_2$), 3.89 (br s, H-6'), 3.7 (AB system, 1H, 8a-CH$_2$), 3.66 (s, 3H, N—Me).

EXAMPLE 28

[1R-(1α,3β,4β,4aβ,7β,7aα,8aβ)]8a-[(2R,6R)-6-methyl-4[(E)-2-buten-1-yl]morpholin-2-yl)-oxymethyl]-4-formyl-4,4a,5,6,7,7a,8,8a-octahydro-7-methyl-3-(1-methylethyl)-1,4-methano-s-indacene-3a(1H)-carboxylic acid A solution of Intermediate 32 (130 mg; 0.24 mmol) in tetrahydrofuran (2 ml) was treated with 50% v/v solution of 1N hydrochloric acid in tetrahydrofuran (9 ml) and stirred for 3 hours. The mixture was diluted with ethyl acetate (3 ml) and washed with brine (2×3 ml). Evaporation of the solvent and purification by preparative thin layer chromatography using 4% methanol in dichloromethane gave the title compound (91 mg).

$^1$H-NMR (δ, ppm, CDCl$_3$): 9.86 (s, 1H, CHO), 6.01 (dd, 1H, H-2, J=1.2 and 3.3 Hz), 5.70 (m, 1H, butenyl), 5.54 (m, 1H, butenyl), 4.54 (dd, 1H, H-2', J=2.4 and 8.4 Hz), 3.95 (AB system, 1H, 8a-CH$_2$), 3.85 (m, H6'), 3.72 (AB system, 1H, 8a-CH$_2$), 3.2 to 2.8 (m, 6H, allyl-CH$_2$—N+2×CH—N).

EXAMPLE 29

[1R-(1α,3aβ,4β,4aβ,7β,7aα,8aβ)]8a-[(2R,6R)-6-methyl-4-(4-bromobenzyl)morpholin-2-yl)-oxymethyl]-4-formyl-4,4a,5,6,7,7a,8,8a-octahydro-7-methyl-3-(1-methylethyl)-1,4-methano-s-indacene-3a(1H)-carboxylic acid trifluoacetate salt A solution of Intermediate 33 (80 mg; 0.1 mmol) in 5% v/v trifluoroacetic acid in dichloromethane (5 ml) was stirred at room temperature for 24 hours. The solvent was evaporated and the resulting residue was purified by column chromatography using 1:2 ethyl acetate/hexane to afford the title compound (44 mg)

$^1$H-NMR (δ, ppm, CDCl$_3$): 9.70 (s, 1H, CHO), 7.55 (AB system, 2H, 4-BrBn), 7.25(AB system, 2H, 4-BrBn), 6.02 (dd, 1H, H-2, J=1.2 and 3.3 Hz), 4.64 (dd, 1H, H-2', J=2.4 and 8.7 Hz), 4.01 (AB system, 2H, BnCH$_2$N), 3.99 (AB system, 1H, 8a-CH$_2$), 3.96 (m, 1H, H-6'), 3.67 (AB system, 1H, 8a-CH$_2$), 3.21 (m, 2H, 2×CHN).

EXAMPLE 30

[1R-(1α,3aβ,4β,4aβ,7β,7aα,8aβ)]8a-[(2R,6R)-6-methyl-4-(4-bromobenzyl)morpholin-2-yl)-oxymethyl]-4-formyl)-4,4a,5,6,7,7a,8,8a-octahydro-7-methyl-3-(1-methylethyl)-1,4-methano-s-indacene-3a(1H)-carboxylic acid A solution of Example 29 (44 mg; 0.07 mmol) in dichloromethane (2 ml) was washed with 10% sodium sulfate (2 ml). The organic layer was washed with brine (5 ml), dried (sodium sulfate) and evaporated to give the title compound (24 mg).

$^1$H-NMR (δ, ppm, CDCl$_3$): 9.83 (brs, 1H, CHO), 7.48 (brAB system, 2H, 4-BrBn), 7.25(AB system, 2H, 4-BrBn), 6.04 (brd, 1H, H-2).

EXAMPLE 31

[1R-(1α,3aβ,4β,4aβ,7β,7aα,8aβ)]8a-[(2R,6R)-6-methyl-4-(2,2,2-trifluoroethyl)morpholin-2-yl)-oxymethyl]-4-formyl-4,4a,5,6,7,7a,8,8a-octahydro-7-methyl-3-(1-methylethyl)-1,4-methano-s-indacene-3a(1H)-carboxylic acid A solution of Intermediate 34 (114 mg; 0.15 mmol) in 5% v/v trifluoroacetic acid in dichloromethane (5 ml) was stirred at room temperature for 3 hours. The solvent was evaporated and the resulting residue was purified by column chromatography using 1:3 ethyl acetate/hexane to afford the title compound (40 mg).

$^1$H-NMR (δ, ppm, CDCl$_3$): 9.77 (s, 1H, CHO), 6.03 (m, 1H, H-2), 4.55 (dd, 1H, H-2', J=2.1 and 8.7 Hz), 4.09 (AB system, 1H, 8a-CH$_2$), 3.80 (m, 1H, H-6'), 3.63 (AB system, 1H, 8a-CH$_2$), 3.05 (br d, 1H, CHN), 2.95 (q, 2H, CF$_3$CH$_2$N, J=9.3 Hz), 2.87 (br d, 1H, CHN).

EXAMPLE 32

[1R-(1α,3aβ,4β,4aβ,7β,7aα,8aβ)]8a-[(2R,6R)-6-methyl-4-(cyclopropylmethyl)morpholin-2-yl)-oxymethyl]-4-formyl-4,4a,5,6,7,7a,8,8a-octahydro-7-methyl-3-(1-methylethyl)-1,4-methano-s-indacene-3a(1H)-carboxylic acid A solution of Intermediate 35 (40 mg; 0.06 mmol) in 5% v/v trifluoroacetic acid in dichloromethane (3 ml) was stirred at room temperature for 3 hours. The solvent was evaporated and the resulting residue was purified by column chromatography using 1:3 ethyl acetateihexane to afford the title compound (16 mg).

$^1$H-NMR (δ, ppm, CDCl$_3$): 9.77 (s, 1H, CHO), 6.03 (m, 1H, H-2), 4.55 (dd, 1H, H-2', J=2.1 and 8.7 Hz), 4.09 (AB system, 1H, 8a-CH$_2$), 3.80 (m, 1H, H-6'), 3.63 (AB system, 1H, 8a-CH$_2$), 3.05 (br d, 1H, CHN), 2.87 (br d, 1H, CHN).

EXAMPLE 33

[1R-(1α,3aβ,4β,4aβ,7β,7aα,8aβ)]8a-[(2R,6R)-6-methyl-4-(4-fluorobenzyl)morpholin-2-yl) oxymethyl]-4-formyl-4,4a,5,6,7,7a,8,8a-octahydro-7-methyl-3-(1-methylethyl)-1,4-methano-s-indacene-3a(1H)-carboxylic acid, trifluoroacetate salt A solution of Intermediate 36 (10 mg; 0.015 mmol) in 10% v/v t1trifluoroacetic acid in dichloromethane (4 ml) was stirred at room temperature for 5 hours. The solvent was evaporated and the resulting residue was purified by column chromatography using 5% methanol in dichloromethane to afford the title compound (4 mg).

$^1$H-NMR (δ, ppm, CDCl$_3$): 9.68 (s, 1H, CHO), 7.41 (m, 2H, 4-F—Bn), 7.13 (m, 2H, 4F—Bn), 6.06 (dd, 1H, H-2, J=1.2 and 3.3 Hz), 4.75 (dd, 1H, H-2', J=2.1 and 8.7 Hz), 4.10 (m, 4H, AB system aCH$_2$+BnCH$_2$N+H-6'), 3.65 (AB system, 1H, 8a-CH$_2$),3.32 (m, 2H, CHN).

EXAMPLE 34

[1R-(1α,3aβ,4β,4aβ,7β,7aα,8aβ)]8a-[(2R,6R)-6-methyl-4-(cyclohexen-3-yl)morpholin-2-yl)-oxymethyl]-4-formyl-4,4a,5,6,7,7a,8,8a-octahydro-7-methyl-3-(1-methylethyl)-1,4-methano-s-indacene-3a(1H)-carboxylic acid A solution of Intermediate 37 (40 mg, 0.072 mmol) in 1:2 v/v 1N hydrochloric acid-tetrahydrofuran mixture (9 ml) was stirred at room temperature for 12 hours. The solution was evaporated and the residue partitioned into ethyl acetate (10 ml) and water (10 ml). The organic layer was dried (magnesium sulfate) and evaporated to dryness. The residue was purified by preparative thin layer chromatography using 5% mehanol in dichloromethane to give the title compound (26 mg).

$^1$H-NMR (δ, ppm, CDCl$_3$): 9.71 (s, 1H, CHO), 6.02 (dd, 1H, H-2, J=1.2 and 3.3 Hz), 5.81 (m, 1H, CH═CH), 5.60 (dd, 1H, CH═CH, J=10.2 and 2.1 Hz), 4.45 (m, 1H, H-2'), 4.06 (AB system, 1H, 8aCH$_2$), 3.70 (m, 1H, H-6'), 3.62 (AB system, 1H, 8aCH$_2$), 3.28 (br s, 1H, CH═CH—CH—N), 2.78 (m, 1H, CHN), 2.62 (m, 2H, H-1+CHN).

EXAMPLE 35

[1R-(1α,3aβ,4β,4aβ,7β,7aα,8aβ)]8a-[(2R,6R)-6-methyl-4-(phenacylmorpholin-2-yl)-oxymethyl]-4-formyl-4,4a,5,6,7,7a,8,8a-octahydro-7-methyl-3-(1-methylethyl)-1,4-methano-s-indacene-3a(1H)-carboxylic acid A solution of Intermediate 40 (100 mg; 0.13 mmol) in 7% v/v trifluoroacetic acid in dichloromethane (4 ml) was stirred at room temperature for 5 hours. The solvent was evaporated and the resulting residue was purified by preparative thin layer chromatography using 5% methanol in dichloromethane to afford the title compound (50 mg).

$^1$H-NMR (δ, ppm, CDCl$_3$): 9.61 (s, 1H, CHO), 7.95 (m, 2H, PhCO), 7.58 (m, 1H, PhCO), 7.47 (m, 2H, PhCO), 7.26 (s, 1H, Ph$_2$CH), 6.05 (br s, 1H, H-2), 4.57 (br d, 1H, H-2'), 4.22 (AB system, 1H, 8a-CH$_2$), 3.71 (m, 8H, OCH$_2$CH$_2$O+ 8a-CH$_2$+COCH$_2$N+H-6'), 3.02 (br d, 1H, CHN), 2.81 (br d, 1H, CH—N), 2.58 (br s, 1H, H-1), 2.36 (m, 1H, (CH$_3$)$_2$CH).

Pharmacy Examples

| 1. Conventional oral tablet* | |
|---|---|
| Drug substance | 100 mg |
| Microcrystalline cellulose | 160 mg |
| Crosscarmellose sodium | 20 mg |
| Magnesium stearate | 5 mg |

The drug substance is blended with microcrystalline cellulose, crosscarmellose sodium and magnesium stearate, then compressed into tablets.

| 2. Conventional Capsule* | |
|---|---|
| Drug substance | 100 mg |
| Lactose | 200 mg |
| Magnesium stearate | 2 mg |

The drug substance is blended with the lactose and the magnesium stearate and then filled into appropriate capsules.

| 3. Chewable oral tablet | |
|---|---|
| Drug substance | 100 mg |
| Xylitol | 865 mg |
| Peppermint flavour | 5 mg |
| Aspartame | 10 mg |
| Polyvinylpyrollidone | 15 mg |
| Magnesium stearate | 5 mg |

The drug substance, xylitol, aspartame and polyvinylpyrollidone are blended together and granulated with water, then dried. This granule is mixed with the peppermint flavour and magnesium stearate, then compressed into tablets.

| 4. Aqueous Oral Solution | |
|---|---|
| Drug substance | 100 mg |
| Hydroxypropylmethyl cellulose | 150 mg |
| Sodium propylhydroxybenzoate | 1 mg |
| Sodium methylhydroxybenzoate | 2 mg |
| Orange flavour | 10 mg |
| Sodium saccharin | 5 mg |
| Sucrose | 800 mg |
| Suitable buffers | qs |
| Purified water to | 5 mls |

Dissolve the drug substance and all the excipients in most of the purified water and mix. Make to volume and mix. Suitable buffers may be added to control the pH in the region of maximum stability.

| 5. Non-Aqueous Oral Suspension | |
|---|---|
| Drug substance | 100 mg |
| Aspartame | 50 mg |
| Grapefruit flavour | 25 mg |
| Mannitol | 800 mg |
| Colloidal silica | 10 mg |
| Fractionated coconut oil | 5 mls |

Disperse the drug. substance and mannitol in the bulk of the fractionated coconut oil by high shear mixing. Add the remaining ingredients and mix. Make to volume with fractionated coconut oil and mix.

| 6. Ointment | |
|---|---|
| Drug substance | 200 mg |
| White Soft Paraffin | 9800 mg |

Melt the white soft paraffin, add the drug and mix. Continue to mix until the ointment starts to congeal.

| 7. Injection | |
|---|---|
| Drug substance | 40 mg |
| Suitable buffers | qs |
| Suitable antioxidants | qs |
| Suitable chelating agents | qs |
| Water for injections to | 2 mls |

Dissolve the drug substance in most of the water for injections. Suitable buffering agents may be added to control the pH to the region of optimum stability. Suitable antioxidants and chelating agents may be added. to improve the stability of the injection. Make to mark with water for injections. Fill into ampoules or vials, then sterilise by autoclaving. Alternatively, sterilise by filtration and fill aseptically.

The tablets and or capsules may be film-coated using conventional procedures known in the art.

Antifungal Activity

Compounds of formula (I) have been tested for anti fungal activity in a standard in vitro screen and the minimum inhibiting concentration (MIC; µg/ml) determined for each compound against a variety of clinically relevant pathogens. The results obtained with representative compounds of the invention are given below.

The compounds of the invention are essentially non-toxic at therapeutically useful levels. For example, the compound of Example 2 when administered orally in a system candidiasis test (C.albicans 4711E) in mice, has an ED$_{50}$ value of 9.0 mg/kg. The LD50 value for the compound of example 2, in female mice is >300 mg/kg iv.

| | Example No. MIC's µg/ml | | | | | | | | | | | |
|---|---|---|---|---|---|---|---|---|---|---|---|---|
| Organism | 1i | 2 | 4 | 6 | 7 | 8 | 10 | 12 | 14 | 16 | 18 | 25 |
| C. albicans 4711E | ≦0.001 | 0.008 | ≦0.001 | 0.008 | ≦0.001 | ≦0.001 | 0.03 | ≦0.001 | ≦0.001 | ≦0.001 | 0.03 | 0.25 |
| C. albicans CL-236 | ≦0.001 | 0.03 | 0.015 | 0.015 | 0.008 | ≦0.001 | 0.06 | ≦0.001 | 0.004 | ≦0.001 | 0.25 | 0.25 |
| C. glabrata 2375E | 1 | 0.5 | 4 | 0.25 | 0.25 | 0.03 | 1 | 0.25 | 0.12 | 0.25 | 8 | 0.5 |
| C. glabrata 522 | 1 | 0.5 | 4 | 0.5 | 0.25 | 0.03 | 1 | 0.25 | 0.12 | 0.25 | 8 | 0.5 |
| C. tropicalis 2808E | 0.008 | 0.03 | 0.06 | 0.06 | 0.008 | ≦0.001 | 0.06 | 0.008 | 0.015 | 0.008 | 1 | 0.5 |
| C. pseudotropicalis 2371E | N.T. | 0.004 | 0.004 | 0.015 | ≦0.001 | ≦0.001 | 0.03 | ≦0.001 | ≦0.001 | ≦0.001 | N.T. | 0.12 |
| C. parapsilosis 2372E | >125 | >125 | >125 | 16 | 4 | 1 | 16 | 1 | 8 | 2 | >125 | >125 |

What is claimed is:

1. A compound of formula (I)

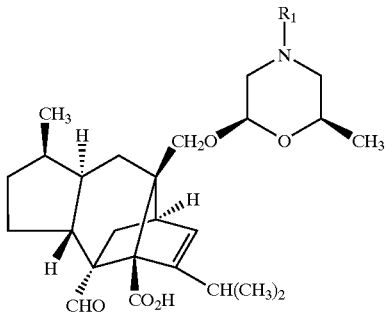

(I)

and physiologically acceptable salts and or metabolically labile derivatives thereof, wherein $R^1$ represents $C_{1-6}$ straight or branched chain alkyl, $C_{1-6}$ straight or branched chain alkoxy, optionally substituted phenoxy, $C_{3-6}$ straight or branched chain alkenyloxy (optionally substituted by 1 or 2 halogen atoms) or $C_{1-4}$ straight or branched alkoxy substituted by an optionally substituted phenyl group, $C_{3-8}$ straight or branched chain alkynyl, $C_{3-6}$ straight or branched chain alkenyl (optionally substituted by $C_{1-4}$alkoxy or 1 or 2 halogen atoms), optionally substituted phenyl, optionally substituted $C_{3-7}$ cycloalkyl, optionally substituted $C_{5-7}$ cycloalkenyl, $C_{2-4}$ straight or branched chain alkyl substituted by ($C_{1-4}$ alkoxy, $C_{1-4}$ alkyl thio or halogen), $C_{1-4}$ straight or branched chain alkyl substituted by ($C_{1-4}$ alkoxycarbonyl, arylalkyloxycarbonyl, aryloxycarbonyl, propadienyl, cyano, optionally substituted $C_{3-7}$ cycloalkyl, optionally substituted 5 or 6 membered heteroaryl, or 1 or 2 optionally substituted phenyl groups), or methyl substituted by $C_{1-6}$ alkanoyl or optionally substituted benzoyl; $R_2$ represents a group selected from hydrogen, $C_{1-6}$ straight or branched chain alkyl, $C_{3-6}$ straight or branched chain alkenyl, optionally substituted phenyl or $C_{1-4}$ alkyl substituted with a group selected from $C_{1-4}$alkoxy, hydroxy, acyloxy, alkoxy carbonyl or aryloxycarbonyl, and $R_3$ represents a group selected from formyl or cyano.

2. Compounds as claimed in claim 1 wherein $R_3$ is formyl.

3. A compound as claimed in claim 1 wherein $R_2$ is methyl.

4. A compound as claimed in claim 3 wherein $R_3$ is formyl and $R_1$ represents a group selected from $C_{1-6}$ straight or branched chain alkyl, $C_{1-6}$ straight or branched chain alkoxy, optionally substituted phenoxy, $C_{3-6}$ straight or branched chain alkenyloxy or $C_{1-4}$ straight or branched alkoxy substituted by an optionally substituted phenyl group, $C_{3-6}$ straight or branched chain alkynyl, $C_{3-6}$ straight or branched chain alkenyl (optionally substituted by $C_{1-4}$alkoxy or 1 or 2 halogen atoms), optionally substituted phenyl, optionally substituted $C_{3-7}$ cycloalkyl, optionally substituted $C_{5-7}$ cycloalkenyl; $C_{2-4}$ straight or branched chain alkyl substituted by ($C_{1-4}$ alkoxy, $C_{1-4}$ alkyl thio or halogen), $C_{1-4}$ straight or branched chain alkyl substituted by ($C_{1-4}$ alkoxycarbonyl, arylalkyloxycarbonyl, aryloxycarbonyl, cyano, optionally substituted $C_{3-7}$ cycloalkyl, optionally substituted 5 or 6 membered heteroaryl, or 1 or 2 optionally substituted phenyl groups), or methyl substituted by $C_{1-6}$ alkanoyl or optionally substituted benzoyl.

5. A compound as claimed in claim 1 wherein $R_1$ is a group selected from $C_{1-6}$alkyl, $C_{1-4}$alkoxy, $C_{3-6}$alkenyloxy, (optionally substitued by halogen), phenyl, $C_{3-6}$cycloalkyl, indanyl, tetrahydronaphthyl, $C_{2-4}$alkyl substituted by $C_{1-2}$alkoxy, $C_{2-4}$alkyl substituted $C_{1-2}$alkylthio, $C_{1-4}$alkyl (substituted by propadienyl, cyano or alkoxycarbonyl), cyclopropylmethyl, furylmethyl, pyridylmethyl, N-methylpyrrolylmethyl, thiazolylmethyl, phenylmethyl, diphenylmethyl, difluorophenylmethyl wherein the two fluorine atoms are in the 2,6, 2,4, 3,4 or 3,5 positions, trifluromethylphenylmethyl, methylenedioxyphenylmethyl, methoxyphenylmethyl, 1-phenylethyl or phenylethyl, $C_{3-6}$ alkenyl, $C_{3-6}$alkynyl, $C_{3-6}$alkenyl substituted by $C_{1-4}$alkoxy, $C_{3-6}$alkenyl substituted 1 or 2 halogen atoms selected from chlorine, bromine or fluorine, cyclohexen-3-yl or methyl substituted by acetyl or benzoyl.

6. A compound as claimed in claim 1 wherein $R_1$ is a group selected from methyl, ethyl, propyl, isopropyl, butyl, 1-methylpropyl, 3-methylbutyl, allyloxy, 2-chloroallyloxy, methoxy, cyclopropyl, allyl, 2-chloroallyl, 2-bromoallyl, 2-methylallyl, 3,3-difluoroallyl, 2,3-butadienyl, phenyl, ethylthioethyl, methoxyethyl, benzyl, furylmethyl, 2,6-difluorophenylmethyl, 3,4-difluorophenylmethyl, 3,5-difluorophenylmethyl, 3,5-difluorophenylmethyl, 3,4-methylenedioxyphenylmethyl, 4-methoxyphenylmethyl, 1-phenylethyl or 2-propynyl.

7. A compound as claimed in claim 1 are those wherein $R_1$ represents 2,3-butadienyl, allyl, 2-methylallyl, 2-chloroallyl, 2-fluoromethylallyl, 2-bromoallyl, 3,3-difluoroallyl, 2-propynyl, cyclopropyl or p-methoxyphenylmethyl.

8. [1R-(1α,3aβ,4β,4aβ,7β,7aα,8aβ)]8a-[(2R,6R)-(4-(2-chloroallyl)-6-methyl-morpholin-2-yl)-oxymethyl]-4-formyl-4,4a,5,6,7,7a,8,8a-octahydro-7-methyl-3-(1-methylethyl)-1,4-methano-s-indacene-3a(1H)-carboxylic acid, and physiologically acceptable salts thereof.

9. A compound selected from;

[1R-(1α,3aβ,4β,4aβ,7β,7aα,8aβ)]8a-[(2R,6R)-(4-(2-methylallyl)-6-methyl-morpholin-2-yl)-oxymethyl]-4- formyl-4,4a,5,6,7,7a,8,8a-octahydro-7-methyl-3-(1-methylethyl)-1,4-methano-s-indacene-3a(1H)-carboxylic acid,

[1R-(1α,3aβ,4β,4aβ,7β,7aα,8aβ)]8a-[(2R,6 R)-(4-(p-methoxybenzyl)-6-methyl-morpholin-2-yl)oxymethyl]-4-formyl-4,4a,5,6,7,7a,8,8a-octahydro-7-methyl-3-(1-methylethyl)-1,4-methano-s-indacene-3a(1H)-carboxylic acid,

[1R-(1α,3aβ,4β,4aβ,7β,7aα,8aβ)]8a-[(2R,6R)-(4-(2,3-butadienyl)-6-methyl-morpholin-2-yl)-oxymethyl]-4-formyl-4,4a,5,6,7,7a,8,8a-octahydro-7-methyl-3-(1-methylethyl)-1,4-methano-s-indacene-3a(1H), carboxylic acid, and physiologically acceptable salts thereof.

10. A compound selected from:

[1R-(1α,3aβ,4β,4aβ,7β,7aα,8aβ)]8a-[(2R,6R)-(4-cyclopropyl-6-methyl-morpholin-2-yl)-oxymethyl]-4-formyl-4,4a,5,6,7,7a,8,8a-octahydro-7-methyl-3-(1-methylethyl)-1,4-methano-s-indacene-3a(1H)-carboxylic acid,

[1R-(1α,3aβ,4β,4aβ,7β,7aα,8aβ)]8a-[(2R,6R)-(4-propylnyl)-6-methyl-morpholin-2-yl)-oxymethyl]-4-formyl-4,4a,5,6,7,7a,8,8a-octahydro-7-methyl-3-(1-methylethyl)-1,4-methano-s-indacene-3a(1H)-carboxylic acid;

[1R-(1α,3aβ,4β,4aβ,7β,7aα,8aβ)]8a-[(2R,6R)-(4-(2-bromoallyl)-6-methyl-morpholin-2-yl)-oxymethyl]-4-formyl-4,4a,5,6,7,7a,8,8a-octahydro-7-methyl-3-(1-methylethyl)-1,4-methano-s-indacene-3a(1H)-carboxylic acid;

[1R-(1α,3aβ,4β,4aβ,7β,7aα,8aβ)]8a-[(2R,6R)-(4-2-allyl-6-methyl-morpholin-2-yl)-oxymethyl]-4-formyl-4,4a,5,6,7,7a,8,8a-octahydro-7-methyl-3-(1-methylethyl)-1,4-methano-s-indacene-3a(1H)-carboxylic acid;

[1R-(1α,3aβ,4β,4aβ,7β,7aα,8aβ)]8a-[(2R,6R)-(4-(3,3-difluoroallyl)-6-methyl-morpholin-2-yl)-oxymethyl]-4-formyl-4,4a,5,6,7,7a,8,8a-octahydro-7-methyl-3-(1-methylethyl)-1,4-methano-s-indacene-3a(1H)-carboxylic acid;

[1R-(1α,3aβ,4β,4aβ,7β,7aα,8aβ)]8a-[(2R,6R)-(4-2-fluoromethylallyl)-6-methyl-morpholin-2-yl)-oxymethyl]-4-formyl-4,4a,5,6,7,7a,8,8a-octahydro-7-methyl-3-(1-methylethyl)-1,4-methano-s-indacene-3a(1H)-carboxylic acid;

and physiologically acceptable salts thereof.

11. A process for the preparation of compounds of formula (I) which comprises:

(a) A process for the preparation of compounds of formula 1 wherein $R_1$ has the meanings defined in claim 1, $R_2$ is methyl and $R_3$ is a formyl group by reacting a compound of formula (II) wherein $R_4$ is hydrogen, a carboxyl protecting group or a cation and $R_3$ is the group CHO or a protected derivative thereof,

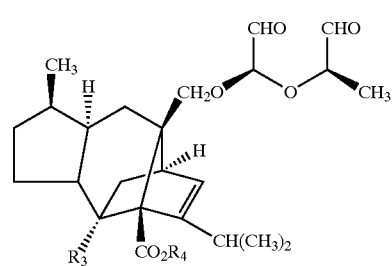

with the amine (III, wherein $R_1$ has the meanings defined above or is a protected derivative thereof), or an acid addition salt thereof,

under reductive amination conditions;

(b) A process for the preparation of compounds of formula (I) wherein $R_2$ is methyl and $R_3$ is CHO which comprises alkylation of a compound of formula (V),

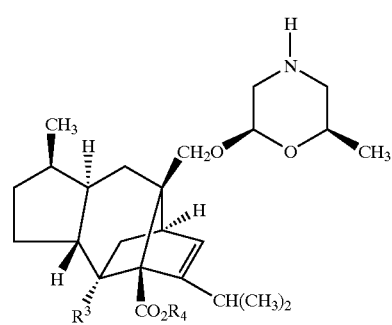

wherein $R_3$ is CHO or a protected aldehyde group as defined above and $R_4$ is a carboxyl protecting group or hydrogen or a cation;

(c) A process for preparing compounds of formula (I) wherein $R_1$ and $R_2$ have the meanings defined in claim 1 and $R_3$ is CHO which comprises reacting a sordaricin derivative (VIII) wherein $R_4$ is a carboxyl protecting group as defined above and Z is a leaving group,

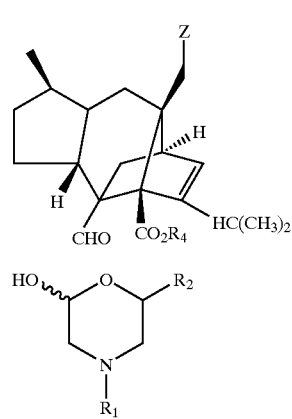

with the morpholino alcohol (IX) wherein $R_1$ and $R_2$ have the meanings defined above;

and if necessary of desired subjecting the resulting compound to one or more of the following operations:
1. removal of one or more protecting groups;
2. isolation of the compound as the free acid or a salt thereof;
3. conversion of a compound of formula (I) into a salt thereof; 4. Conversion of one compound of formula (I) into another compound of formula (I).

12. A pharmaceutical composition comprising a compound as claimed in claim 1 in admixture with one or more physiologically acceptable carriers or excipients.

13. A method of treatment of the human or non human animal body to treat fungal and or protozoal diseases which method comprises administering to said body an effective amount of a compound claimed in claim 1.

* * * * *